United States Patent [19]
Yu et al.

[11] Patent Number: 5,922,703
[45] Date of Patent: *Jul. 13, 1999

[54] URETHANE-CONTAINING AMINOSTEROID COMPOUNDS

[75] Inventors: Chia-Nien Yu, Norwich, N.Y.; Gilles Yves Genain, Wyoming, Ohio; Rachel Boujo, Paris, France

[73] Assignee: The Procter & Gamble Company, Cincinnati, Ohio

[*] Notice: This patent is subject to a terminal disclaimer.

[21] Appl. No.: 08/126,293

[22] Filed: Sep. 24, 1993

[51] Int. Cl.$^6$ .............................. A61K 31/56; C07J 41/00
[52] U.S. Cl. ............................................. 514/182; 552/515
[58] Field of Search .............................. 552/515; 514/182

[56] References Cited

U.S. PATENT DOCUMENTS

| | | |
|---|---|---|
| 4,325,879 | 4/1982 | Jarreau et al. . |
| 4,552,868 | 11/1985 | Jarreau et al. . |
| 4,584,289 | 4/1986 | Jarreau et al. . |
| 4,885,280 | 12/1989 | Jarreau et al. . |
| 5,144,017 | 9/1992 | LaBella et al. . |
| 5,175,281 | 12/1992 | McCall et al. . |

FOREIGN PATENT DOCUMENTS

| | | |
|---|---|---|
| 2642973 | 8/1987 | France . |
| 296 502A5 | 4/1979 | Germany . |
| 256 134A1 | 6/1985 | Germany . |
| 4-29089 | 10/1992 | Japan . |
| WO87/04167 | 7/1987 | United Kingdom . |
| WO87/04168 | 7/1987 | United Kingdom . |
| WO91/17176 | 11/1991 | WIPO . |

OTHER PUBLICATIONS

DiBianco, R., et al., "A Comparison of Oral Milrinone, Digoxin, and their Combination in the Treatment of Patients with Chronic Heart Failure", 320 *N. Engl. J. Med.* 677 (1989).

Goodman and Gilman, *The Pharmacological Basis of Therapeutics*, Chapter 34, (8th Ed., 1990).

Nicklas, J. M. and Pitt, B., et al. (The SOLVID Investigators) "Effect of Enalapril on Survival in Patients with Reduced Left Ventrical Ejection Fractions and Congestive Heart Failure", 325(5) *N. Engl. J. Med.* 293 (1991).

Templeton, J. et al., "Synthesis of 20–Hydroxy–, 20–Amino–, and 20–Nitro–14–hydroxy–21–nor–5β, 14β–pregnane C–3 Glycosides and Related Derivatives: Structure–Activity Relationships of Pregnanes That Bind to the Digitalis Receptor", 36 *J. Med. Chem.* 42–45 (1993).

Templeton, J. et al., "Synthesis of 20α– and 20β–Acetamido, Amino, Nitro and Hydroxy Derivatives of 14–Hydroxy–5β, 14β=pregnane 3β–Glycosides: Pregnanes that Bind to the Digitalis Receptor", 1 *J. Chem. Soc. Perkin Trans.* 2503–2517 (1992).

Adeoti, S., et al., "Introduction of A 14β–Nitrated Function Into The Steroid Ring To Prepare The Cardioactive Molecule, 14β–Amino–5β–Pregnane3β, 20β–Diol, From Progesterone and Deoxycholic Acid", 45 (12), *Tetradhedron* 3717–3730 (1989) (English Translation).

*Primary Examiner*—José G. Dees
*Assistant Examiner*—Barbara Badio
*Attorney, Agent, or Firm*—Mary Pat McMahon; William J. Winter; Karen F. Clark

[57] ABSTRACT

Urethane-containing amino steroids having the general chemical formula:

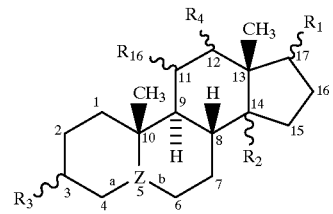

wherein a, b, $R_1$, $R_2$, $R_3$, $R_4$, $R_{14}$ and Z are as defined in the specification. Also disclosed are pharmaceutical composition and the use of the compounds/composition in the treatment of congestive heart failure.

13 Claims, No Drawings

URETHANE-CONTAINING AMINOSTEROID COMPOUNDS

BACKGROUND OF THE INVENTION

This invention relates to novel urethane-containing aminosteroid compounds. This invention also relates to pharmaceutical compositions containing these novel compounds as well as to a method of treating Congestive Heart Failure (CHF) using the compounds of the present invention.

CHF is a progressive disease wherein the heart is increasingly unable to supply adequate cardiac output (CO), which is the volume of blood pumped by the heart over time, to deliver the oxygenated blood to the peripheral tissues. When the heart initially fails, the rest of the body compensates for the loss in CO and such compensatory mechanisms eventually result in the syndrome known as CHF. As CHF progresses, structural and hemodynamic damages occur. Such structural damage manifests itself macroscopically as ventricular hypertrophy in the myocardium, and microscopically as interstitial, perivascular and replacement fibrosis in the ventricle wall, decreased myocardial capillary density, and myocardial cell death. When fibrosis of the myocardial tissue occurs it compromises the functioning of the heart because the remaining viable myocardial cells have a greater workload.

Hemodynamically, in the failing heart, the capacity to develop force during systole (the phase in the cardiac cycle during which ejection of blood from the ventricles occurs) is reduced. Thus, a greater end-diastolic volume (during the diastolic phase of the cardiac cycle filling of the ventricles occurs) is needed to perform any given level of external work. In cardiac failure, reduced ejection, caused by a mismatch of work capacity and load, results in an increase in end diastolic pressure and pulmonary capillary pressure. Pulmonary congestion and peripheral edema often follow. From the patient's perspective, as CHF progresses, the patient experiences increasingly worsening symptoms of fatigue and dyspnea.

Effective treatment of CHF requires a determination of its etiology, if possible, because some CHF etiologies have their own unique form of treatment. CHF has a variety of etiologies, including diseases of the myocardium such as coronary artery disease or myocarditis; diseases of the valves, such as mitral valve prolapse or aortic stenosis; pericardial diseases; congenital heart disease; pulmonary disease, cardiac arrhythmias, hypertension, and diabetes. For example, if the etiology of CHF is myocarditis or an arrhythmia, then treating the patient with an antimicrobial or an anti-arrhythmic agent, respectively, may restore the patient to normal cardiac function.

However, once the etiologies not responding to other treatments have been ruled out, treatment by one or more of three modalities is initiated: 1) improvement of the heart's pumping capacity by administration of an inotropic agent, such as digitalis, 2) reduction of the heart's workload by rest and/or by administration of vasodilators such as captopril, and 3) controlling sodium and water retention by a low sodium diet or administration of a diuretic such as thiazide. Treatment of CHF is individualized according to the patients symptomatology and tolerance for certain medications. For example, some patients may have a strong tendency to develop digitalis toxicity, while other patients with mild symptoms may benefit from diuretics which have a greater therapeutic index. Moreover, current wisdom suggests that diuretics are appropriate first line CHF therapy and that diuretic treatment should be followed by vasodilators and digitalis. It has also been noted that digitalis is most effective in patients suffering from severe CHF. See generally, Braunwald, *Heart Disease: A Textbook of Cardiovascular Medicine*, Vol. (3rd ed. 1988), Chung, E. K., *Quick Reference to Cardio-vascular Disease*, Chapter 27 (2d ed. 1983) and Fowler, N. O., *Cardiac Diagnosis and Treatment*, Chapter 12 (2d ed. 1976).

While digitalis is useful for ameliorating the symptoms associated with the hemodynamic problems characteristic of severe CHF, its low therapeutic index, in effect, limits its therapeutic utility. See generally, Braunwald, *Heart Disease: A Textbook of Cardiovascular Medicine*, Vol. (3rd ed. 1988), Chung, E. K., *Quick Reference to Cardiovascular Disease*, Chapter 27 (2d ed. 1983) and Fowler, N. O., *Cardiac Diagnosis and Treatment*, Chapter 12 (2d ed. 1976) and Goodman and Gilman, *The Pharmacological Basis of Therapeutics*, Chapter 34 (8th ed., 1990).

The toxicity problems associated with digitalis has prompted investigators to attempt to develop safer cardioactive compounds. Cardioactive steroid nucleus containing compounds have been described in the following patents: World Patent Publication WO 07/0416787/04167 to Chiodini, et al. published Jul. 16, 1987 describes aminoglycoside steroid derivatives substituted by an amino-sugar residue at the 3-position and an acetal linkage at the 14-position. The disclosure states that the compounds are useful for the treatment of hypertension. French Patent 2,642,973 of Guina published Aug. 17, 1990 describes a digitalis-like compound, 2,3-dioxymethyl-6-methyl-3-beta-D-glucose-strophanthidine, which contains the steroid nucleus substituted at the 3-position with a glucose moiety and at the 17-position with the lactone moiety, and at the 14-position with a hydroxyl group. The disclosure states that the compound is useful in preventing pathologic states resulting from cardiac insufficiencies for which digitalis is prescribed and for preventing pathologic states resulting from hypertension due to arterial calcification. The Guina compound is also alleged to be a positive inotrope, a peripheral vasodilator, and an anti-arrhythmic agent. World Patent Publication WO 87/04168 to Chiodini et al. published Jul. 16, 1987 discloses an aminoglycoside steroid having an alkyl substituted amino sugar at the 3-position, such as 2-amino or 2-alkylamino-2-deoxy-hexopyranosyl, 3-amino or 3-alkylamino-3-deoxy-hexo-pyranosyl, 3-amino or 3-alkyl-amino-3,6-dideoxy-hexopyranosyl, 3 amino or 3-alkylamino-2,3,6-trideoxy-hexopyranosy 4-amino or 4-alkylamino 2,4,6-trideoxy-hexopyranosyl residues, and a cyclic amide (lactam) at the 17-position. The 14-position is substituted with a H. The compound is said to be useful as an antihypertensive. World Patent Publication WO 91/17176 to Kenny, et al. published Nov. 14, 1991 discloses a steroid glycoside useful as a pressor agent, having a sugar moiety at the 3-position; such as a pentose, hexose or combinations thereof, and a lactone ring at the 17-position; the 14-position is substituted with an OH, H or a F, Cl, Br or $NH_2$; and DD 296,502 A5 to Siemann, et al. granted Dec. 5, 1991 discloses a steroid amide for treating cardial insufficiency wherein the 3-position is substituted with a sulphonyl amino group and the 17-position is substituted with a 5 or 6-membered lactone ring; the 14-position is substituted with an OH. U.S. Pat. No. 5,144,017 to LaBella, Sep. 1, 1992 discloses steroid compounds said to be useful as cardiac stimulants wherein the 3-position is substituted with a glycoside radical such as β-D-glucoside, α-L-rhamnoside, tridigitoxoside and the 17-position is substituted with an acetoxy group, or an amino group; and the 14-position has an OH group; and U.S. Pat. No. 5,175,281 to McCall, Dec. 29, 1992 discloses pyrimidinylpiperazinyl steroid compounds useful in treating spinal trauma, head injury and the subsequent cerebral vasospasm, preventing damage following cardiopulmonary resuscitation and cardiac infarction wherein the 3-position is OH, CH₃O, COOH, or benzoxy the 14-position is a H and the 17-position is a heterocyclic amine. DD 256,134 A1 to Wunderwald, et al., granted Apr. 27, 1988 discloses a process for making cardioactive steroids wherein the 3-position of the steroid molecule is substituted with a morpholinoformyloxy residue, and the 17-position of the steroid molecule is substituted with a lactone ring; and the 14-position is substituted with OH, H or an olefin. Said compounds are alleged to be useful for increasing cardiac contractility. JP 4-290899 to Ichikawa, et al., laid open Oct. 15, 1992, discloses a cardiotonic steroid compound wherein the 3-position of the steroid nucleus is substituted with an oligosaccharide; wherein further said oligosaccharide consists of three glucopyranosyl moieties and the 14-position is substituted with an OH group; and the 17-position is substituted with a lactone ring. Templeton, et al., 36 *J. Med. Chem.* 42–45 (1993) disclose the synthesis of derivatives of 14-hydroxy-21-nor-5β, 14β-pregnane and 5β,14β-pregnane C-3α-L-rhamnosides and tris-β-D-digitoxosides. Said compounds are reported to be effective cardiotonics. These derivatives, possessing a C-17βCOCH₂OH, CH₂OH, CO₂OH, CO₂Me, CH₂NH₂, or CH₂NO₂ group, bind to the digitalis receptor recognition site of heart muscle. Templeton, et al., *J. Chem. Sci. Perkin. Trans.*, 2503–2517 (1992) disclose the synthesis of 20α- and 20β-acetamido-, amino-, nitro- and hydroxy-3β-glycoside (α-L-rhamnopyranoside and tris-β-D-digitoxo-side) and genin derivatives of 14-hydroxy-5β,14β-pregnane together with the C-20 oxime, hydrazone and amidinohydrazone. These compounds are asserted to be effective cardiotonics. Adeoti, S. B., et al., 12 *Tetrahedron Letters*, 3717–3730 (1989) disclose a method for introducing a 14β-amino function into a steroid molecule. Said method allows for the preparation of the cardioactive 14β-amino-5β-pregnane-3β, 20βdiol.

Additionally, angiotensin converting enzyme inhibitors (ACEI) have been shown to reduce mortality in CHF patients. See Nicklas, J. M. and Pitt, B., et al. (The SOLVD Investigators), "Effect of Enalapril on Survival in Patients with Reduced Left Ventricular Ejection Fractions and Congestive Heart Failure", N. *Engl. J. Med.* 325(5):293 (1991).

Nevertheless, four million people still suffer from CHF. The five year mortality after diagnosis of CHF is 60% for men and 45% for women. This is a clear indication that better therapies directed toward treating CHF are needed. See Parmley, W. W., "Pathophysiology and Current Therapy of Congestive Heart Failure", *J. Am. Col. Cardiol.* 13:771–785 (1989); Francis, G. S. et al., "Congestive Heart Failure: Pathophysiology and Therapy,"*Cardiovascular Pharmacology,* 3rd Edition (1990).

The 14-aminosteroid compounds have been shown to be useful in treating CHF by increasing cardiac contractility. These compounds provide the therapeutic benefit of increased cardiac contractility without the side effects of digitalis. These 14-aminosteroids are described in the following three patents, all incorporated by reference herein: U.S. Pat. No. 4,552,868, Jarreau, et al., issued Nov. 12, 1985; U.S. Pat. No. 4,584,289 Jarreau, et al., issued Apr. 22, 1986 and U.S. Pat. No. 4,885,280 Jarreau, et al., issued Dec. 5, 1989. These three patents describe 14-aminosteroid compounds possessing positive inotropic activity. It has now been discovered that the urethane-containing aminosteroid compounds of the present invention wherein the 3-position is substituted with a urethane-containing moiety are more effective inotropes. Said urethane-containing aminosteroids are more resistant to metabolism and therefore provide a longer duration of inotropic activity than the prior art 14-aminosteroids.

SUMMARY OF THE INVENTION

Urethane-containing aminosteroid compounds and the pharmaceutically-acceptable acid salts or esters thereof of the general formula wherein:

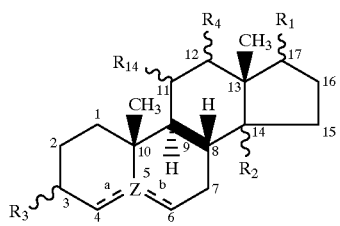

a) $R_1$ is
   (i) $COOR_5$, where
      $R_5$ is hydrogen; a 1–6 carbon lower alkyl group; a 1–6 carbon lower alkyl group containing 2 to 6 carbon atoms substituted by an amino group; an arylalkyl group or heteroarylalkyl group or a carbocyclic ring or
   (ii) $CHR_6OH$, where
      $R_6$ is a hydrogen atom or 1–6 carbon group lower alkyl; or
   (iii) $COR'''$, where $R'''$ is hydrogen; 1–6 carbon lower alkyl; amino; 1–6 carbon lower alkyl substituted amino; or dialkylamino; or
   (iv) $CHR_6NHY$, where Y is hydrogen or a 1–6 carbon lower alkyl; or
   (v) a 5- or 6-membered α- or β-unsaturated lactone ring;

b) $R_2$ is
   (i) $—NR_7R_8$, where
      $R_7$ and $R_8$, which may be the same or different; are hydrogen atoms or a 1–6 carbon lower alkyl group; or
   (ii) OH; and c) $R_3$ is
   (i) a urethane-containing moiety, where

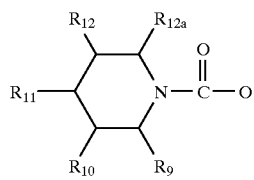

$R_9$, $R_{10}$, $R_{11}$, $R_{12}$ and $R_{12a}$, which may be the same or different; are hydrogen; 1–6 carbon lower alkyl; benzoxy; hydroxy; hydroxyalkyl; acetoxy; amino;

phenyl; alkylamino or arylalkylamino; or
(ii) a urethane-containing moiety, where

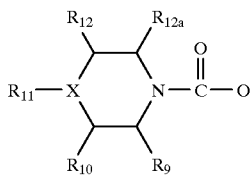

X is $NR_{11}$, O or S, and $R_9$; $R_{10}$; $R_{12}$; $R_{12a}$; which may be the same or different; are hydrogen; 1–6 carbon lower alkyl; benzoxy; hydroxy; hydroxyalkyl; acetoxy; amino; phenyl or alkylamino; and $R_{11}$ is hydrogen; 1–6 carbon lower alkyl; arylalkyl; heteroarylalkyl; hydroxy; hydroxyalkyl; aryl or heteroaryl; and wherein further, when X is O or S, said O or S is unsubstituted, and
(iii) a urethane-containing moiety, where

wherein X can be O or S; R'R" are independently selected from hydrogen; substituted or unsubstituted linear; branched or cyclic 1–6 carbon lower alkyl; alkylaminoalkyl; arylalkyl; heteroarylalkyl; aryl; heteroaryl; a substituted or unsubstituted carbocyclic ring; a substituted or unsubstituted saturated; heterocyclic ring or a substituted or unsubstituted aromatic heterocyclic ring; wherein further said substitutents are selected from hydroxy; amino; alkoxy; 1–6 carbon alkyl; amino; heteroaryl; aryl; saturated heterocyclic rings; hydroxyalkyl; alkylaminoalkyl; arylalkyl or heteroarylalkyl; and
(iv) a urethane-containing moiety, where

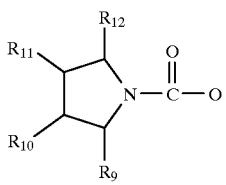

$R_9$, $R_{10}$, $R_{11}$ and $R_{12}$ which may be the same or different; are hydrogen; 1–6 carbon lower alkyl; benzoxy; hydroxy; hydroxyalkyl; acetoxy; amino; phenyl; alkylamino or arylalkylamino; and
(v) a urethane-containing moiety, where

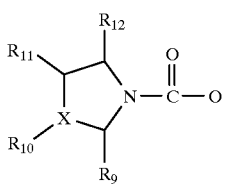

X is $NR_{10}$, O or S, and $R_9$; $R_{11}$; and $R_{12}$ which may be the same or different; are hydrogen; 1–6 carbon lower alkyl; benzoxy; hydroxy; hydroxyalkyl; acetoxy; amino; phenyl or alkylamino; and $R_{10}$ is hydrogen; 1–6 carbon lower alkyl; arylalkyl; heteroarylalkyl; hydroxy; hydroxyalkyl; aryl or heteroaryl; and wherein further, when X is O or S, said O or S is unsubstituted, and
d) $R_4$ is
   (i) OH, or
   (ii) H, or
   (iii) $OR_{13}$, where $R_{13}$ is a monosaccharide sugar residue; acetoxy; benzoxy; arylalkyl or heteroarylalkyl; and
e) $R_{14}$ is
   (i) OH, or
   (ii) H, or
   (iii) $OR_{13}$, where $R_{13}$ is a monosaccharide residue; acetoxy; benzoxy; arylalkyl or heteroarylalkyl and
f) Z is
   (i) —CH—, where a and b are single bonds, or
   (ii) =C, where either a or b is a double bond.

DEFINITIONS AND USAGE OF TERMS

The following is a list of definitions for terms used herein.

"aminosteroid" is a steroid ring compound having an amino group on the steroid nucleus.

"Alkyl" is an unsubstituted or substituted, straight-chain, cyclic or branched, saturated hydrocarbon chain having 1 to 8 carbon atoms, and preferably, unless otherwise stated, from 1 to 6 carbon atoms. Preferred alkyl groups include, but are not limited to, methyl, ethyl, propyl, isopropyl, and butyl; a monovalent radical derived from an aliphatic hydrocarbon by removal of 1H; as methyl. A lower alkyl group contains 1–6 carbon atoms.

"Heteroalkyl" as used herein is an unsubstituted or substituted, saturated chain having from 3 to 8-members and comprising carbon atoms and one or two heteroatoms.

"Alkenyl" is an unsubstituted or substituted, straight-chain or branched, hydrocarbon chain having from 2 to 8 carbon atoms, preferably from 2 to 4 carbon atoms, and having at least one olefinic double bond.

"Alkynyl" is an unsubstituted or substituted, straight-chain or branched, hydrocarbon chain having from 2 to 8 carbon atoms, preferably from 2 to 4 carbon atoms, and having at least one triple bond.

"Acetate": A salt of acetic acid containing the $CH_3COO$— radical.

"Acetoxy": Acetyloxy. The radical $CH_3COO$—.

"Acetyl": The acyl radical $CH_3CO$—.

"Aglycone": That component of a glycoside, e.g., plant pigment, which is not a sugar.

"Carbocyclic ring" or "Carbocycle" as used herein is an unsubstituted or substituted, saturated, unsaturated or aromatic, hydrocarbon ring, generally containing from 3 to 8 atoms, preferably 5 to 7 atoms.

"Heterocyclic ring" or "Heterocycle" as used herein is an unsubstituted or substituted, saturated or unsaturated or aromatic ring comprised of carbon atoms and one or more heteroatoms in the ring. Heterocyclic rings generally contain from 3 to 8, preferably 5 to 7, atoms. Unless otherwise stated, the heteroatom may be independently chosen from nitrogen, sulfur, and oxygen.

"Aryl" is an aromatic carbocyclic ring. Aryl groups include, but are not limited to, phenyl, tolyl, xylyl, cumenyl, and naphthyl; an organic radical derived from an aromatic hydrocarbon by the removal of one atom; e.g. phenyl from benzene.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g. —O—alkyl or —O—alkenyl); "Alkoxy" An alkyl radical attached to the remainder of the molecule by oxygen; as, methoxy. Preferred alkoxy groups include, but are not limited to, methoxy, ethoxy, propoxy, and alkyloxy.

"Hydroxyalkyl" is a substituted hydrocarbon chain which has a hydroxy substituent (e.g. —OH), and may have other substituents. Preferred hydroxyalkyl groups include, but are not limited to, hydroxyethyl, hydroxypropyl, phenylhydroxyalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain, (e.g. alkyl) substituted with an amine moiety (e.g. NH—alkyl-), such as dimethylamino alkyl.

"Alkylamino" is an amino moiety having one or two alkyl substituents (e.g. —N-alkyl).

"Alkenylamino" is an amino moiety having one or two alkenyl substituents (e.g. —N-alkenyl).

"Alkynylamino" is an amino moiety having one or two alkynyl substituents (e.g. —N-alkynyl).

"Alkylimino" is an imino moiety having one or two alkyl substituents (e.g. N=alkyl-).

"Arylalkyloxy" is an oxygen atom having an "arylalkyl" substituent, e.g. phenylmethoxy, phenylmethylene oxy

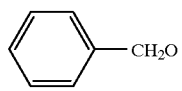

"Heteroarylalkyloxy" is an oxygen atom having a "heteroarylalkyl" substituent, e.g.

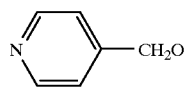

"Arylalkyl" is an alkyl moiety substituted with an aryl group. Preferred arylalkyl groups include benzyl and phenylethyl.

"Heteroarylalkyl" is an alkyl moiety substituted with a heteroaryl group.

"Arylamino" is an amino moiety substituted with an aryl group (e.g. —NH-aryl).

"Aryloxy" is an oxygen atom having an aryl substituent (e.g. —O-aryl).

"Acyl" or "carbonyl" is a moiety formed by removal of the hydroxy from a carboxylic acid (e.g. R—C(=O)—). Preferred alkylacyl groups include, but are not limited to, acetyl, propionyl, and butanoyl.

"Acyloxy" is an oxygen atom having an acyl substituent (e.g. —O -acyl); for example, —O—C(=O)-alkyl.

"Acylamino" is an amino moiety having an acyl substituent (e.g. —N-acyl); for example, —NH—(C=O)-alkyl.

"Benzoxy": The benzoyloxy radical.

"Benzoyl": The aryl radical, $C_6H_5CO$—, derived from benzoic acid.

"Benzoyloxy": Benzoxy. The radical $C_6H_5COO$—, derived from benzoic acid.

"Carbamate": A salt of carbamic acid; it contains the —$NCO_2$— radical, also known in the art as a "urethane" or a carbamic ester.

"Carboxy": Prefix indicating the acidic carboxyl group.

"Ester": An organic salt formed from an alcohol (base) and an organic acid by elimination of water; functional group derivatives of carboxylic acids are those compounds that are transformed into carboxylic acids by simple hydrolysis. The most common such derivatives are esters, in which the hydroxy group is replaced by an alkoxy group;

"Glycoside": A natural compound of a sugar with another substance, which hydrolyzes a sugar plus a principle: (e.g. coniferin yields glucose plus coniferyl alcohol as the principle; glucosides yield glucose, fructosides yield fructose, galactosides yield galactose, etc.; the cyclic acetal of a carbohydrate.

"Halo", "halogen", or "halide" is a chloro, bromo, fluoro, or iodo atom radical. Chloro, bromo, and fluoro are preferred halides.

"Lactone": Any of a class of inner esters of hydroxy carboxylic acids formed by the loss of a molecule of water from the hydroxy and carboxyl groups of the acids, characterized by the carbonyl-oxy grouping —OCO— in a ring, and classed according to the position of the hydroxy group in the parent acid; cyclic ester.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halides (such as chloride) salts.

"Salts": Substances produced from the reaction between acids and bases; a compound of a metal (positive) and nonmetal (negative) radical : M.OH (base)+HX (acid)=MX (salt)+$H_{20}$ (water).

"Steroid nucleus": Generic name for a family of lipid compounds comprising the sterols, bile acids, cardiac glycosides, saponins, and sex hormones.

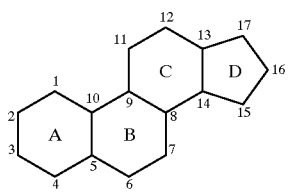

"Substituent": Any atom or group replacing the hydrogen of a parent compound.

"Substitute": To replace one element or radical in a compound by a substituent.

"Substituted": Pertaining to a compound which has undergone substitution.

"Substitution": A reaction in which an atom or group of atoms in a (usually organic) molecule is exchanged for another.

Substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

"monosaccharide": A single sugar moiety; e.g. hexose, 2-deoxyglucose, 6-deoxyhexose, 2,6-dideoxyhexose, etc., rhamnose, glucose, arabinose, digitoxose, fructose, galactose; rhamnopyranose, hexopyranose, 6-deoxyglucose, 4,6-dideoxy-glycopyranose, mannose, cymarose, xylose, lyxose, ribose, digitalose, 4-amino-2,4,6-trideoxylyxohexopyranose, 4-amino 4,6, dideoxyglucopyranose, 2,3-dideoxyrhamnopyranose, 4-methoxy 4,6-dideoxy rhamnopyranose.

The monosaccharide residue can be graphically depicted in either a ring or a chair configuration. For example, glucose (a monosaccharide) can be represented accordingly:

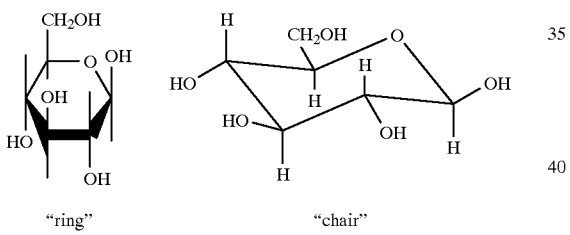

"ring"  "chair"

DETAILED DESCRIPTION OF THE INVENTION

The present invention encompasses certain urethane-containing aminosteroid compounds, methods for their manufacture, pharmaceutical compositions thereof, and a method of treatment utilizing said urethane-containing aminosteroid compounds and compositions thereof for treating congestive heart failure in humans or other mammals. Specific compounds and compositions to be used in the invention must, accordingly, be pharmaceutically-acceptable. As used herein, such a "pharmaceutically-acceptable" component is one that is suitable for use with humans and/or other mammals without undue adverse side effects (such as toxicity, irritation, and allergic response), commensurate with a reasonable benefit/risk ratio.

ACTIVE MATERIALS

Urethane-containing 14-aminosteroid compounds and the pharmaceutically-acceptable acid salts or esters thereof of the general formula:

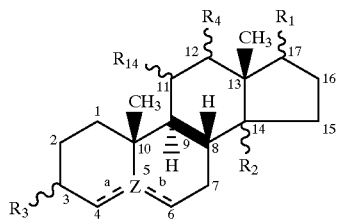

wherein
a) $R_1$ is
  (i) $COOR_5$, where
    $R_5$ is hydrogen; a 1–6 carbon lower alkyl group; a 1–6 carbon lower alkyl group containing 2 to 6 carbon atoms substituted by an amino group; an arylalkyl group or heteroarylalkyl group or a carbocyclic ring or
  (ii) $CHR_6OH$, where
    $R_6$ is a hydrogen atom or 1–6 carbon group lower alkyl; or
  (iii) $COR'''$, where $R'''$ is hydrogen; 1–6 carbon lower alkyl; amino; 1–6 carbon lower alkyl substituted amino; or dialkylamino; or
  (iv) $CHR_6NHY$, where Y is hydrogen or a 1–6 carbon lower alkyl; or
  (v) a 5- or 6-membered α- or β-unsaturated lactone ring;
b) $R_2$ is
  (i) —$NR_7R_8$, where
    $R_7$ and $R_8$, which may be the same or different; are hydrogen atoms or a 1–6 carbon lower alkyl group; or
  (ii) OH; and
c) $R_3$ is
  (i) a urethane-containing moiety, where

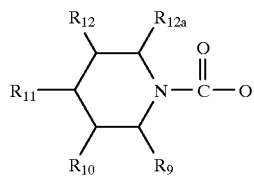

$R_9$, $R_{10}$, $R_{11}$, $R_{12}$ and $R_{12a}$, which may be the same or different; are hydrogen; 1–6 carbon lower alkyl; benzoxy; hydroxy; hydroxyalkyl; acetoxy; amino; phenyl; alkylamino or arylalkylamino; or
  (ii) a urethane-containing moiety, where

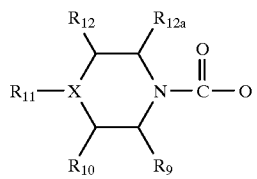

X is $NR_{11}$, O or S, and $R_9$; $R_{10}$; $R_{12}$; $R_{12a}$; which may be the same or different; are hydrogen; 1–6 carbon lower alkyl; benzoxy; hydroxy; hydroxyalkyl; acetoxy; amino; phenyl or alkylamino; and $R_{11}$ is hydrogen; 1–6 carbon lower alkyl; arylalkyl; heteroarylalkyl; hydroxy; hydroxyalkyl; aryl or heteroaryl; and wherein further, when X is O or S, said O or S is unsubstituted, and (iii) a urethane-containing moiety, where

wherein X can be O or S; R'R" are independently selected from hydrogen; substituted or unsubstituted linear; branched or cyclic 1–6 carbon lower alkyl; alkylaminoalkyl; arylalkyl; heteroarylalkyl; aryl; heteroaryl; a substituted or unsubstituted carbocyclic ring; a substituted or unsubstituted saturated; heterocyclic ring or a substituted or unsubstituted aromatic heterocyclic ring; wherein further said substitutents are selected from hydroxy; amino; alkoxy; 1–6 carbon alkyl; amino; heteroaryl; aryl; saturated heterocyclic rings; hydroxyalkyl; alkylaminoalkyl; arylalkyl or heteroarylalkyl; and (iv) a urethane-containing moiety, where

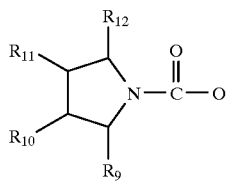

$R_9$, $R_{10}$, $R_{11}$ and $R_{12}$ which may be the same or different; are hydrogen; 1–6 carbon lower alkyl; benzoxy; hydroxy; hydroxyalkyl; acetoxy; amino; phenyl; alkylamino or arylalkylamino; and (v) a urethane-containing moiety, where

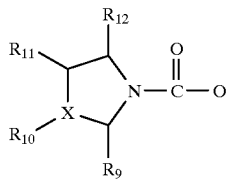

X is $NR_{10}$, O or S, and $R_9$; $R_{11}$; and $R_{12}$ which may be the same or different; are hydrogen; 1–6 carbon lower alkyl; benzoxy; hydroxy; hydroxyalkyl; acetoxy; amino; phenyl or alkylamino; and $R_{10}$ is hydrogen; 1–6 carbon lower alkyl; arylalkyl; heteroarylalkyl; hydroxy; hydroxyalkyl; aryl or heteroaryl; and wherein further, when X is O or S, said O or S is unsubstituted, and d) $R_4$ is
(i) OH, or
(ii) H, or
(iii) $OR_{13}$, where $R_{13}$ is a monosaccharide sugar residue; acetoxy; benzoxy; arylalkyl or heteroarylalkyl; and e) $R_{14}$ is
(i) OH, or
(ii) H, or
(iii) $OR_{13}$, where $R_{13}$ is a monosaccharide residue; acetoxy; benzoxy; arylalkyl or heteroarylalkyl and f) Z is
(i) —CH—, where a and b are single bonds, or
(ii) =C, where either a or b is a double bond.

The "~" symbol, as used herein, indicates that the stereochemistry is undefined, and that the substituents on the steroid nucleus can be in either the α or β configuration.

The Steroid Nucleus

The novel urethane-containing compounds of the present invention are comprised of a steroid nucleus wherein said steroid nucleus is variously substituted.

The Substituents on the Steroid Nucleus

The $R_1$ Substituents

The $R_1$ substituent is at the 17-position on the steroid nucleus. There are five (5) possible $R_1$ substituents. $R_1$ can be $COOR_5$ where $R_5$ is hydrogen, a lower alkyl group containing 1 to 6 carbon atoms, a lower alkyl group containing 2 to 6 carbon atoms substituted by an amino group, an arylalkyl group or a heteroarylalkyl or a carbocyclic ring.

The preferred $R_5$ is a 1–6 carbon lower alkyl, arylalkyl or a carbocycle, the more preferred $R_5$ is a 1–6 carbon lower alkyl and the most preferred $R_5$ is methyl; thus, $R_1$ is $COOCH_3$ (carboxymethylester):

$R_1$ can also be $CHR_6OH$ where $R_6$ is a hydrogen atom or lower alkyl group containing 1 to 6 carbon atoms; the preferred $R_6$ is H or methyl; thus, $R_1$ is $CH_2OH$ or $CH(CH_3)OH$.

$R_1$ can be COR''', where $R_1$''' is hydrogen, lower alkyl, methylamino, amino or dialkylamino. The preferred R''' is 1–6 carbon lower alkyl or methylamino. The most preferred R''' is methylamino; thus, $R_1$ is $CONHCH_3$.

$R_1$ is also $CHR_6NHY$ where Y is hydrogen or a 1–6 carbon lower alkyl. The preferred Y is H and the preferred $R_6$ is H; thus, $R_1$ is $CH_2NH_2$.

Finally, $R_1$ can be a 5- or 6-membered α or β unsaturated lactone ring. The preferred lactone ring is a β unsaturated 5-membered ring substituted at the β-position.

A preferred $R_1$ is COR'''where R''' is amino. The most preferred $R_1$ substituent is $COOR_5$, where $R_5$ is methyl; thus, the most preferred $R_1$ is carboxymethylester ($COOCH_3$).

The $R_2$ Substituents

The $R_2$ substituent is at the 14-position on the steroid nucleus. There are two (2) possible $R_2$ substituents. $R_2$ can be —$NR_7R_8$ where $R_7$ and $R_8$, which may be the same or different, are hydrogen atoms or a 1–6 carbon lower alkyl. Preferably $R_7$ and $R_8$ are H and thus, $R_2$ is $NH_2$. $R_2$ can also be a hydroxy group. The preferred $R_2$ substituent is the $NH_2$ group.

The $R_3$ Substituents

The $R_3$ substituent is at the 3-position on the steroid nucleus. There are five (5) possible $R_3$ substituents. $R_3$ can be a urethane-containing moiety having the following structure:

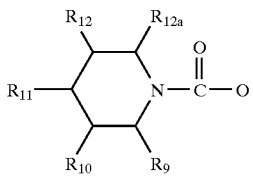

Said urethane-containing moiety is comprised of a piperidine ring which is variously substituted by $R_9$, $R_{10}$, $R_{11}$, $R_{12}$ and $R_{12a}$. $R_9$, $R_{10}$, $R_{11}$, $R_{12}$ and $R_{12a}$, which may be the same or different, are hydrogen, 1–6 carbon lower alkyl, benzoxy; hydroxy; hydroxy alkyl; acetoxy; amino; phenyl, alkylamino, or arylalkylamino.

One skilled in the art of organic chemistry understands that each carbon atom in the piperidine ring has two remaining sites for binding of substituents. Thus, each carbon atom in the piperidine ring can be monosubstituted or disubstituted.

Preferred $R_9$ substituents are hydrogen, 1–6 carbon lower alkyl and hydroxy. The most preferred $R_9$ substituents are hydrogen and methyl. Preferred $R_{10}$ substituents are acetoxy, hydroxy, and hydrogen and 1–6 carbon lower alkyl. The most preferred $R_{10}$ substituents are hydrogen, hydroxy, acetoxy and methyl.

Preferred $R_{11}$ substituents are hydrogen, amino, hydroxy, hydroxyalkyl and 1–6 carbon lower alkyl. The most preferred $R_{11}$ substituents are hydrogen, hydroxyethyl; and amino. Preferred $R_{12}$ substituents are hydrogen, hydroxy, 1–6 carbon lower alkyl, and acetoxy. Preferred $R_{12a}$ substituents are hydrogen, hydroxy and 1–6 carbon lower alkyl.

$R_3$ is also a urethane-containing moiety having the following structure:

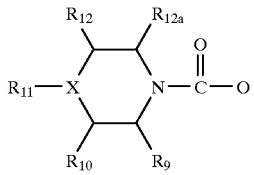

Said urethane-containing moiety is comprised of a 6-membered heterocyclic ring, wherein said heteroatom (X) in said heterocyclic ring is $NR_{11}$, O or S and wherein further said heterocyclic ring is variously substituted by $R_9$, $R_{10}$, $R_{11}$, $R_{12}$ and $R_{12a}$. $R_9$, $R_{10}$, $R_{12}$, $R_{12a}$, which may be the same or different, are hydrogen; 1–6 carbon lower alkyl; benzoxy; hydroxy; hydroxy alkyl; acetoxy; amino; phenyl or alkyl amino; and $R_{11}$ is hydrogen; arylalkyl; heteroarylalkyl; hydroxy; hydroxyalkyl; 1–6 carbon lower alkyl; aryl or heteroaryl. Further, when the heteroatom (X) is oxygen or sulfur, said O or S is unsubstituted. A preferred 6-membered heterocyclic ring is the piperazine ring.

One skilled in the art of organic chemistry understands that each carbon atom in the piperazine ring has two remaining sites for binding of substituents. Thus, each carbon atom in the piperazine ring can be monosubstituted or disubstituted. Preferred $R_9$ substitutents are hydrogen or 1–6 carbon lower alkyl. The most preferred $R_9$ substituent is hydrogen.

Preferred $R_{10}$ substituents are hydrogen and 1–6 carbon lower alkyl. The most preferred $R_{10}$ substituent is hydrogen.

Preferred $R_{11}$ substituents are 1–6 carbon lower alkyl, hydroxyalkyl and arylalkyl. The most preferred $R_{11}$ substituents are hydroxyethyl and arylalkyl.

Preferred $R_{12}$ substituents are hydrogen and 1–6 carbon lower alkyl. The most preferred $R_{12}$ substituent is hydrogen.

Preferred $R_{12a}$ substituted are hydrogen and 1–6 carbon lower alkyl. The most preferred $R_{12a}$ substituent is hydrogen.

$R_3$ can be a urethane-containing moiety having the following structure:

wherein X can be O or S; R'R'' are independently selected from hydrogen; substituted or unsubstituted linear; branched or cyclic 1–6 carbon lower alkyl; alkylaminoalkyl; arylalkyl; heteroarylalkyl; heteroaryl; aryl; a substituted or unsubstituted carbocyclic ring; a substituted or unsubstituted saturated, heterocyclic ring or a substituted or unsubstituted aromatic heterocyclic ring; wherein further said substitutents are selected from hydroxy; amino; alkoxy; 1–6 carbon lower alkyl; amino; aryl; heteroaryl; saturated heterocyclic rings; hydroxyalkyl; alkylaminoalkyl; amino; arylalkyl or heteroarylalkyl. Further, when $R_3$ is:

the R' or R'' substituents can be attached to either the N or O atom. The preferred point of attachment for the R' or R'' substituents is the N atom.

Thus, when $R_3$ is:

$R_3$ can be, for example, a substituted aminocarbonyloxy (i.e. X=O),

or
a substituted aminothiocarbonyloxy (i.e. X=S):

R' and R'' are the substituents on the aminocarbonyloxy or aminothiocarbonyloxy moiety.

The preferred X is O. Preferred R'' substituents are hydrogen and 1–6 carbon lower alkyl. The most preferred R'' substituents are hydrogen and methyl.

The preferred R' substituents are substituted or unsubstituted, linear or branched 1–6 carbon lower alkyl; alkylaminoalkyl and arylalkyl. The most preferred R' substituent is a substituted or unsubstituted linear or branched 1–6 carbon lower alkyl, wherein further, when said 1–6 carbon lower alkyl is substituted, it is substituted with OH, $NH_2$, 1–6 carbon lower alkyl, alkoxy or phenyl or alkylamino.

$R_3$ can also be a urethane-containing moiety having the following structure where:

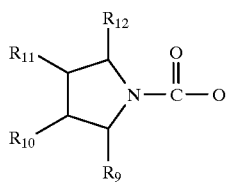

Said urethane moiety is comprised of a pyrrolidinyl ring which is variously substituted by $R_9$, $R_{10}$, $R_{11}$ and $R_{12}$ which may be the same or different; are hydrogen; 1–6 carbon lower alkyl; benzoxy; hydroxy; hydroxyalkyl; acetoxy; amino; phenyl; alkylamino or arylalkylamino; and Finally, $R_3$ can be a urethane-containing moiety, having the following structure where:

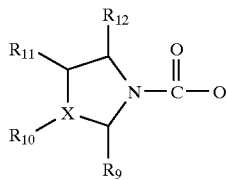

Said urethane-containing moiety is comprised of a five-membered heterocyclic ring, wherein said heteroatom (X) in said heterocyclic ring is $NR_{10}$, O or S, and wherein in further said heterocyclic ring is variously substituted by $R_9$, $R_{10}$, $R_{11}$, and $R_{12}$, $R_9$; $R_{11}$; and $R_{12}$ which may be the same or different; are hydrogen; 1–6 carbon lower alkyl; benzoxy; hydroxy; hydroxyalkyl; acetoxy; amino; phenyl or alkylamino; and $R_{10}$ is hydrogen; 1–6 carbon lower alkyl; arylalkyl; heteroarylalkyl; hydroxy; hydroxyalkyl; aryl or heteroaryl. Further, when the heteroatom (X) is O or S, said O or S is unsubstituted. A preferred 5-membered heterocyclic ring is the thiazolidinyl ring.

The $R_4$ Substituents

The $R_4$ substituent is at the 12-position on the steroid nucleus. $R_4$ can be OH, H or $OR_{13}$, where $R_{13}$ is a monosaccharide sugar residue; acetoxy; benzoxy; arylalkyl or heteroarylalkyl. The preferred $R_4$ substituents are H or $OR_{13}$, where $R_{13}$ is a monosaccharide residue. Said monosaccharide residue is selected from hexose, 2-deoxyglucose, 6-deoxyhexose, 2,6-dideoxyhexose, rhamnose, a glucose and arabinose, a digitoxose, a fructose, a galactose, rhamnopyrannose, hexopyranose, 6-deoxyglucose, 4,6-dideoxy-glycopyranose, mannose, cymarose, xylose, lyxose, ribose, digitalose, glucosamine, 4-amino-2,4,6-trideoxy lyxohexopyranose, 4-amino-4,6-dideoxy glycopyramose, 2,3-didexoy rhamnopyranose, 4-methoxy 4,6-dideoxyrhamnopyranose, preferably the β-D or α-L anomers thereof.

The most preferred $R_4$ substituent is H.

The $R_{14}$ Substituents

The $R_{14}$ substituent is at the 11-position on the steroid nucleus. $R_{14}$ can be OH, H or $OR_{13}$, where $R_{13}$ is a monosaccharide sugar residue; acetoxy; benzoxy; arylalkyl or heteroarylalkyl. The preferred $R_{14}$ substituents are hydroxy or acetoxy.

Z

Z is —CH—, where a and b are single bonds, or =C, where either a or be is a double bond. The preferred Z is —CH where a and b are single bonds.

Preferred urethane-containing aminosteroid compounds of the present invention are:

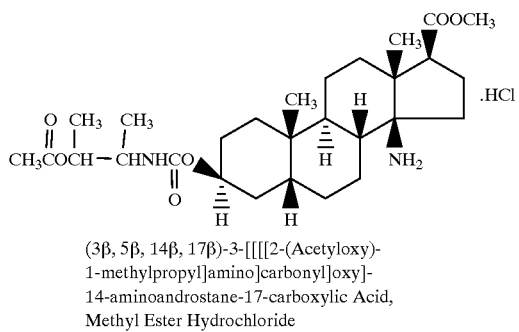

(3β, 5β, 14β, 17β)-3-[[[[2-(Acetyloxy)-
1-methylpropyl]amino]carbonyl]oxy]-
14-aminoandrostane-17-carboxylic Acid,
Methyl Ester Hydrochloride

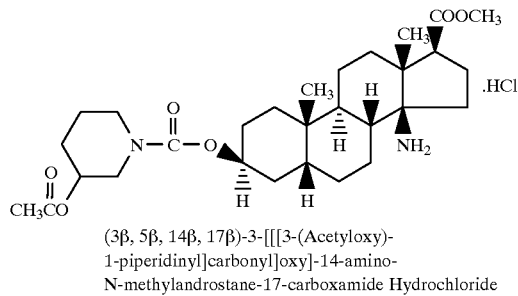

(3β, 5β, 14β, 17β)-3-[[[3-(Acetyloxy)-
1-piperidinyl]carbonyl]oxy]-14-amino-
N-methylandrostane-17-carboxamide Hydrochloride

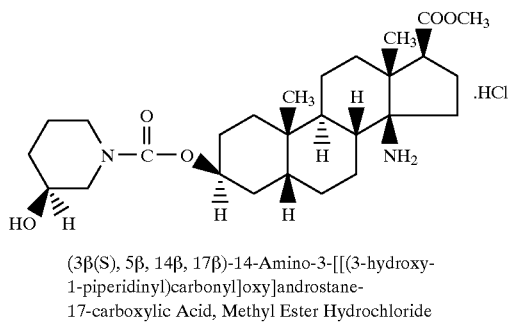

(3β(S), 5β, 14β, 17β)-14-Amino-3-[[(3-hydroxy-
1-piperidinyl)carbonyl]oxy]androstane-
17-carboxylic Acid, Methyl Ester Hydrochloride

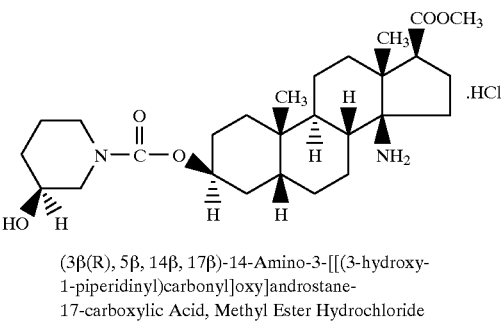

(3β(R), 5β, 14β, 17β)-14-Amino-3-[[(3-hydroxy-
1-piperidinyl)carbonyl]oxy]androstane-
17-carboxylic Acid, Methyl Ester Hydrochloride

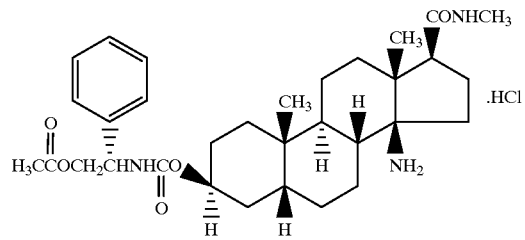

(3β(S), 5β, 14β, 17β)-3-[[[[2-(Acetyloxy)-
1-phenylethyl]amino]carbonyl]oxy]-14-amino-
N-methylandrostane-17-carboxamide Hydrochloride

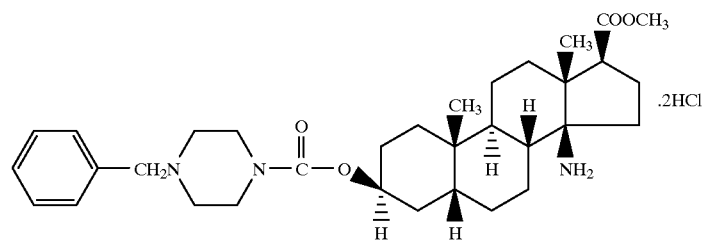

(3β, 5β, 14β, 17β)-14-Amino-3-[[[4-(phenylmethyl)-
1-piperazinyl]carbonyl]oxy]androstane-17-carboxylic
Acid, Methyl Ester Dihydrochloride

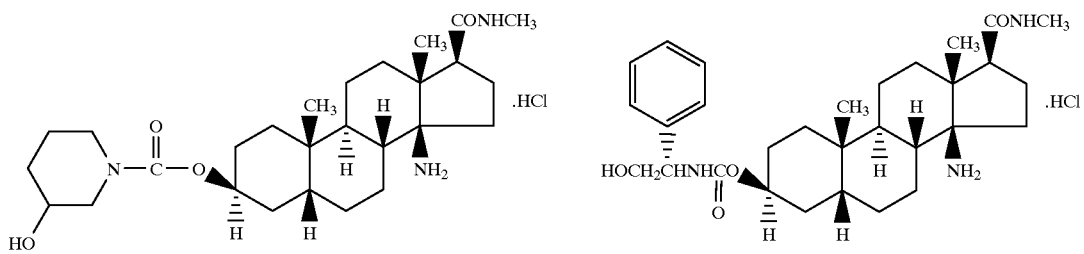

(3β, 5β, 14β, 17β)-14-Amino-3-[[(3-hydroxy-1-piperidinyl)-
carbonyl]oxy]-N-methylandrostane-17-carboxamide Hydro-
chloride (3β(S), 5β, 14β, 17β)-14-Amino-3-[[[(2-hydroxy-phenyl-
ethyl)amino]carbonyl]oxy]-N-methlandrostane-17-carbox
amide Hydrochloride

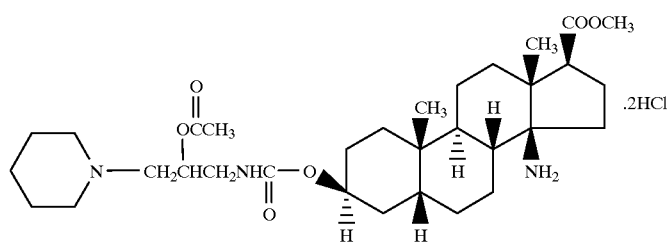

(3β, 5β, 14β, 17β)-3-[[[[2-Acetyloxy-
3-(1-piperidinyl)propyl]amino]carbonyl]oxy]-
14-aminoandrostane-17-carboxylic Acid,
Methyl Ester Dihydrochloride

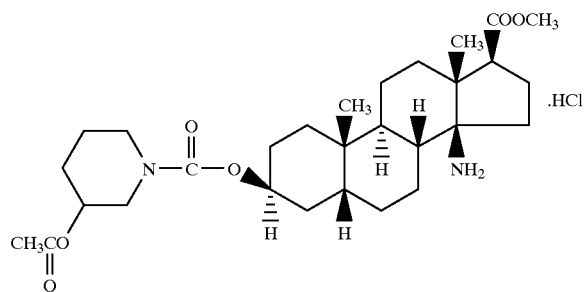

(3β, 5β, 14β, 17β)-3-[[[3-(Acetyloxy)-
1-piperidinyl]carbonyl]oxy]-14-aminoandrostane-
17-carboxylic Acid, Methyl Ester Hydrochloride

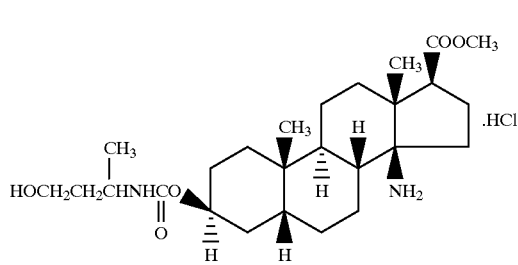

(3β, 5β, 14β, 17β)-14-Amino-3-[[[3-hydroxy-
1-methylpropyl)amino]carbonyl]oxy]androstane-
17-carboxylic Acid, Methyl Ester Hydrochloride

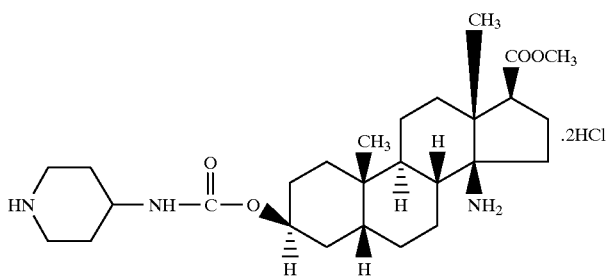

(3β, 5β, 14β, 17β)-14-Amino-3-[[[(4-piperidinyl)amino-
carbonyl]oxy]androstane-17-carboxylic Acid, Methyl
Ester Dihydrochloride

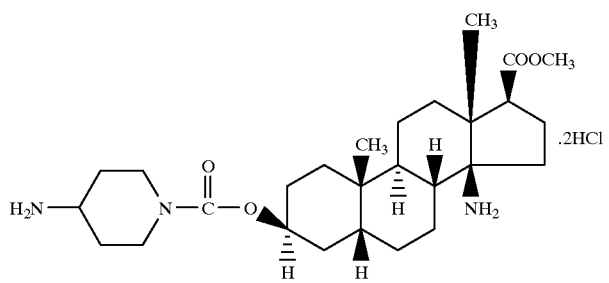

(3β, 5β, 14β, 17β)-14-Amino-3-[[(4-amino-
1-piperedinyl)carbonyl]oxy]androstane-
17-carboxylic Acid, Methyl Ester Dihydrochloride

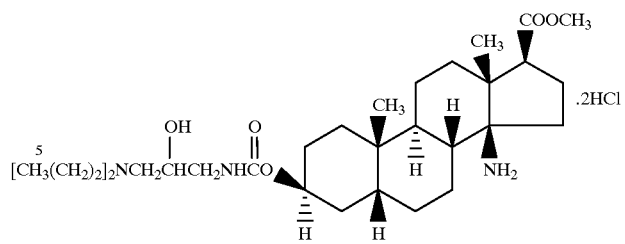

(3β, 5β, 14β, 17β)-14-Amino-3-[[[[3-(dipropylamino)-
2-hydroxypropyl]amino]carbonyl]oxy]androstane-
17-carboxylic Acid, Methyl Ester Dihydrochloride

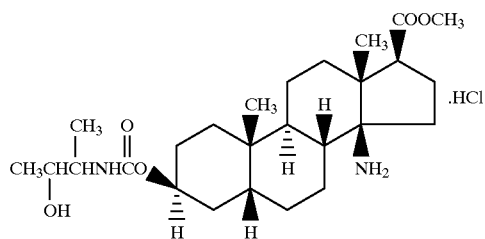

(3β, 5β, 14β, 17β)-14-Amino-3-[[[2-hydroxy-
1-methylpropyl)amino]carbonyl]oxy]androstane-
17-carboxylic Acid, Methyl Ester Hydrochloride

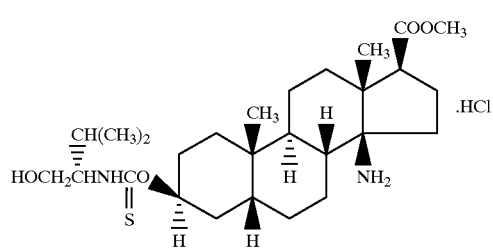

(3β(S), 5β, 14β, 17β)-14-Amino-3-[[[(1-hydroxymethyl-
2-methylpropyl)amino]thioxomethyl]oxy]androstane-
17-carboxylic Acid, Methyl Ester Hydrochloride

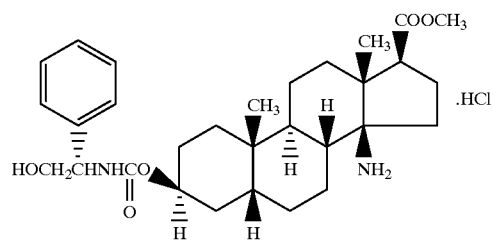

(3β(S), 5β, 14β, 17β)-14-Amino-3-[[[(2-hydroxy-
1-phenylethyl)amino]carbonyl]oxy]androstane-
17-carboxylic Acid, Methyl Ester Hydrochloride

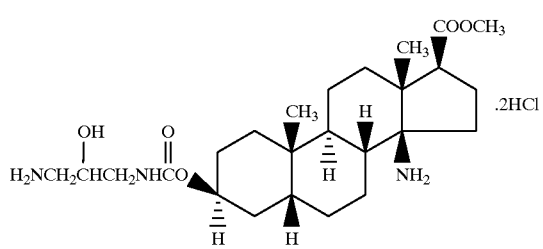

(3β, 5β, 14β, 17β)-14-Amino-3-[[[(3-Amino-
2-hydroxypropyl)amino]carbonyl]oxy]androstane-
17-carboxylic Acid, Methyl Ester Dihydrochloride

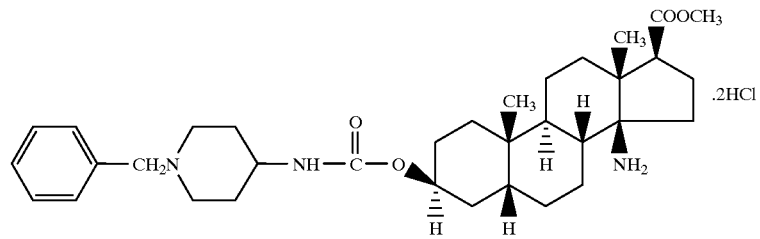

(3β, 5β, 14β, 17β)-14-Amino-3-[[[[1-(phenylmethyl)-
4-piperidinyl]amino]carbonyl]oxy]androstane-
17-carboxylic Acid, Methyl Ester Dihydrochloride

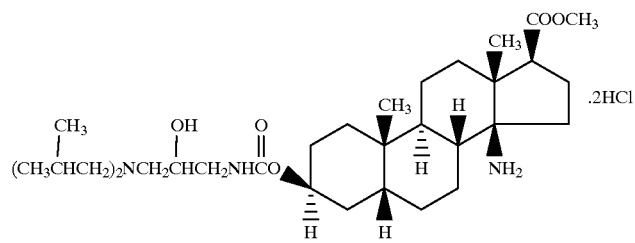

(3β, 5β, 14β, 17β)-14-Amino-3-[[[[3-[bis(2-methylpropyl)-
amino]-2-hydroxypropyl]amino]carbonyl]oxy]androstane-
17-carboxylic Acid, Methyl Ester Dihydrochloride

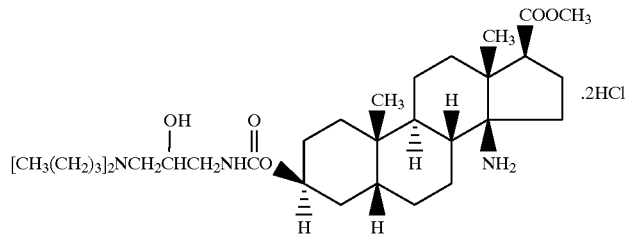

(3β, 5β, 14β, 17β)-14-Amino-3-[[[[3-(dibutylamino))-
2-hydroxypropyl]amino]carbonyl]oxy]androstane-
17-carboxylic Acid, Methyl Ester Dihydrochloride

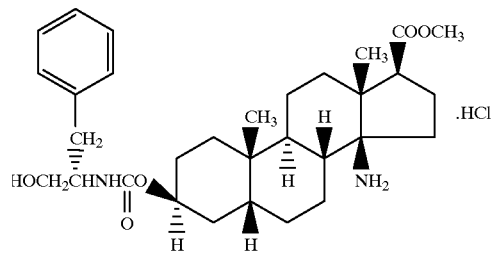

(3β)(S), 5β, 14β, 17β)-14-Amino-3-[[[[2-hydroxy-
1-(phenylmethyl)ethyl]amino]carbonyl]oxy]androstane-
17-carboxylic Acid, Methyl Ester Hydrochloride

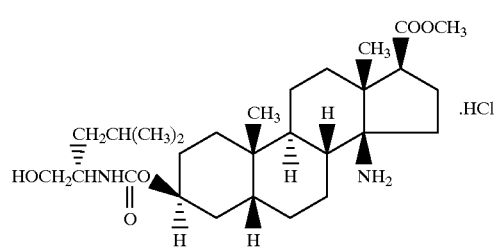

(3β)(S), 5β, 14β, 17β)-14-Amino-3-[[[[(1-hydroxymethyl)-
3-methylbutyl)amino]carbonyl]oxy]androstane-
17-carboxylic Acid, Methyl Ester Hydrochloride

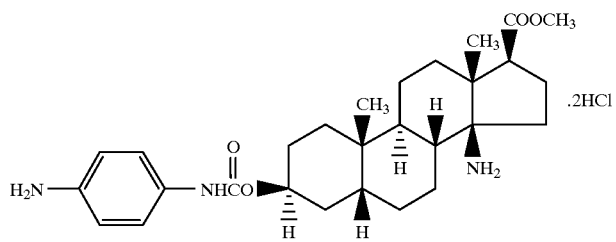

(3β, 5β, 14β, 17β)-14-Amino-3-[[[(4-aminophenyl)amino]-
carbonyl]oxy]androstane-17-carboxylic Acid, Methyl
Ester Dihydrochloride

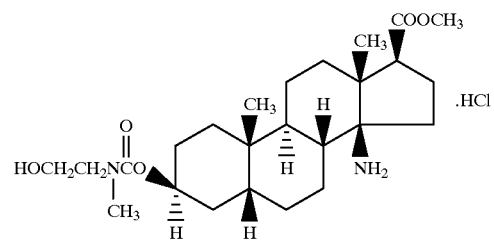

(3β, 5β, 14β, 17β)-14-Amino-3-[[[(2-hydroxyethyl)methyl-
amino]carbonyl]oxy]androstane-17-carboxylic Acid,
Methyl Ester Hydrochloride

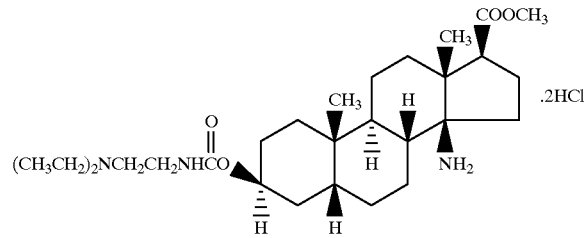

(3β, 5β, 14β, 17β)-14-Amino-3-[[[[2-(diethylamino)ethyl]-
amino]carbonyl]oxy]androstane-17-carboxylic Acid,
Methyl Ester Dihydrochloride -continued

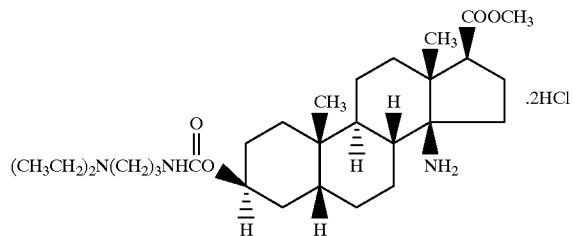

(3β, 5β, 14β, 17β)-14-Amino-3-[[[[3-(diethylamino)propyl]-
amino]carbonyl]oxy]androstane-17-carboxylic Acid,
Methyl Ester Dihydrochloride

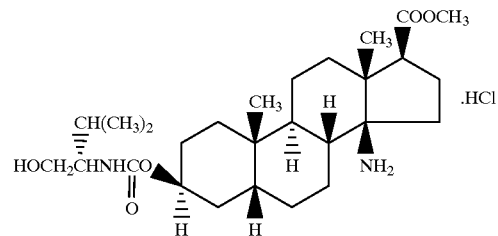

(3β(S), 5β, 14β, 17β)-14-Amino-3-[[[[(1-hydroxymethyl)-
2-methylpropyl]amino]carbonyl]oxy]androstane-
17-carboxylic Acid, Methyl Ester Hydrochloride

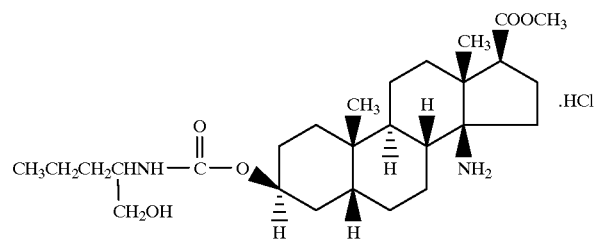

(3β, 5β, 14β, 17β)-14-Amino-3-[[[[(1-hydroxymethyl)-butyl]-
amino]carbonyl]oxy]androstane-17-carboxylic Acid,
Methyl Ester Hydrochloride

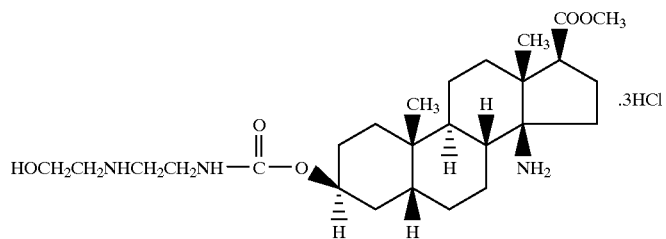

(3β, 5β, 14β, 17β)-14-Amino-3-[[[[2-[2-hydroxyethyl)-
amino]ethyl]amino]carbonyl]oxy]androstane-17-carboxylic
Acid, Methyl Ester Trihyrochloride

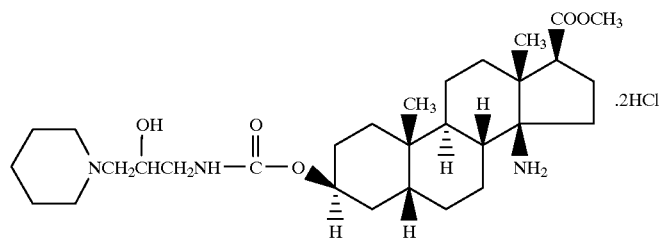

(3β, 5β, 14β, 17β)-14-Amino-3-[[[[2-hydroxy-
3-(1-piperidinyl)propyl]amino]carbonyl]oxy]androstane-
17-carboxylic Acid, Methyl Ester Dihydrochloride

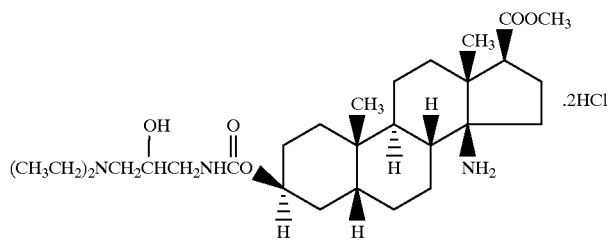

(3β, 5β, 14β, 17β)-14-Amino-3-[[[[(3-diethylamino-
2-hydroxypropyl)amino]carbonyl]oxy]androstane-
17-carboxylic Acid, Methyl Ester Dihyrochloride

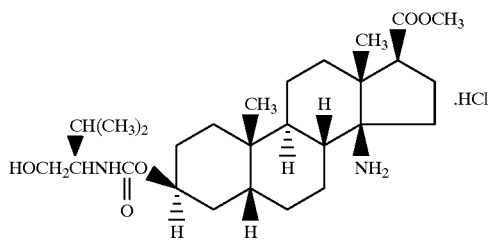

(3β, 5β, 14β, 17β)-14-Amino-3-[[[[1-(hydroxymethyl)-
2-methylpropyl]amino]carbonyl]oxy]androstane-
17-carboxylic Acid, Methyl Ester Hydrochloride

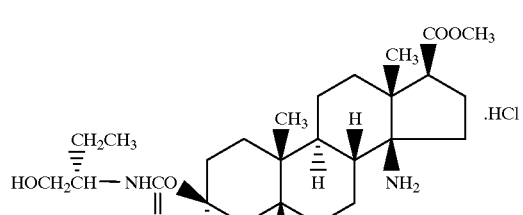

(3β(S), 5β, 14β, 17β)-14-Amino-3-[[[[1-
(hydroxymethyl)propyl]amino]carbonyl]oxy]androstane-
17-carboxylic Acid, Methyl Ester Hydrochloride

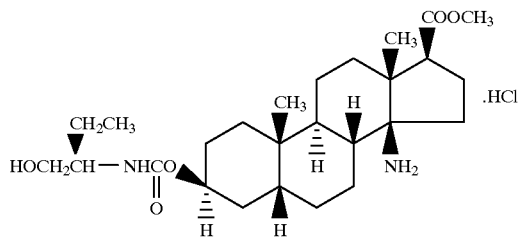

(3β(R), 5β, 14β, 17β)-14-Amino-3-[[[[1-
(hydroxymethyl)propyl]amino]carbonyl]oxy]androstane-
17-carboxylic Acid, Methyl Ester Hydrochloride

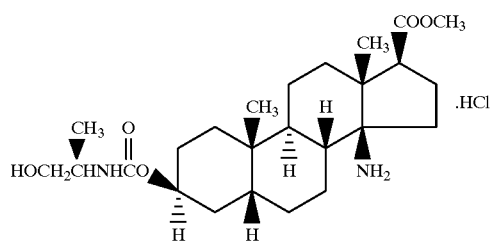

(3β(R), 5β, 14β, 17β)-14-Amino-3-[[[[1-
(hydroxymethyl)ethyl]amino]carbonyl]oxy]androstane-
17-carboxylic Acid, Methyl Ester Hydrochloride -continued

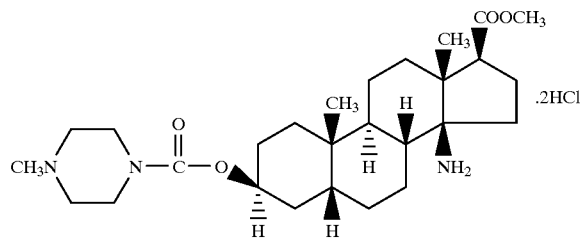

(3β, 5β, 14β, 17β)-14-Amino-3-[[(4-methyl-1-piperazinyl)-
carbonyl]oxy]androstane-17-carboxylic Acid, Methyl
Ester Dihydrochloride

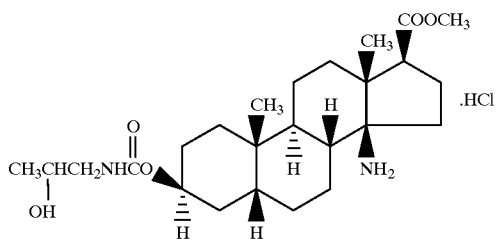

(3β, 5β, 14β, 17β)-14-Amino-3-[[[(2-hydroxypropyl)amino]-
carbonyl]oxy]androstane-17-carboxylic Acid, Methyl
Ester Hydrochloride

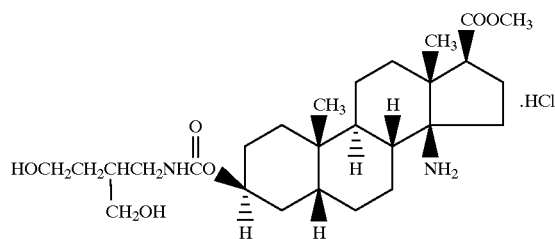

(3β, 5β, 14β, 17β)-14-Amino-3-[[[[4-hydroxy-
2-(hydroxymethyl)butyl]amino]carbonyl]oxy]androstane-
17-carboxylic Acid, Methyl Ester Hydrochloride

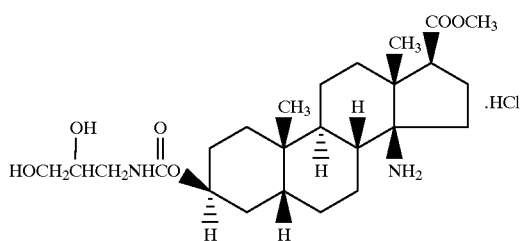

(3β, 5β, 14β, 17β)-14-Amino-3-[[[(2,3-
dihydroxymethyl)amino]carbonyl]oxo]androstane-
17-carboxylic Acid, Methyl Ester Hydrochloride

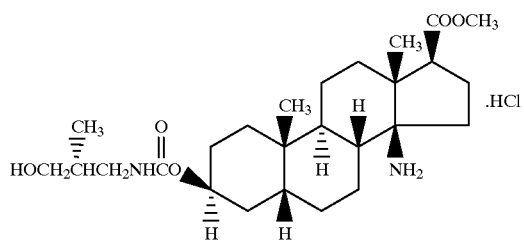

(3β(S), 5β, 14β, 17β)-14-Amino-3-[[[[1-
(hydroxymethyl)ethyl]amino]carbonyl]oxo]androstane-
17-carboxylic Acid, Methyl Ester Hydrochloride

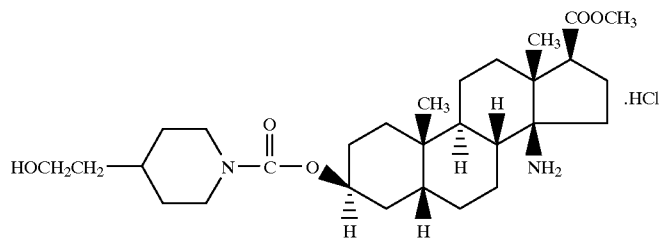

(3β, 5β, 14β, 17β)-14-Amino-3-[[[4-(2-hydroxyethyl)-
1-piperidinyl]carbonyl]oxy]androstane-
17-carboxylic Acid, Methyl Ester Hydrochloride

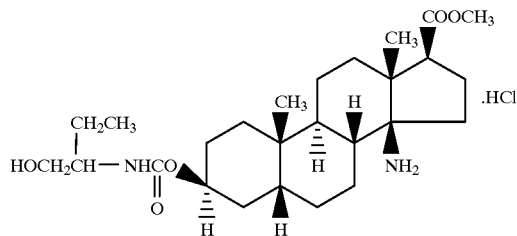

(3β, 5β, 14β, 17β)-14-Amino-3-[[[[1-
(hydroxymethyl)propyl]amino]carbonyl]oxy]androstane-
17-carboxylic Acid, Methyl Ester Hydrochloride

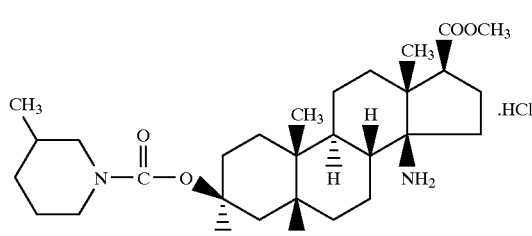

(3β, 5β, 14β, 17β)-14-Amino-3-[[(3-methyl-
1-piperidinyl)carbonyl]oxy]androstane-17-carboxylic
Acid, Methyl Ester Hydrochloride

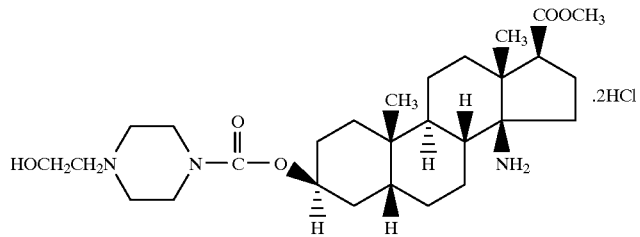

(3β, 5β, 14β, 17β)-14-Amino-3-[[[4-(2-hydroxyethyl)-
1-piperazinyl)carbonyl]oxy]androstane-17-carboxylic
Acid, Methyl Ester Dihydrochloride

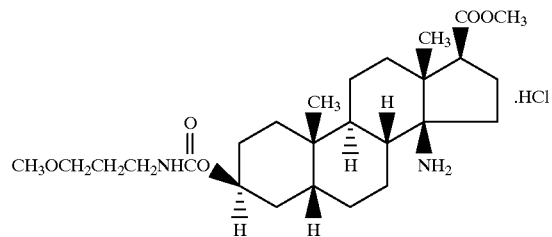

(3β, 5β, 14β, 17β)-14-Amino-3-[[[(3-methoxypropyl)amino]-
carbonyl]oxy]androstane-17-carboxylic Acid, Methyl
Ester Hydrochloride

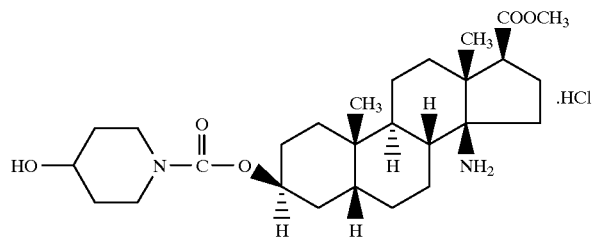

(3β, 5β, 14β, 17β)-14-Amino-3-[[(4-hydroxy-1-piperidinyl)-
carbonyl]oxy]androstane-17-carboxylic Acid, Methyl
Ester Hydrochloride -continued

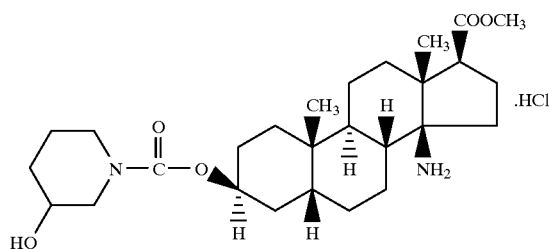

(3β, 5β, 14β, 17β)-14-Amino-3-[[(3-hydroxy-
1-piperidinyl)-carbonyl]oxy]androstane-17-carboxylic
Acid, Methyl Ester Hydrochloride

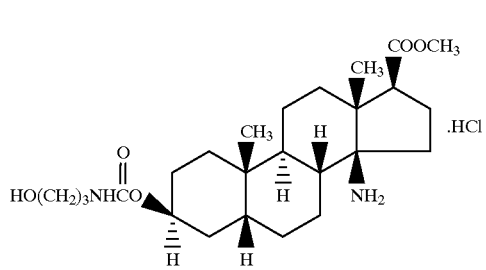

(3β, 5β, 14β, 17β)-14-Amino-3-[[[(3-hydroxypropyl)amino]-
carbonyl]oxy]androstane-17-carboxylic Acid, Methyl
Ester Hydrochloride

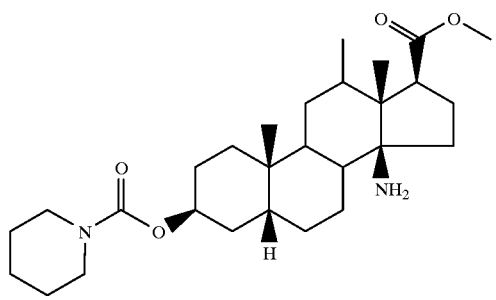

14β-amino-3β-[(1'-piperidinyl)-carbonyloxy]-5β-
androstane-17β-carboxylic acid, methyl ester

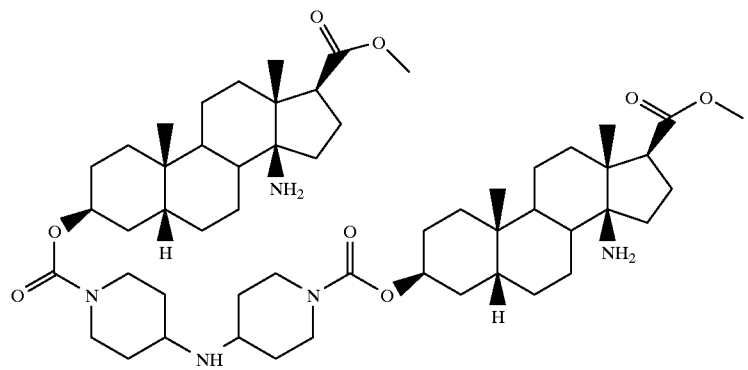

4'-amino-bis[14β-amino-3β-((1'-piperidinyl)-carbonyl-
oxy)-5β-androstane-17β-carboxylic acid, methyl ester]

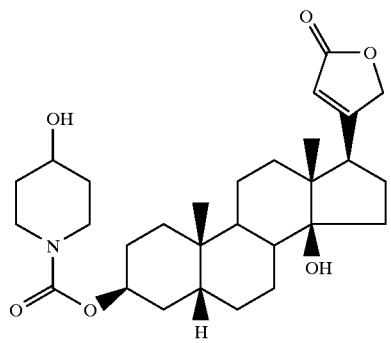

14β-hydroxy-3β-[(4'-hydroxy-1'-piperidinyl)-carbonyl-
oxy]-carden-20(22)-olide

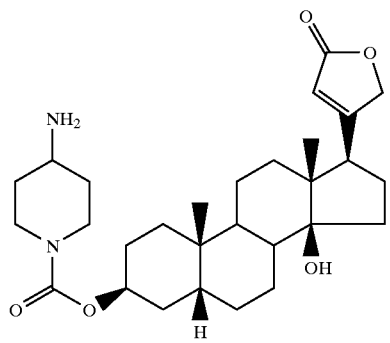

14β-hydroxy-3β-[(4'-amino-1'-piperidinyl)-carbonyl-
oxy]-carden-20(22)-olide

-continued

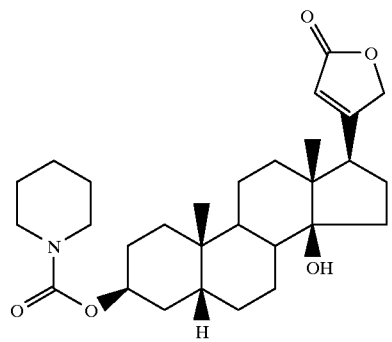

14β-hydroxy-3β-[1'-piperidinyl)-carbonyloxy]-carden-
20(22)-olide

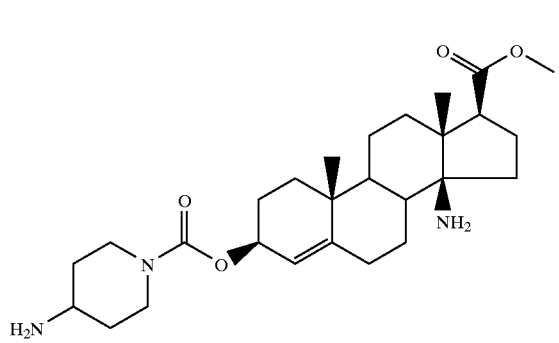

14β-amino-3β-[(4'-amino-1'-piperidinyl)-carbonyloxy]-
4-etienic acid, methyl ester

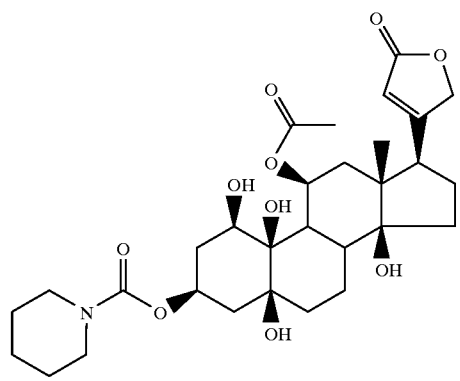

3β-[(1'-piperidinyl)-carbonyloxy]-11-0-acetyl-
ouabaigenine

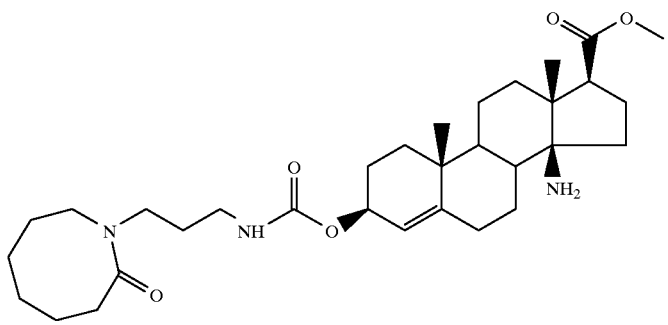

14β-amino-3β-(2"-N-oxo-3'-hexahydroazepinyl-propyl-
aminocarbonyloxy)-4-etienic acid, methyl ester

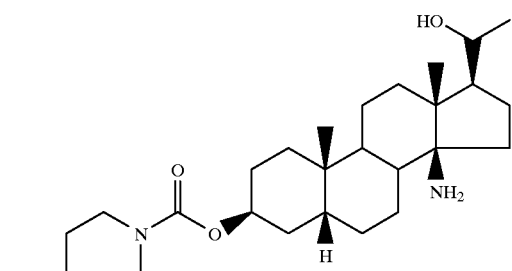

14β-amino-3β-[(4'-hydroxy-1'-piperidinyl)-carbonyloxy]-
20β-hydroxy-pregnane

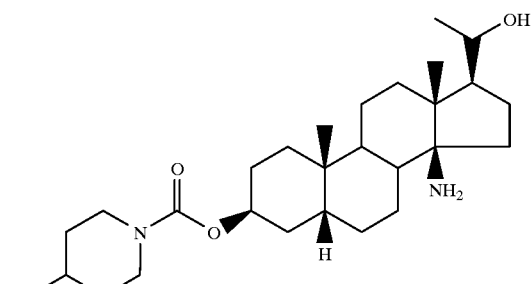

14β-amino-3β-[(4'-hydroxy-1'-piperidinyl)-carbonyloxy]-
20α-hydroxy-pregnane

-continued

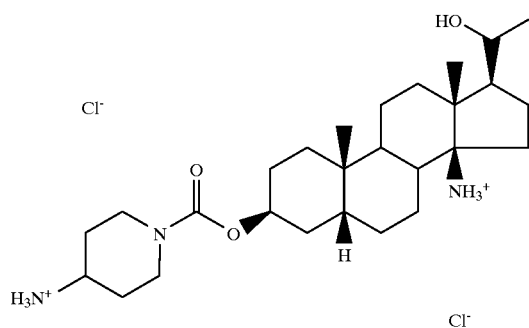

14β-amino-3β-[(4'-hydroxy-1'-piperidinyl)-carbonyl-oxy]-20β-hydroxy-pregnane, dihydrochloride

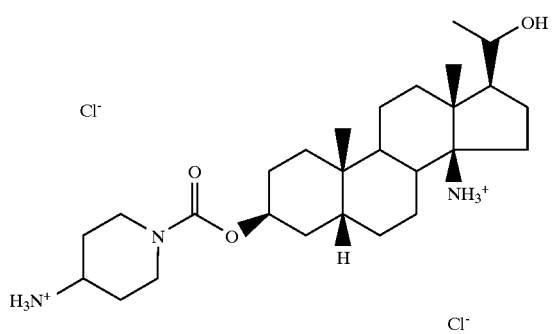

14β-amino-3β-[(4'-hydroxy-1'-piperidinyl)-carbonyloxy]-20β-hydroxy-pregnane, dihydrochloride

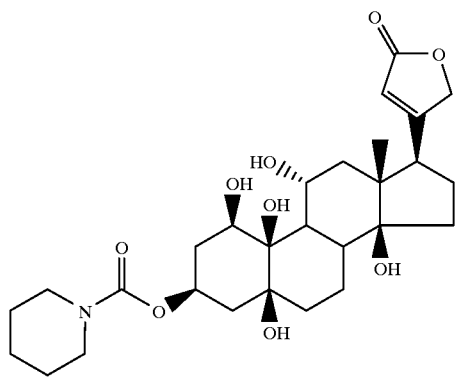

3β-O-(piperidinoformyl)-ouabaigenine

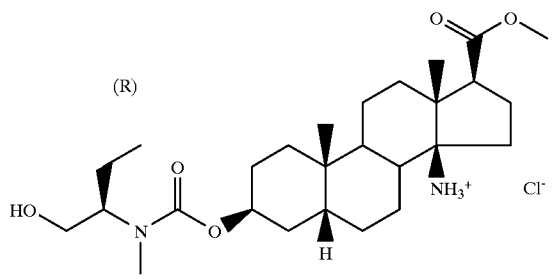

14β-amino-N-methyl-3β-[(R)-1'-hydroxymethyl-propyl-aminoformyloxy)]-5β-androstane-17β-carboxylic acid, methyl ester, hydrochloride

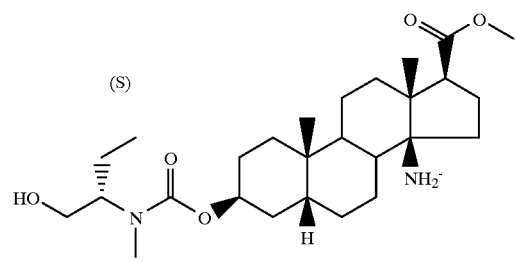

14β-amino-N-methyl-3β-[(S)-1'-hydroxymethyl-propyl-aminoformyloxy)]-5β-androstane-17β-carboxylic acid, methyl ester, hydrochloride

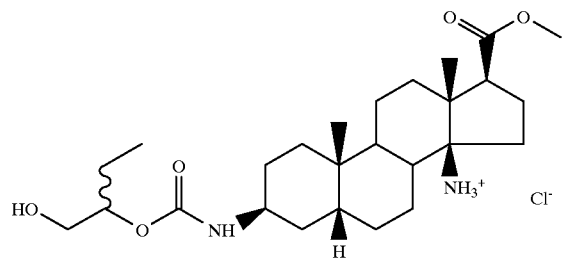

14β-amino-3β-[(Z)-1'-hydroxymethyl-propyloxyformyl-amino)]-5β-androstane-17β-carboxylic acid, methyl ester, hydrochloride

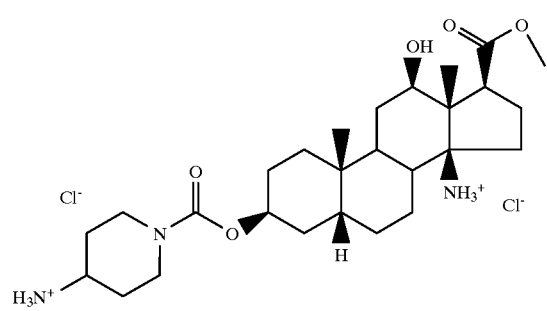

14β-amino-12β-hydroxy-3β-[(4'-amino-1'-piperidinyl)-carbonyloxy]-5β-androstane-17β-carboxylic acid, methyl ester, dihydrochloride

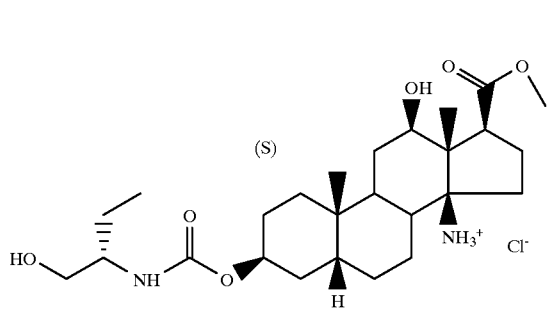

14β-amino-12β-hydroxy-3β-(1'-hydroxymethyl-(S)-propyl)-amino-carbonyloxy]-5β-androstane-17β-carboxylic acid, methyl ester, hydrochloride

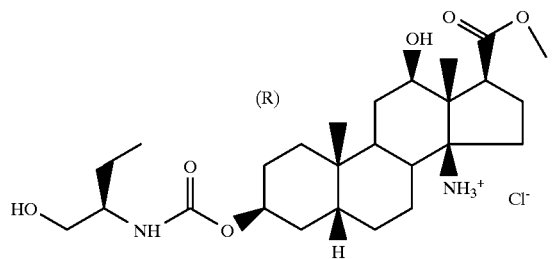

14β-amino-12β-hydroxy-3β-(1'-hydroxymethyl-(R)-propyl)-amino-carbonyloxy]-5β-androstane-17β-carboxylic acid, methyl ester

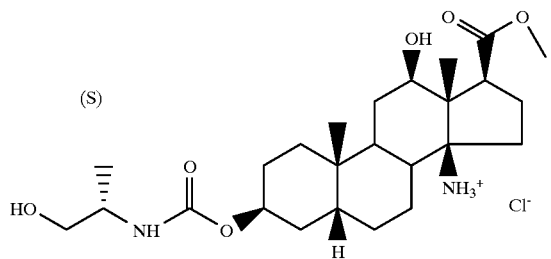

14β-amino-12β-hydroxy-3β-(1'-hydroxymethyl-(S)-methyl)-amino-carbonyloxy]-5β-androstane-17β-carboxylic acid, methyl ester, hydrochloride

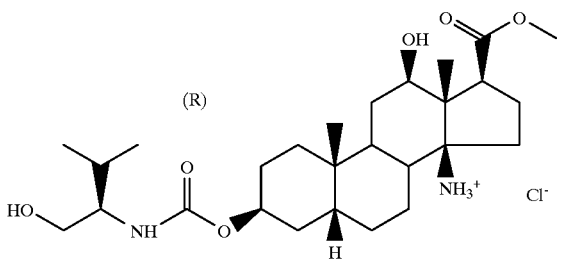

14β-amino-17β-hydroxy-3β-(1'-hydroxymethyl-(R)-2'-methyl-propylamino-carbonyloxy)-5β-androstane-17β-carboxylic acid, methyl ester, hydrochloride

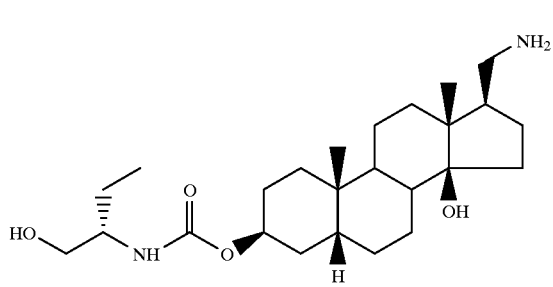

14β-hydroxy-17β-aminomethyl-3β-(1'-hydroxymethyl-(S)-propylamino-carbonyloxy)-5β-androstane

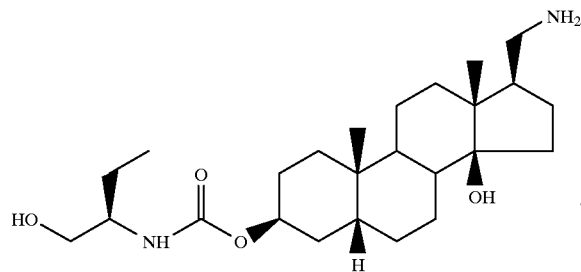

14β-hydroxy-17β-aminomethyl-3β-(1'-hydroxymethyl-(R)-propylamino-carbonyloxy)-5β-androstane

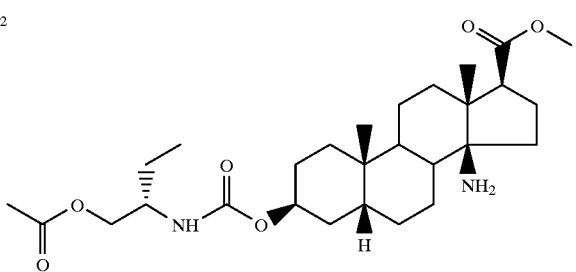

14β-amino-3β-(1'-acetoxymethyl-(S)-propylamino-carbonyloxy)-5β-androstane-17β-carboxylic acid, methyl ester

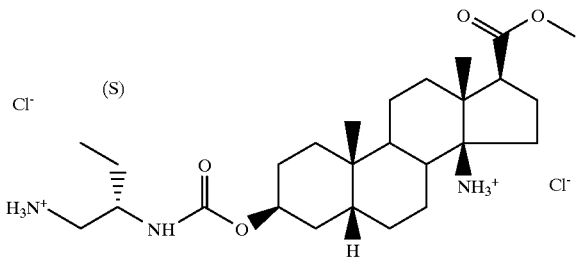

14β-amino-3β-(1'-aminomethyl-(S)-propylamino-carbonyl-oxy)-5β-androstane-17β-carboxylic acid, methyl ester, dihydrochloride -continued

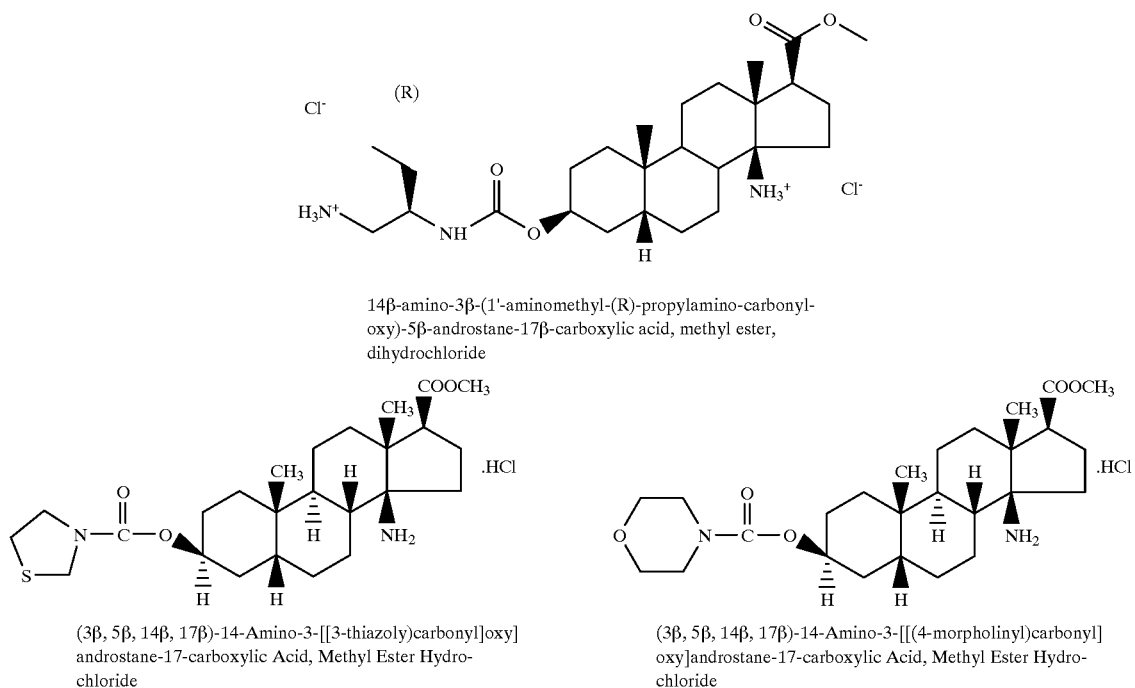

14β-amino-3β-(1'-aminomethyl-(R)-propylamino-carbonyl-oxy)-5β-androstane-17β-carboxylic acid, methyl ester, dihydrochloride (3β, 5β, 14β, 17β)-14-Amino-3-[[3-thiazoly)carbonyl]oxy] androstane-17-carboxylic Acid, Methyl Ester Hydrochloride (3β, 5β, 14β, 17β)-14-Amino-3-[[(4-morpholinyl)carbonyl] oxy]androstane-17-carboxylic Acid, Methyl Ester Hydrochloride

METHODS OF MANUFACTURE

General Procedure

The preparation of the majority of the examples can be described as follows: The aminosteroid aglycone is dissolved in an appropriate solvent at room temperature or with some heating under $N_2$. In most cases methylene chloride is the solvent of choice. Then a 10% excess of 1,1'-carbonyldiimidazole or thiocarbonyldiimidazole is added. The solution is allowed to stir at ambient temperature until no more starting aglycone is detected (via TLC, usually 2 days). Then a 3 to 5 equivalents of the appropriate amine is added and the solution is allowed to stir under ambient temperature or with some heating until TLC indicates no more reaction progress is observed. The solution is then concentrated at reduced pressure and the residue is taken up with fresh methylene chloride. The solution is then washed with water until the washing is neutral to pH paper. After drying over $MgSO_4$, the solvent is removed under reduced pressure and the residue is re-dissolved in a minimum amount of solvent and purified via a silica gel (Merck, Grade 60, 230–240 mesh) column chromatography. The appropriate fractions are collected, combined and concentrated at reduced pressure to give the free base. Treatment of the free base with an ethanolic HCl solution provides the hydrochloride salt.

The compounds of the present invention can be made according to the following non-limiting examples.

EXAMPLE 1

(3β,5β,14β,17β)-14-Amino-3-[[[(3-hydroxypropyl) amino]carbonyl]oxy]androstane-17-carboxylic Acid, Methyl Ester Hydrochloride To a solution of 0.7 g (0.002 mole) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 25 ml of $CH_2Cl_2$ under $N_2$ and stirring, is added 0.36 g (0.0022 mole) of 1,1'-carbonyldiimidazole. After the imidazole intermediate formation is complete (as indicated by TLC, 45 hr), 0.75 g (0.01 mole) of 1-amino-3-propanol is added and the solution is allowed to stir for 4 days. The solution is concentrated and the residue is taken up in fresh $CH_2Cl_2$ and is washed with water until the washing is neutral. After drying over $MgSO_4$, $CH_2Cl_2$ is evaporated under reduced pressure to yield a white sticky solid weighing 680 mg. The solid is dissolved in 7 ml of $CH_2Cl_2$ and is purified through a silica gel column (approx. 3×20 cm) first with 5% MeOH/$CH_2Cl_2$ (with approx. 7 ml of conc. $NH_4OH$) and then with 10% MeOH/$CH_2Cl_2$ (10 ml conc. $NH_4OH$). The fractions are collected, combined and concentrated. The residue is treated with ethanolic HCl to yield the analytically pure (3β,5β,14β,17β)-14-Amino-3-[[[(3-hydroxypropyl)amino]carbonyl]oxy]androstane-17-carboxylic Acid, Methyl Ester Hydrochloride Final Product.

EXAMPLE 2

(3β,5β,14β,17β)-14-Amino-3-[(3-hydroxypiperidinocarbonyl) oxy]androstane-17-carboxylic Acid Methyl Ester Hydrochloride To a solution of 1.40 g (0.004 ml) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 40 ml of $CH_2Cl_2$ under $N_2$ and stirring for ½ hr, is added 0.72 g (0.0044 ml) of 1,1'-carbonyldiimidazole. After 48 hr of stirring at room temperature, 2.02 g (0.020 m) (see NOTE 1) of 3-hydroxypiperidine is added. After 48 hr (see NOTE 2) the slightly cloudy solution is filtered and the filtrate is concentrated at reduced pressure to yield a white sticky solid (see NOTE 3). This white solid residue is redissolved in fresh CH$_2$Cl$_2$ (~40 ml) and this solution is washed with distilled water until the washing is neutral (5×30 ml). After drying over MgSO$_4$, CH$_2$Cl$_2$ is evaporated under reduced pressure to yield 1.77 g of a white solid, TLC (CHCl$_3$.MeOH=9/1 or 8/2) shows essentially 2 spots. The solid is purified by flash chromatography (5% MeOH/CH$_2$Cl$_2$, NH$_4$OH) to yield the analytically pure (3β,5β,14β,17β)-14-Amino-3-[(3-hydroxy-piperidinocarbonyl)oxy] androstane-17-carboxylic Acid Methyl Ester Hydrochloride Final Product.

NOTE 1: The amount of the amine used can be cut down to 3-fold.
NOTE 2: The length of the reaction time varies from 2 to 7 days and should be monitored by TLC.
NOTE 3: This step can be eliminated.

EXAMPLE 3

(3β,5β,14β,17β)-14-Amino-3-[[[(3-methoxypropyl) amino]carbonyl]oxy]androstane-17-carboxylic Acid, Methyl Ester Hydrochloride To a solution of 1.4 g (0.004 mole) of (3β,5β,14β,17β)-14-Amino-14-Amino-3-hydroxyandrostane-17-carboxylic Acid, Methyl Ester, prepared according to the procedure described in U.S. Pat. No. 4,885,280, incorporated by reference herein, in 40 ml of CH$_2$Cl$_2$ under N$_2$ with stirring, is added 0.72 g (0.0044 mole) of 1,1'-carbonyldiimidazole (Aldrich). The mixture is allowed to stir under N$_2$ for 43 hr and then 1.78 g (0.02 mole) of 3-methoxypropylamine is added. The mixture is stirred under N$_2$ at ambient temperature for 4 days. After the solvent is evaporated under reduced pressure, a viscous liquid reside is obtained. This liquid residue is re-dissolved in some fresh CH$_2$Cl$_2$ and the solution is washed with distilled water until the washing is neutral to pH paper. After drying over MgSO$_4$, the solvent is evaporated off to give 1.65 g of white solid. The solid is purified by flash chromatography using silica gel (Merck, 60 grade, 230–240 mesh) and 5% MeOH/CH$_2$Cl$_2$ with 10 ml of conc. NH$_4$OH as eluent. Fractions are collected and the fractions containing the product are combined and evaporated to give a total of 1.15 g of sticky solid. The solid is dissolved in SDA-32 and treated with some EtOH/HCl. After stirring for a short period, the solvent is evaporated to give a viscous liquid. More fresh SDA-32 is added and evaporated again. Then CH$_2$Cl$_2$ is added and evaporated to give a white solid. This process is repeated once more and the residual white solid is dried at 70° to yield the (3β,5β,14β,17β)-14-Amino-14-Amino-3-[[[(3-methoxypropyl) amino]carbonyl]oxy]androstane-17-carboxylic Acid, Methyl Ester Hydrochloride Final Product.

EXAMPLE 4

(3β,5β,14β,17β)-14-Amino-3-[[[[1-(hydroxymethyl) propyl]amino]carbonyl]oxy]androstane-17-carboxylic Acid, Methyl Ester Hydrochloride A mixture of 1.40 g (0.004 mole) of (3β,5β,14β,17β)-14-Amino-14-Amino-3-hydroxyandrostane-17-carboxylic Acid, Methyl Ester, prepared according to the procedure described in U.S. Pat. No. 4,885,280, incorporated by reference herein, in 40 ml of CH$_2$Cl$_2$ is stirred under N$_2$ for ½ hr and then 0.72 g (0.0044 mole) of 1,1'-carbonyldiimidazole is added. The solution is allowed to stir under N$_2$ at ambient temperature for 45 hr. Then 1.78 g (0.02 mole) of 2-amino-1-butanol is added. The mixture is allowed to stir. After 4 days, the solution is concentrated at reduced pressure and the residue, in fresh CH$_2$Cl$_2$, is washed well with distilled water until the washing is neutral to pH paper. After drying over MgSO$_4$, CH$_2$Cl$_2$ is evaporated off to give 1.75 g of white sticky solid. The solid is purified by flash chromatography. The fractions are combined, concentrated and the residue treated with EtOH/HCl. After evaporation of ethanol, the solid residue is re-dissolved in EtOH concentrated again and the residual solid re-dissolved in CH$_2$Cl$_2$ and concentrated. This process is repeated once more and the residual white solid is then dried at 70° to yield the analytically pure (3β,5β,14β,17β)-14-Amino-14-Amino-3-[[[[1-(hydroxymethyl)propyl]amino]carbonyl] oxy]androstane-17-carboxylic Acid, Methyl Ester Hydrochloride Final Product.

EXAMPLE 5

(3β,5β,14β,17β)-14-Amino-3-[[[[4-hydroxy-2-(hydroxymethyl)butyl]amino]carbonyl]oxy] androstane-17-carboxylic Acid, Methyl Ester Hydrochloride A mixture of 1.40 g (0.004 mole) of (3β,5β,14β,17β)-14-Amino-14-Amino-3-hydroxyandrostane-17-carboxylic Acid, Methyl Ester, prepared according to the procedure described in U.S. Pat. No. 4,885,280, incorporated by reference herein, and 0.72 g (0.0044 mole) of 1,1'-carbonyldiimidazole in 40 ml of CH$_2$Cl$_2$ is stirred under N$_2$ for 42 hr. Then 2.38 g (0.02 mole) of 4-hydroxy-2-(hydroxymethyl)-butylamine (0.02 mole) is added. The reaction mixture is allowed to stir under N$_2$ for 5 days. A top oily layer is separated from the CH$_2$Cl$_2$ layer. The solvent is concentrated at reduced pressure to give 3.46 g of a thick liquid. The liquid is diluted with CH$_2$Cl$_2$ and then is washed with H$_2$O until the washing is neutral to pH paper. After drying over MgSO$_4$, the solvent is evaporated to give 1.48 g of white solid. The solid is purified by flash chromatography using 5% MeOH/CH$_2$Cl$_2$ with 10 ml of conc. NH$_4$OH (in 1 liter of solvent) as eluent. Fractions are collected, combined, concentrated and re-chromatographed to yield one portion of (3β,5β,14β,17β)-14-Amino-3-[[[[4-hydroxy-2-(hydroxymethyl)butyl]amino]carbonyl]oxy]androstane-17-carboxylic Acid, Methyl Ester Hydrochloride Final Product with one mole of H$_2$O.

EXAMPLE 6

(3β(R),5β,14β,17β)-14-Amino-3-[[[[1-(hydroxymethyl)ethyl]amino]carbonyl]oxy] androstane-17-carboxylic Acid, Methyl Ester Hydrochloride To a solution of 1.4 g of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 50 ml of CH$_2$Cl$_2$ under N$_2$ and stirring at room temperature after ½ hr, is added 0.72 g (0.044 mole) of 1,1'-carbonyldiimidazole. After 48 hr of stirring, 1.50 g (0.02 mole) of (R)-alaninol is added. The solution is allowed to stir for 5 days and then concentrated at reduced pressure. The residual liquid is diluted with fresh CH$_2$Cl$_2$ and washed with distilled water until the washing is neutral to pH paper. After drying over MgSO$_4$, the solvent is removed under reduced pressure to give a sticky white solid weighing 1.7 g. The solid is purified by flash chromatography with 5% MeOH/CH$_2$Cl$_2$ (with about 10 ml of NH$_4$OH/1 liter of solvent) as eluent. The fractions containing one single spot of the product were combined and concentrated at reduced pressure to give 1.15 g of a white solid. Treatment with ethanolic HCl and concentration of solvent, followed by washing once with SDA and twice with $CH_2Cl_2$ yields the $(3\beta(R),5\beta,14\beta,17\beta)$-14-Amino-3-[[[[1-(hydroxymethyl) ethyl]-amino]carbonyl]oxy]androstane-17-carboxylic Acid, Methyl Ester Hydrochloride Final Product.

EXAMPLE 7

$(3\beta(R),5\beta,14\beta,17\beta)$-14-Amino-3-[[[1-(hydroxymethyl)propyl]amino]carbonyl]oxy]androstane-17-carboxylic Acid, Methyl Ester Hydrochloride To a solution of 1.4 g (0.004 mole) of $(3\beta,5\beta,14\beta,17\beta)$-14-Amino-3-hydroxyandrostane-17-carboxylic Acid, Methyl Ester, prepared according to the procedure described in U.S. Pat. No. 4,885,280, incorporated by reference herein, in 50 ml of $CH_2Cl_2$ under $N_2$ at room temperature under stirring for ½ hr, is added 0.72 g (0.044 mole) of 1,1-carbonyldiimidazole. After 48 hr of stirring, 1.78 g (0.02 mole) of (R)-2-amino-1-butanol is added and the solution is allowed to stir. After 5 days, the reaction solution is worked up the same way as in Example 6. The yield of the crude free base is 1.7 g. The solid is purified by gravitational column chromatography (silica gel, 230–240 mesh, 5% $MeOH/CH_2Cl_2$, $NH_4OH$) to yield 1.15 g of a white solid. Treatment with EtOH/HCl and working up the same way as in Example 6 yields $(3\beta(R),5\beta,14\beta,17\beta)$-14-Amino-3-[[[1-(hydroxymethyl)propyl]amino]carbonyl]oxy]androstane-17-carboxylic Acid, Methyl Ester Hydrochloride Final Product.

EXAMPLE 8

$(3\beta(S),5\beta,14\beta,17\beta)$-14-Amino-3-[[[1-(hydroxymethyl)propyl]amino]carbonyl]oxy]androstane-17-carboxylic Acid, Methyl Ester Hydrochloride To a solution of 1.4 g (0.004 mole) of $(3\beta,5\beta,14\beta,17\beta)$-14-Amino-3-hydroxyandrostane-17-carboxylic Acid, Methyl Ester, prepared according to the procedure described in U.S. Pat. No. 4,885,280, incorporated by reference herein, in 50 ml of $CH_2Cl_2$ under $N_2$ at room temperature under stirring is added 0.72 g (0.044 mole) of 1,1'-carbonyldiimidazole. The reaction mixture is allowed to stir under $N_2$ for 2 days and then 1.78 g (0.02 mole) of (S)-2-amino-1-butanol is added. After 4 days of stirring, the reaction is worked up the same way as in Example 7. The yield of the free base after flash chromatography is 1.15 g. It is converted to its HCl salt by the usual work up to yield $(3\beta(S),5\beta,14\beta,17\beta)$-14-Amino-14-Amino-3-[[[1-(hydroxymethyl)propyl]amino]carbonyl]oxy]androstane-17-carboxylic Acid, Methyl Ester Hydrochloride Final Product.

EXAMPLE 9

$(3\beta(R),5\beta,14\beta,17\beta)$-14-Amino-3-[[[1-(hydroxymethyl)-2-methylpropyl]amino]carbonyl]oxy]androstane-17-carboxylic Acid, Methyl Ester Hydrochloride To a solution of 1.4 g (0.004 mole) of $(3\beta,5\beta,14\beta,17\beta)$-14-Amino-3-hydroxyandrostane-17-carboxylic Acid, Methyl Ester, prepared according to the procedure described in U.S. Pat. No. 4,885,280, incorporated by reference herein, in 50 ml of $CH_2Cl_2$ under $N_2$ at room temperature under stirring is added 0.72 g (0.0044 mole) of 1,1'-carbonyldiimidazole. After 2 days, 2.06 g (0.02 mole) of R-(-)-2-amino-3-methyl-1-butanol is added. The mixture is allowed to stir at ambient temperature under $N_2$ for 5 days and worked up the same way as in Example 8. Purification by flash chromatography (5% $MeOH/CH_2Cl_2$, $NH_4OH$) gave 1.0 g of a sticky solid. The solid is converted to its hydrochloride salt by treatment with ethanolic HCl followed by washings with SDA-32 and $CH_2Cl_2$. To yield analytically pure $(3\beta(R),5\beta,14\beta,17\beta)$-14-Amino-3-[[[1-(hydroxymethyl)-2-methylpropyl]amino]carbonyl]oxy]androstane-17-carboxylic Acid, Methyl Ester Hydrochloride Final Product.

EXAMPLE 10

$(3\beta,5\beta,14\beta,17\beta)$-14-Amino-3-[[[(3-diethylamino-2-hydroxypropyl)amino]carbonyl]oxy]androstane-17-carboxylic Acid, Methyl Ester Dihydrochloride To a solution of 1.4 g (0.004 mole) of $(3\beta,5\beta,14\beta,17\beta)$-14-Amino-3-hydroxyandrostane-17-carboxylic Acid, Methyl Ester, prepared according to the procedure described in U.S. Pat. No. 4,885,280, incorporated by reference herein, in 40 ml of $CH_2Cl_2$ under $N_2$ at room temperature under stirring is added 0.72 g (0.0044 mole) of 1,1'-carbonyldiimidazole. After 2 days, 2.92 g (0.02 mole) of 1-amino-3-diethylamino-2-propanol is added. The solution turned somewhat cloudy. After 3 days of stirring under $N_2$ at room temperature, the mixture is worked up the same way as in Example 8. The crude solid (1.8 g) is purified by flash chromatography (5% $MeOH/CH_2Cl_2$, $NH_4OH$) to yield a sticky solid. Treatment with ethanolic HCl yields $(3\beta,5\beta,14\beta,17\beta)$-14-Amino-3-[[[(3-diethylamino-2-hydroxypropyl)amino]carbonyl]oxy]androstane-17-carboxylic Acid, Methyl Ester Dihydrochloride Final Product.

EXAMPLE 11

$(3\beta(S),5\beta,14\beta,17\beta)$-14-Amino-3-[[[[(1-hydroxymethyl)-2-methylpropyl]amino]carbonyl]oxy]androstane-17-carboxylic Acid, Methyl Ester Hydrochloride To a solution of 1.40 g (0.004 mole) of $(3\beta,5\beta,14\beta,17\beta)$-14-Amino-3-hydroxyandrostane-17-carboxylic Acid, Methyl Ester, prepared according to the procedure described in U.S. Pat. No. 4,885,280, incorporated by reference herein, in 50 ml of $CH_2Cl_2$ under $N_2$ and stirring for ½ hr, is added 0.72 g (0.0044 mole) of 1,1'-carbonyldiimidazole. After 48 hr of stirring at room temperature, 1.05 g (0.020 mole) of S-(-)-2-amino-3-methyl-1-butanol is added. After 3 days of stirring, TLC indicates the presence of the imidazole intermediate. Another 1.05 g of the amine is added and the mixture is allowed to stir further. After another 5 days, the reaction solution is concentrated and the residue is taken up with fresh $CH_2Cl_2$ and washed well with water until the washing is neutral. After drying over $MgSO_4$, $CH_2Cl_2$ is removed under reduced pressure to give 1.6 g of crude free base which is purified via flash chromatography using 5% $MeOH/CH_2Cl_2$ ($NH_4OH$). The fractions containing the majority of the product are combined and concentrated at reduced pressure to yield the free base which is converted to its hydrochloride salt by treatment with ethanolic HCl solution and drying at 70° to yield analytically pure $(3\beta(S),5\beta,14\beta,17\beta)$-14-Amino-3-[[[[(1-hydroxymethyl)-2-methylpropyl]amino]carbonyl]oxy]androstane-17-carboxylic Acid, Methyl Ester Hydrochloride Final Product.

EXAMPLE 12

$(3\beta,5\beta,14\beta,17\beta)$-14-Amino-3-[[[3-(diethylamino)propyl]amino]carbonyl]oxy]androstane-17-carboxylic Acid, Methyl Ester Dihydrochloride To a solution of 1.4 g (0.004 mole) of $(3\beta,5\beta,14\beta,17\beta)$-14-Amino-3-hydroxyandrostane-17-carboxylic Acid, Methyl Ester, prepared according to the procedure described in U.S. Pat. No. 4,885,280, incorporated by reference herein, in 50 ml of $CH_2Cl_2$ under $N_2$ at room temperature, is added 0.72 g (0.0044 mole) of 1,1'-carbonyldiimidazole. After 2 days of stirring under room temperature, 2.6 g (0.02 mole) of 3-diethylaminopropylamine is added. The solution is allowed to stir at ambient temperature and is then concentrated and the residue is taken up with fresh $CH_2Cl_2$ and is washed well with water until the washing is neutral. After drying over $MgSO_4$, $CH_2Cl_2$ is removed under reduced pressure to yield 1.68 g of crude sticky solid. The solid is purified via flash chromatography twice to yield the free base. Treatment with ethanolic HCl yields two crops of (3β,5β,14β,17β)-14-Amino-3-[[[[3-(diethylamino)propyl]amino]carbonyl]oxy]androstane-17-carboxylic Acid, Methyl Ester Dihydrochloride Final Product.

EXAMPLE 13

(3β,5β,14β,17β)-14-Amino-3-[[[[2-(diethylamino)ethyl]amino]carbonyl]oxy]androstane-17-carboxylic Acid, Methyl Ester Dihydrochloride To a solution of 1.4 g (0.004 mole) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 50 ml of $CH_2Cl_2$ under $N_2$ and stirring, is added 0.72 g (0.0044 mole) of 1,1'-carbonyldiimidazole. The mixture is allowed to stir for 2 days, then 2.24 g (0.02 mole) of N,N-diethylethylenediamine is added. After 48 hr of stirring, the solution is concentrated and the residue is taken up with fresh $CH_2Cl_2$ and is washed well with water until the washing is neutral. After drying over $MgSO_4$, $CH_2Cl_2$ is removed under reduced pressure to yield 1.55 g of crude free base. Purification via flash chromatography using 3% $MeOH/CH_2Cl_2$ ($NH_4OH$) at first, followed by 4% and then 7% $MeOH/CH_2Cl_2$ provides the free base. Treatment with ethanolic HCl yields the analytically pure (3β,5β,14β,17β)-14-Amino-3-[[[[2-(diethylamino)ethyl]amino]carbonyl]oxy]androstane-17-carboxylic Acid, Methyl Ester Dihydrochloride Final Product.

EXAMPLE 14

(3β(S),5β,14β,17β)-14-Amino-3-[[[f(1-hydroxymethyl)-3-methylbutyl]aminolcarbonyl]oxy]androstane-17-carboxylic Acid, Methyl Ester Hydrochloride To a solution of 1.4 g (0.004 mole) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 40 ml of $CH_2Cl_2$ under $N_2$ and stirring, is added 0.72 g (0.0044 mole) of 1,1'-carbonyldiimidazole. The solution is allowed to stir for 2 days and then 2.34 g (0.02 mole) of (S)-(+)-leucinol is added. The solution is allowed to stir for 4 days and is then heated at reflux temperature overnight. The solvent is removed and the residue is taken up with fresh $CH_2Cl_2$ and is washed well with water until the washing is neutral. After drying over $MgSO_4$, $CH_2Cl_2$ is removed under reduced pressure to yield the crude free base which is purified via flash chromatography and treated with ethanolic HCl to yield the analytically pure (3β(S),5β,14β,17β)-14-Amino-3-[[[[(1-hydroxymethyl)-3-methyl-butyl]amino]carbonyl]oxy]androstane-17-carboxylic Acid, Methyl Ester Hydrochloride Final Product.

EXAMPLE 15

(3β,5β,14β,17β)-14-Amino-3-[[[[2-hydroxy-1-(phenylmethyl)ethyl]amino]carbonyl]oxy]androstane-17-carboxylic Acid, Methyl Ester Hydrochloride To a solution of 1.4 g (0.004 mole) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 40 ml of $CH_2Cl_2$ under $N_2$ and stirring, is added 0.72 g (0.0044 mole) of 1,1'-carbonyldiimidazole. The solution is allowed to stir for 2 days and then 1.8 g (0.012 mole) of (S)-2-amino-3-phenyl-1-propanol is added. No product appeared to form (TLC) after 3 days of stirring and an additional 0.6 g (0.004 mole) of the amine is added and the solution is heated at boiling for 2 days. After cooling to ambient temperature, the solution is allowed to stir further for an additional 10 days. The solution is concentrated at reduced pressure and the residue is taken up with fresh $CH_2Cl_2$. The solution is washed with water until the washing is neutral. After drying over $MgSO_4$, $CH_2Cl_2$ is removed under reduced pressure and the residual solid is purified by flash chromatography (5% $MeOH/CH_2Cl_2$, $NH_4OH$). The fractions are combined and concentrated to yield the free base which is treated with ethanolic HCl to yield (3β(S),5β,14β,17β)-14-Amino-3-[[[[2-hydroxy-1-(phenylmethyl)ethyl]amino]carbonyl]oxy]androstane-17-carboxylic Acid, Methyl Ester Hydrochloride Final Product.

EXAMPLE 16

(3β,5β,14β,17β)-14-Amino-3-[[[(3-amino-2-hydroxypropyl)amino]carbonyl]oxy]androstane-17-carboxylic Acid, Methyl Ester Dihydrochloride To a solution of 1.4 g (0.004 mole) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 40 ml of $CH_2Cl_2$ under $N_2$ and stirring, is added 0.72 9 (0.0044 mole) of 1,1'-carbonyldiimidazole. The solution is allowed to stir for 2 days and then 1.8 g (0.020 mole) of 1,3-diamino-2-hydroxypropane in 25 ml of $CH_2Cl_2$ is added. The mixture is heated at reflux for 3 days and is filtered to get rid of some solid that is forming around the neck of the flask. The filtrate is washed well with water until the washing is neutral (approximately 20 times). After drying over $MgSO_4$, $CH_2Cl_2$ is removed under reduced pressure to yield 1.15 g of a white solid. The solid is purified by flash chromatography using 10% $MeOH/CH_2Cl_2$ ($NH_4OH$). The fractions are combined and are concentrated to yield a viscous liquid. Treatment with ethanolic HCl yields analytically pure (3β,5β,14β,17β)-14-Amino-3-[[[(3-amino-2-hydroxypropyl)amino]carbonyl]oxy]androstane-17-carboxylic Acid, Methyl Ester Dihydrochloride Final Product.

EXAMPLE 17

(3β,5β,14β,17β)-14-Amino-3-[[[(2-hydroxy-1-phenylethyl)amino]carbonyl]oxy]androstane-17-carboxylic Acid, Methyl Ester Hydrochloride To a solution of 1.4 g (0.004 mole) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 50 ml of $CH_2Cl_2$ under $N_2$ and stirring, is added 0.72 g (0.0044 mole) of 1,1'-carbonyldiimidazole. After 2 days 2.74 g (0.02 mole) of S-2-phenylglycinol is dissolved in a minimum amount of $CH_2Cl_2$ and is added to the reaction mixture. The reaction mixture is heated at reflux for 4 days and another 0.54 g (0.004 mole) of (S)-2-phenylglycinol is added. The mixture is heated further at reflux temperature for 6 days. The solution is concentrated at reduced pressure and the residue is taken up with fresh $CH_2Cl_2$, is washed well with H₂O until the washing is neutral. After drying over MgSO₄, CH₂Cl₂ is removed under reduced pressure to yield the crude free base. The solid is purified by flash chromatography (5% MeOH/CH₂Cl₂, NH₄OH) and then converted to its hydrochloride salt by the treatment with ethanolic HCl. Two crops of (3β(S),5β,14β,17β)-14-Amino-3-[[[(2-hydroxy-1-phenylethyl)amino]carbonyl]oxy]androstane-17-carboxylic Acid, Methyl Ester Hydrochloride Final Product are obtained.

EXAMPLE 18

(3β,5β,14β,17β)-14-Amino-3-[[[(l-hydroxymethyl-2-methylpropyl)amino]thioxomethyl]oxy]androstane-17-carboxylic Acid, Methyl Ester Hydrochloride To a solution of 1.4 g (0.004 mole) of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, in 50 ml of CH₂Cl₂ under N₂ and stirring, 0.78 g (0.0044 mole) of 1,1'-thiocarbonyldiimidazole is added. After 2 days of stirring at ambient temperature, the solution is heated at reflux overnight and an additional 0.16 g (0.0009 mole) of 1,1'-thiocarbonyldiimidazole is added. The solution is allowed to stir further at ambient temperature for 3 days; then 2.06 g (0.02 mole) of (S)-2-amino-3-methyl-1-butanol is added to the reaction mixture. The solution is allowed to stir for another 3 days and the solvent is then removed under reduced pressure. The residue is taken up in fresh CH₂Cl₂, washed with H₂O until the washing is neutral. After drying over MgSO₄, CH₂Cl₂ is removed under reduced pressure to yield the crude free base. The solid is purified by flash chromatography and then converted to its hydrochloride salt by the treatment with ethanolic HCl to yield analytically pure (3β(S),5β,14β,17β)-14-Amino-14-Amino-3-[[[(l-hydroxymethyl-2-methylpropyl)amino]thioxomethyl]oxy]androstane-17-carboxylic Acid, Methyl Ester Hydrochloride Final Product.

EXAMPLE 19

(3β,5β,14β,17β)-3-[[[3-(Acetyloxy)-1-piperidinyl]carbonyl]oxy]-14-aminoandrostane-17-carboxylic Acid, Methyl Ester Hydrochloride A solution of 1.0 g (0.002 mole) of the free base of (3β,5β,14β,17β)-14-Amino-3-[(3-hydroxypiperidinocarbonyl)oxy]-androstane-17-carboxylic Acid Methyl Ester Hydrochloride, in 30 ml of CH₂Cl₂, 5 ml of acetic anhydride and a few drops of glacial acetic acid is heated at reflux for 4 days. After another day of standing at room temperature, the solution is concentrated at reduced pressure to give 0.95 g of solid. The solid is purified via flash chromatography (5% MeOH/CH₂Cl₂, NH₄OH) to yield the free base which is converted to the hydrochloride salt of the Final Product, (3β,5β,14β,17β)-3-[[[3-(Acetyloxy)-1-piperidinyl]carbonyl]oxy]-14-aminoandrostane-17-carboxylic Acid, Methyl Ester Hydrochloride by treating with ethanolic HCl.

EXAMPLE 20

(3β(S),5β,14β,17β)-14-Amino-3-[[[(2-hydroxy-1-phenylethyl)amino]carbonyl]oxy]-N-methylandrostane-17-carboxamide Hydrochloride To a solution of 800 mg (0.0023 mole) of (3β,5β,14β, 17β)-14-Amino-3-hydroxy-N-methylandrostane-17-carboxamide, Hydrochloride, free base in 100 ml of CH₂Cl₂ under N₂ and stirring, is added 0.41 g (0.0025 mole) of 1,1'-carbonyldiimidazole. The solution is allowed to stir until no starting material is present as determined by TLC. Then 1.58 g (0.012 mole) of (S)-phenyl-glycinol is added. The solution is heated at reflux for 6 days and CH₂Cl₂ is distilled off and 35 ml of benzene is introduced. The solution is heated to boiling for 1 hr and is then allowed to cool. The solvent is removed and the residue is taken up in fresh CH₂Cl₂. The CH₂Cl₂ solution is washed with water until the washing is neutral. After drying over MgSO₄, CH₂Cl₂ is removed under reduced pressure and the residual beige colored solid, (0.66 g) is purified via column chromatography. The fractions are combined and concentrated to give a total of 470 mg of solid. A portion of this solid is converted to its hydrochloride salt by the treatment with ethanolic HCl. The solid is dried at 77° under vacuum for 5 days to yield the analytically pure (3β(S),5β,14β,17β)-14-Amino-3-[[[(2-hydroxy-1-phenylethyl)amino]carbonyl]oxy]-N-methylandrostane-17-carboxamide Hydrochloride Final Product.

EXAMPLE 21

(3β,5β,14β,17β)-14-Amino-3-[[(3-hydroxy-1-piperidinyl)carbonyl]oxy]N-methylandrostane-17-carboxamide Hydrochloride A mixture of 2.08 g (0.006 mole) of the free base of (3β,5β,14β,17β)-14-Amino-3-hydroxy-N-methylandrostane-17-carboxamide, Hydrochloride, incorporated by reference herein, in 750 ml of CH₂Cl₂ is heated at reflux for 6 hr. The insoluble material is filtered off. To the filtrate under N₂ and stirring is added 0.98 g (0.006 mole) of 1,1'-carbonyldiimidazole. The solution is allowed to stir at ambient temperature overnight and then the volume of the solution is decreased to one-half by distillation. The remaining solution is heated at reflux for 2 days and an additional 0.54 g (0.004 mole) of 1,1'-carbonyldiimidazole is added. After another 7 hr of heating, TLC shows a single spot. 2.78 g (0.03 mole) of 3-hydroxypiperidine is then added. The solution is heated at reflux for 4 days. A viscous oil formed at the top and the layers are separated. The CH₂Cl₂ layer is washed well with H₂O until the washing is neutral. After drying over MgSO₄, CH₂Cl₂ is removed under reduced pressure to yield 320 mg of solid (3β,5β,14β,17β)-14-Amino-3-[[(3-hydroxy-1-piperidinyl) carbonyl]oxy]N-methylandrostane-17-carboxamide. This solid is converted to its hydrochloride salt Final Product by treatment with ethanolic HCl. The oily layer is diluted with water and extracted with CH₂Cl₂. The CH₂Cl₂ extract is also dried over MgSO₄ and concentrated at reduced pressure to yield additional (3β,5β,14β,17β)-14-Amino-3-[[(3-hydroxy-1-piperidinyl)carbonyl]oxy]N-methylandrostane-17-carboxamide Hydrochloride.

EXAMPLE 22

(3β,5β,14β,17β)-14-Amino-3-[[(4-hydroxy-1-piperidinyl)carbonyl]oxy]androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.03 g, 2.95 mmole) in 25 ml of CH₂Cl₂ under a N₂ blanket is treated with carbonyldiimidazole (0.58 g, 3.55 mmole). The mixture is stirred at room temperature for 2 days to yield the imidazole intermediate. The reaction intermediate is not isolated but is treated directly with 4-hydroxypiperidine (1.49 g, 14.75 mmole).

The reaction is continued stirring at room temperature under nitrogen for 1 day. The reaction mixture is filtered and the filtrate concentrated under reduced pressure to yield an oily residue. The residue is chromatographed on silica gel packed column with 7% MeOH/93% $CH_2Cl_2$ containing 1% $NH_4OH$ to yield pure product as the free base. The product is prepared by dissolving the free base in absolute alcohol followed by the addition of saturated ethanolic/HCl with stirring. The alcoholic solution is concentrated under reduced pressure to leave an oily residue. The oily residue is flushed with 4×50 ml of $CH_2Cl_2$ to yield analytically pure (3β,5β,14β,17β)-14-Amino-3-[[(4-hydroxy-1-piperidinyl) carbonyl]oxy]androstane-17-carboxylic Acid, Methyl Ester Hydrochloride Final Product.

EXAMPLE 23

(3β,5β,14β,17β)-14-Amino-3-[[[4–2-hydroxyethyl)- 1-piperazinyl) carbonyl]oxy]androstane-17- carboxylic Acid, Methyl Ester Dihydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.03 g, 2.95 mmole) in 25 ml of $CH_2Cl_2$ under a $N_2$ blanket is treated with 1,1'-carbonyldiimidazole (0.58 g, 3.55 mmole). The mixture is stirred at room temperature for 24 hours and then treated with 4-hydroxyethyl-piperazine (1.92 g, 14.75 mmole). The reaction is continued to be stirred at room temperature under nitrogen overnight. The reaction solution is concentrated under reduced pressure and the residue is taken up in fresh $CH_2Cl_2$. The $CH_2Cl_2$ solution is washed with 4×25 ml portions of water. The organic layer is dried over anhydrous $Na_2SO_4$ and filtered. The filtrate is concentrated under reduced pressure to leave an oily residue weighing 0.94 g. The crude free base is purified by chromatography on silica gel packed column with an eluent of 5% MeOH/95% $CH_2Cl_2$ containing 1% $NH_4OH$. The pure free base is dissolved in absolute alcohol and then treated with saturated ethanolic/HCl to yield (3β,5β,14β,17β)-14-Amino-3-[[[4–2-hydroxyethyl)-1-piperazinyl)carbonyl] oxy]androstane-17-carboxylic Acid, Methyl Ester Dihydrochloride Final Product.

EXAMPLE 24

(3β,5β,14β,17β)-14-Amino-3-[[(3-methyl-1- piperidinyl)carbonyl]oxy]androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.03 g, 2.95 mmole) in 25 ml of $CH_2Cl_2$ under a $N_2$ blanket is treated with carbonyldiimidazole (0.58 g, 3.55 mmole). The mixture is stirred at room temperature for 2 days to yield the imidazole intermediate. The reaction intermediate is not isolated but is treated with 3-methylpiperidine (1.46 g, 14.75 mmole). The reaction is continued with stirring at room temperature under nitrogen for 1 day. The solution is concentrated under reduced pressure to leave an oily residue. The residue is taken up in fresh $CH_2Cl_2$ and washed with 4×50 ml of water. The organic layer is concentrated under reduced pressure to leave an oily residue (1.81 g). The residue is chromatographed on a silica gel packed column with 5% MeOH/95% $CH_2Cl_2$ containing 0.7% $NH_4OH$ to yield the free base. The free base is dissolved in absolute alcohol and is then treated with saturated ethanolic/HCl with stirring. The alcoholic solution is concentrated under reduced pressure to an analytically pure (3β,5β,14β,17β)- 14-Amino-3-[[(3-methyl-1-piperidinyl)carbonyl]oxy] androstane-17-carboxylic Acid, Methyl Ester Hydrochloride Final Product.

EXAMPLE 25

(3β,5β,14β,17β)-14-Amino-3-[[[4-(2-hydroxyethyl)- 1-piperidinyl]carbonyl]oxylandrostane-17- carboxylic Acid, Methyl Ester Hydrochloride A stirred solution of (3β,5β,14β,17β)-14-Amino-3-hydroxy-androstane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with 1,1'-carbonyldiimidazole (0.87 g, 5.37 mmole). The mixture is stirred at room temperature overnight and then treated with 2-hydroxyethylpiperidine (2.86 g, 22.13 mmole). After stirring at room temperature under nitrogen for 2 days, the reaction solution is concentrated under reduced pressure to leave an oily residue. The residue is taken up in fresh $CH_2Cl_2$ and washed with 4×30 ml of water. The organic layer is concentrated under reduced pressure to leave a white solid residue (2.09 g). The residue is chromatographed on silica gel with 5% MeOH/95% $CH_2Cl_2$ containing 1% $NH_4OH$ to yield 1.55 g of free base. The free base in absolute alcohol is treated with saturated ethanolic/ HCl with stirring. The alcoholic solution is concentrated under reduced pressure to leave an oily residue. The oily residue is flushed with 3×50 ml of $CH_2Cl_2$ to yield the analytically pure (3β,5β,14β,17β)-14-Amino-3-[[[4-(2-hydroxyethyl) -1-piperidinyl]carbonyl]oxy]androstane-17-carboxylic Acid, Methyl Ester Hydrochloride Final Product.

EXAMPLE 26

(3β(S),5β,14β,17β)-14-Amino-3-[[[I- (hydroxymethyl)ethyl]amino]carbonyl]oxo] androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under $N_2$ is treated with 1,1'-carbonyldiimidazole (0.87 g, 5.37 mmole). The mixture is stirred at room temperature overnight to yield the imidazole intermediate. The intermediate is not isolated but is treated directly with L-2-amino-1-propanol (1.66 g, 22.13 mmole). After stirring at room temperature for three days, the reaction solution is concentrated under reduced pressure to leave an oily residue. The reaction residue is taken up in fresh $CH_2Cl_2$ and washed with 4×75 ml of water. The organic layer is concentrated under reduced pressure to leave an oily residue. The reaction residue is chromatographed on silica gel with 5% MeOH/95% $CH_2Cl_2$ containing 1% $NH_4OH$ to yield 1.55 g of free base. The free base in absolute alcohol is treated with saturated ethanolic/HCl with stirring. The alcoholic solution is concentrated under reduced pressure to leave an oily residue. The oily residue is flushed with 3×50 ml of $CH_2Cl_2$ to yield analytically pure (3β(S),5β,14β,17β)-14-Amino-3-[[[1-(hydroxymethyl)ethyl]amino]carbonyl]oxo]androstane-17-carboxylic Acid, Methyl Ester Hydrochloride Final Product.

EXAMPLE 27

(3β,5β,14β,17β)-14-Amino-3-[[[2,3-dihydroxypropyl)amino]carbonyl]oxy]androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with carbonyldiimidazole (0.87 g, 5.37 mmole). The mixture is stirred at room temperature overnight to yield the imidazole intermediate. The intermediate is not isolated but is treated directly with 2,3-dihydroxy-1-propylamine (2.02 g, 22.13 mmole). The reaction mixture is then treated with DMF to insure a solution. After stirring at room temperature under nitrogen for 5 days, the reaction solution is concentrated under reduced pressure to leave an oily residue. The residue is taken up in fresh $CH_2Cl_2$ and washed with 4×75 ml of water. The organic layer is concentrated under reduced pressure to leave an oily solid residue (1.28 g). The residue is chromatographed on a silica gel packed column with 7% MeOH/93% $CH_2Cl_2$ containing 1% $NH_4OH$ to yield the free base. The free base in absolute alcohol is treated with saturated ethanolic/HCl with stirring. The alcoholic solution is concentrated under reduced pressure to leave an oily residue. The oily residue is flushed with 3×50 ml of $CH_2Cl_2$ to yield analytically pure (3β,5β,14β,17β)-14-Amino-3-[[[2,3-dihydroxypropyl)amino]carbonyl]oxy]androstane-17-carboxylic Acid, Methyl Ester Hydrochloride Final Product.

EXAMPLE 28

(3β,5β,14β,17β)-14-Amino-3-[[[(2-hydroxypropyl)amino]carbonyl]oxy]androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with carbonyldiimidazole (0.87 g, 5.37 mmole). The mixture is stirred at room temperature for 2 days to yield the imidazole intermediate. The intermediate is not isolated but is treated directly with DL-1-amino-2-propanol (1.66 9, 22.13 mmole).

After stirring at room temperature under nitrogen for 2 days, the reaction solution is concentrated under reduced pressure to leave an oily residue. The residue is taken up in fresh $CH_2Cl_2$ and washed with 4×75 ml of water. The organic layer is concentrated under reduced pressure to leave an oily residue (1.40 g). The residue is chromatographed on a silica gel packed column with 5% MeOH/95% $CH_2Cl_2$ containing 0.7% $NH_4OH$ to yield the free base. The free base in absolute alcohol is treated with saturated ethanolic/HCl with stirring. The alcoholic solution is concentrated under reduced pressure to leave an oily residue. The oily residue is flushed with 3×50 ml of $CH_2Cl_2$ to yield analytically pure (3β,5β,14β,17β)-14-Amino-3-[[[(2-hydroxypropyl)amino]carbonyl]oxy]androstane-17-carboxylic Acid, Methyl Ester Hydrochloride Final Product.

EXAMPLE 29

(3β,5β,14β,17β)-14-Amino-3-[[(4-methyl-1-piperazinyl)carbonyl)oxy]androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with carbonyldiimidazole (0.87 g, 5.37 mmole). The mixture is stirred at room temperature 2 days to give the imidazole intermediate. The intermediate is not isolated but is treated directly with 4-methyl-1-piperazine (2.22 g, 22.13 mmole). After stirring at room temperature under nitrogen for 2 days. The reaction solution is concentrated under reduced pressure to leave an oily residue. The residue is taken up in fresh $CH_2Cl_2$ and washed with 4×30 ml of water. The organic layer is concentrated under reduced pressure to leave a white solid residue (1.82 g). The residue is chromatographed on a silica gel packed column with 3% MeOH/97% $CH_2Cl_2$ containing 0.07% $NH_4OH$ to yield the free base. The free base in absolute alcohol is treated with saturated ethanolic/HCl with stirring. The alcoholic solution is concentrated under reduced pressure to leave an oily residue. The oily residue is flushed with 3×50 ml of $CH_2Cl_2$ to yield analytically pure (3β,5β,14β,17β)-14-Amino-3-[[(4-methyl-1-piperazinyl)carbonyl]oxy]androstane-17-carboxylic Acid, Methyl Ester Hydrochloride Final Product.

EXAMPLE 30

(3β,5β,14β,17β)-14-Amino-3-[[[2-hydroxy-3-(1-piperidinyl)propyl]amino]carbonyl]oxy]androstane-17-carboxylic Acid, Methyl Ester Dihydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.48 g, 4.25 mmole) in 37.5 ml of $CH_2Cl_2$ under a $N_2$ blanket is treated with 1,1'-carbonyldiimidazole (0.83 g, 5.12 mmole). The mixture is stirred at room temperature overnight to yield the imidazole intermediate. The intermediate is not isolated but is treated directly with 1-aminomethyl-2-piperidinylethanol (3.36 g, 21.25 mmole). After stirring at room temperature under nitrogen for 2 days, the reaction solution is concentrated under reduced pressure to leave an oily residue. The residue is taken up in fresh $CH_2Cl_2$ and washed with 4×50 ml of water. The organic layer is concentrated under reduced pressure to leave an oily residue. The residue is chromatographed on silica gel with 5% MeOH/95% $CH_2Cl_2$ containing 0.7% $NH_4OH$ to yield the free base. The free base in absolute alcohol is treated with saturated ethanolic/HCl with stirring. The alcoholic solution is concentrated under reduced pressure to leave a semi-solid residue. The residue is flushed with 3×70 ml of $CH_2Cl_2$ to yield analytically pure (3β,5β,14β,17β)-14-Amino-3-[[[2-hydroxy-3-(1-piperidinyl)propyl]amino]carbonyl]oxy]androstane-17-carboxylic Acid, Methyl Ester Dihydrochloride Final Product.

EXAMPLE 31

(3β,5β,14β,17β)-14-Amino-3-[[[[2-[(2-hydroxyethyl)amino]ethyl]amino]carbonyl]oxy]androstane-17-carboxylic Acid, Methyl Ester Dihydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with carbonyldiimidazole (0.87 g, 5.37 mmole). The mixture is stirred at room temperature for 2 days to yield the imidazole intermediate. The intermediate is not isolated but is treated directly with 2-(2-aminoethyl-amino)ethanol (2.30 g, 22.13 mmole). After stirring at room temperature under nitrogen for 2 days, the reaction solution is concentrated under reduced pressure to leave an oily residue. The reaction residue is taken up in fresh $CH_2Cl_2$ and washed with 4×75 ml of water. The organic layer is concentrated under reduced pressure to leave a white solid residue (1.08 g). The residue is dissolved in absolute alcohol followed by the addition of saturated ethanolic/HCl with stirring. The alcoholic mixture is filtered and the filtrate treated with Darco (Celite). The alcoholic solution is concentrated under reduced pressure to leave the crude product. The crude product is chromatographed on silica gel with 20% MeOH/80%, followed by 30% MeOH/70%CHCl$_3$ to yield pure (3β,5β,14β,17β)-14-Amino-3-[[[[2-[(2-hydroxyethyl)-amino]ethyl]amino]carbonyl]oxy]androstane-17-carboxylic Acid, Methyl Ester Dihydrochloride Final Product.

EXAMPLE 32

(3β,5β,14β,17β)-14-Amino-3-[[[[1-(hydroxymethyl)butyl]amino]carbonyl]oxy]androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.31 g, 3.75 mmole) in 31.8 ml of $CH_2Cl_2$ under a $N_2$ blanket is treated with carbonyldiimidazole (0.74 g, 4.56 mmole). The mixture is stirred at room temperature for 2 days to yield the imidazole intermediate. The intermediate is not isolated but is treated directly with L-norvolinol (1.94 g, 18.83 mmole). After stirring at room temperature under nitrogen for 2 days, the reaction solution is concentrated under reduced pressure to leave an oily residue. The residue is taken up in fresh $CH_2Cl_2$ and washed with 4×50 ml of water. The organic layer is concentrated under reduced pressure to leave an oily residue (1.75 g). The residue is chromatographed on silica gel with 7% MeOH/93% $CH_2Cl_2$ containing 1% $NH_4OH$ to yield the free base. The free base in absolute alcohol is treated with saturated ethanolic/HCl with stirring. The alcoholic solution is concentrated under reduced pressure to leave an oily residue. The oily residue is flushed with 4×50 ml of $CH_2Cl_2$ to yield analytically pure (3β,5β,14β,17β)-14-Amino-3-[[[[-(hydroxymethyl)butyl]amino]carbonyl]oxy]androstane-17-carboxylic Acid, Methyl Ester Hydrochloride Final Product.

EXAMPLE 33

(3β,5β,14β,17β)-14-Amino-3-[[[(2-hydroxyethyl)methylamino]carbonyl]oxy]androstane-17-carboxylic Acid, Methyl Ester Hydrochloride A stirred solution of (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with carbonyldiimidazole (0.87 g, 5.37 mmole). The mixture is stirred at room temperature for 2 days to yield the imidazole intermediate. The intermediate is not isolated but is treated directly with 2-methylaminoethanol (1.66 g, 22.13 mmole). After stirring at room temperature under nitrogen for 2 days, the reaction solution is concentrated under reduced pressure to leave an oily residue. The residue is taken up in fresh $CH_2Cl_2$ and washed with 4×50 ml of water. The organic layer is concentrated under reduced pressure to leave a white solid residue (1.54 g). The residue is chromatographed on silica gel with 7% MeOH/93% $CH_2Cl_2$ containing 0.7% $NH_4OH$ to yield the free base. The free base in absolute alcohol is treated with saturated ethanolic/HCl with stirring. The alcoholic solution is concentrated under reduced pressure to leave an oily residue. The oily residue is flushed with 3×50 ml of $CH_2Cl_2$ to yield analytically pure (3β,5β,14β,17β)-14-Amino-3-[[[(2-hydroxyethyl)methylamino]carbonyl]oxy]androstane-17-carboxylic Acid, Methyl Ester Hydrochloride final product.

EXAMPLE 34

(3β,5β,14β,17β)-14-Amino-3-[[[(4-aminophenyl)amino]carbonyl]oxy]androstane-17-carboxylic Acid, Methyl Ester Dihydrochloride A. (3β,5β,14β,17β)-14-Amino-3-hydroxyandrostane-17-carboxylic Acid, Methyl Ester Hydrochloride (3β,5β,14β,17β)-14-Amino-3-hydroxyandrostane-17-carboxylic Acid, Methyl Ester, prepared according to the procedure described in U.S. Pat. No. 4,885,280, incorporated by reference herein, (0.90 g, 0.0026 mol) is dissolved in methanol (5 ml). Methanolic hydrochloric acid is added dropwise to acidify to a pH of 1 and the solution is stirred at ambient temperature for 10 min. The solution is concentrated under reduced pressure to an oil. Trituration of the oil with anhydrous ethyl ether forms a solid which is collected by filtration and air dried yielding 1.00 g (100%) of the hydrochloride salt. This compound is carried on to the next step.

B. (3β,5β,14β,17β)-14-Amino-3-[[[(4-nitrophenyl)amino]carbonyl]oxy]androstane-17-carboxylic Acid, Methyl Ester Hydrochloride To a suspension of 1 (1.0 g, 0.0026 mol) in anhydrous methylene chloride (250 ml) is added 4-nitrophenylisocyanate (1.2 g, 0.0073 mol, 2.8 eq). The mixture is heated to reflux for 20 hrs. Upon cooling to ambient temperature, the reaction mixture is concentrated under reduced pressure to a yellow solid. The solid is purified by chromatography on silica gel (230–400 mesh) eluting first with 100% methylene chloride to remove nonpolar impurities, then with 9:1 methylene chloride: methanol to elute the product. The fractions containing the product are combined and concentrated under reduced pressure to a solid which is dried in vacuo for 2 hrs yielding 0.72 g (51%) of the carbamate product. This compound is carried on to the next step.

C. (3β,5β,14β,17β)-14-Amino-3-[[[(4-aminophenyl)amino]carbonyl]oxy]androstane-17-carboxylic Acid, Methyl Ester Dihydrochloride Compound 2 (0.72 g, 0.0013 mol) is dissolved in methanol (100 ml). To the solution is added 10% palladium on activated carbon (0.1 g) and the mixture is hydrogenated on a Parr apparatus for 2 hrs. The reaction mixture is then filtered through celite and the filtrate is concentrated under reduced pressure to a solid. The solid is chromatographed on silica gel (230–400 mesh) using 9:1 methylene chloride: methanol as the eluent. Fractions containing the pure product are combined and concentrated under reduced pressure to a solid. The solid is dissolved in methanol (2 ml) and acidified with methanolic hydrochloric acid to a pH of 1. Addition of anhydrous ethyl ether causes a solid to precipitate. The solid is collected by filtration and dried in vacuo at 100° C. for 24 hrs to yield (3β,5β,14β,17β)-14-Amino-3-[[[(4-aminophenyl)amino]carbonyl]oxy]androstane-17-carboxylic Acid, Methyl Ester Dihydrochloride Final Product.

EXAMPLE 35

(3β,5β,14β,17β)-14-Amino-3-[[[3-(dibutylamino)-2-hydroxypropyl]carbonyl]oxy]androstane-17-carboxylic Acid, Methyl Ester Dihydrochloride A. 1-(Di-n-butylamino)-2,3-epoxypropane A stirred solution of epichlorohydrin (20.0 g, 0.22 mole) is treated dropwise with di-n-butylamine (29.73 g, 0.23 mole) over a 1 hour period followed by continued stirring at room temperature overnight. The reaction mixture is washed with 20% $K_2CO_3$ (50 ml). The organic layer is then stirred with 40% NaOH for 1 hour and then extracted with 3×100 ml portions of ether. The etheral extracts are pooled and washed with $H_2O$ (100 ml). The organic layer is dried over anhydrous $Na_2SO_4$ and filtered. The filtrate is concentrated under reduced pressure to leave the crude product (I) weighing 39.42 g. The crude product is distilled at 52°/0.15 mmHg to give 8.24 g (20.2%) pure product to be used as an intermediate in Part B.

B. 3-(Dibutylamino)-2-hydroxypropylamine

A solution of saturated methanolic amine containing I (4.07 g, 0.02 mole) is placed in pressure bomb. The bomb is heated at 100° for 2 days. The reaction solution is removed and concentrated under reduced pressure 90°/0.3 mmHg to give an oily residue. The residue is filtered and the filtrate II (4.27 g) used without further purification as an intermediate in Part C.

C. (3β,5β,14β,17β)-14-Amino-3-[[[3-(dibutylamino)-2-hydroxypropyl]carbonyl]oxy]androstane-17-carboxylic Acid, Methyl Ester Dihydrochloride A stirred solution of (3β,5β,14β,17β)-14-Amino-3-hydroxy-androstane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with carbonyldiimidazole (0.87 g, 5.37 mmole). The reaction is stirred at room temperature for 2 days to yield the imidazole intermediate. The intermediate is not isolated but treated directly with II (4.27 g, 21.12 mmole). The reaction is continued with stirring at room temperature under nitrogen for 2 days. The reaction solution is concentrated under reduced pressure to leave an oily residue. The reaction residue is taken up in fresh $CH_2Cl_2$ and washed with 3×75 ml of water. The organic layer is concentrated under reduced pressure to leave an oily residue (4.78 g). The reaction residue is chromatographed on silica gel with 5% MeOH/95% $CH_2Cl_2$ containing 0.7% $NH_4OH$ to yield free base. The free base in absolute alcohol is treated with saturated ethanolic/HCl with stirring. The alcoholic solution is concentrated under reduced pressure to leave an oily residue. The oily residue is flushed with 4×50 ml of $CH_2Cl_2$ to yield analytically pure (3β,5β,14β,17β)-14-Amino-3-[[[3-(dibutylamino)-2-hydroxypropyl]carbonyl]oxy]androstane-17-carboxylic Acid, Methyl Ester Dihydrochloride Final Product.

EXAMPLE 36

(3β,5β,14β,17β)-14-Amino-3-[[[3-[bis (2-methylpropyl)amino]-2-hydroxypropyl]amino]carbonyl]oxy]androstane-17-carboxylic Acid, Methyl Ester Dihydrochloride A. 1-(Diisobutylamino)-2,3-epoxypropane A stirred solution of epichlorohydrin (21.0 g, 0.23 mole) is treated dropwise with diisobutylamine (31.14 g, 0.24 mole) over a 1 hour period followed by continuous stirring at room temperature overnight. The reaction mixture is washed with 20% $K_2CO_3$ (50 ml). The organic layer is then stirred with 40% NaOH for 1 hour and then extracted with 3×100 ml portions of ether. The etheral extracts are pooled with the organic layer and washed with $H_2O$ (100 ml). The organic layer is dried over anhydrous $Na_2SO_4$ and filtered. The filtrate is concentrated under reduced pressure to leave the crude product. The crude product is distilled at 68°/0.1 mmHg to yield 15.83 g (37.14%) pure product to oe used as an intermediate in Part B.

B. 3-(Diisobutylamino)-2-hydroxypropylamine

A solution of saturated methanolic amine containing I (4.86 g, 0.02 mole) is placed in pressure bomb. The bomb is heated at 100° for 2 days. The reaction solution is removed and concentrated under reduced pressure to give an oily residue. The residue is triturated and filtered. The filtrate is concentrated under reduced pressure to leave an oil material (3.56 g, 80.1%), II, which is used without further purification as an intermediate in Part C.

C. (3β,5β,14β,17β)-14-Amino-3-[[[3-[bis(2-methylpropyl)amino]-2-hydroxypropyl]carbonyl]oxy]androstane-17-carboxylic Acid, Methyl Ester Dihydrochloride A stirred solution of (3β,5β,14β,17β)-14-Amino-3-hydroxy-androstane-17-carboxylic Acid, Methyl Ester, prepared according to the procedure described in U.S. Pat. No. 4,885,280, incorporated by reference herein, (1.55 g, 4.42 mmole) in 37.5 ml of $CH_2Cl_2$ under a $N_2$ blanket is treated with 1-1'-carbonyldiimidazole (0.87 g, 5.37 mmole). The mixture is stirred at room temperature for 2 days to give the imidazole intermediate. The reaction intermediate is not isolated but is treated with II (3.56 g, 17.62 mmole). After stirring at room temperature under nitrogen for 2 days, the reaction solution is concentrated under reduced pressure to leave an oily residue. The oily residue is taken up in fresh $CH_2Cl_2$ and washed with 10×100 ml of water. The organic layer is concentrated under reduced pressure to leave an oily residue (3.96 g). The oily residue is chromatographed on silica gel with 5% MeOH/95% $CH_2Cl_2$ containing 0.7% $NH_4OH$ to yield the free base. The free base in absolute alcohol is treated with saturated ethanolic/HCl with stirring. The alcoholic solution is concentrated under reduced pressure to leave an oily residue. The oily residue is flushed with 4×50 ml of $CH_2Cl_2$ to yield analytically pure (3β,5β,14β,17β)-14-Amino-3-[[[3-[bis(2-methylpropyl)amino]-2-hydroxypropyl]amino]carbonyl]oxy]androstane-17-carboxylic Acid, Methyl Ester Dihydrochloride Final Product.

EXAMPLE 37

(3β,5β,14β,17β)-14-Amino-3-[[[[1-(phenylmethyl)-4-piperidinyl amino]carbonyl]oxy]androstane-17-carboxylic Acid, Methyl Ester Dihydrochloride A stirred solution of (3β,5β,14β,17β)-14-Amino-3-hydroxy-androstane-17-carboxylic Acid, Methyl Ester, prepared according to the procedure described in U.S. Pat. No. 4,885,280, incorporated by reference herein, (4.0 g, 11.44 mmole) in 97.1 ml of $CH_2Cl_2$ under a $N_2$ blanket is treated with 1, 1'-carbonyldiimidazole (2.25 g, 13.88 mmole). The reaction is stirred at room temperature overnight to yield the imidazole intermediate. The intermediate is not isolated but is treated directly with 4-amino-1-benzylpiperidine (10.90 g, 57.28 mmole). After stirring at room temperature under nitrogen for 2 days, the reaction solution is concentrated under reduced pressure to leave an oily residue. The residue is taken up in fresh $CH_2Cl_2$ (300 ml) and washed with 6×300 ml of water to a neutral pH. The organic layer is concentrated under reduced pressure to leave a white solid residue (2.06 g). The residue is chromatographed on silica gel with 10% MeOH/90% CH$_2$Cl$_2$ containing 0.7% NH$_4$OH to yield the free base. The free base in absolute alcohol is treated with saturated ethanolic/HCl with stirring. The alcoholic solution is concentrated under reduced pressure to yield an oily residue. The oily residue is flushed with 3×50 ml of CH$_2$Cl$_2$ to yield analytically pure (3β,5β,14β,17β)-14-Amino-3-[[[[1-(phenylmethyl)-4-piperidinyl]amino]carbonyl]oxy]-androstane-17-carboxylic Acid, Methyl Ester Dihydrochloride Final Product.

EXAMPLE 38

(3β,5β,14β,17β)-14-Amino-3-[[[(2-hydroxy-1-methylpropyl)amino]carbonyl]oxy]androstane-17-carboxylic Acid, Methyl Ester Hydrochloride A. 2-Hydroxy-1-methylpropylamine trans-2,3-Epoxybutane (5.0 g, 0.008 mole) in saturated methanolic/amine (30 ml) is placed in a stainless steel digestion bomb. The bomb is heated at 100° for 3 days. The reaction solution removed and concentrated under reduced pressure to leave an oil residue (3.39 g). The oil residue is distilled (27° at 0.2 mmHg) to yield the intermediate amine I to be used in Part B (1.4 g, 21%).

B. [3β,5β,14β,17β]-14-Amino-3-[[[(2-hydroxy-1-methylpropyl)amino]carbonyl]oxy]androstane-17-carboxylic Acid, Methyl Ester Hydrochloride A stirred solution of (3β,5β,14β,17β)-14-Amino-3-hydroxy-androstane-17-carboxylic Acid, Methyl Ester, prepared according to the procedure described in U.S. Pat. No. 4,885,280, incorporated by reference herein, (1.55 g, 4.42 mmole) in 37.5 ml of CH$_2$Cl$_2$ under a N$_2$ blanket is treated with carbonyldiimidazole (0.87 g, 5.37 mmole). The mixture is stirred at room temperature for 2 days to yield the imidazole intermediate. The reaction intermediate is not isolated but is treated directly with I (1.40 g, 15.70 mmole). After stirring at room temperature under nitrogen for 2 days, the reaction mixture is filtered and the filtrate is concentrated under reduced pressure to leave an oily residue. The residue is taken up in fresh CH$_2$Cl$_2$ and washed with 6×120 ml of water. The organic layer is concentrated under reduced pressure to leave a white solid residue (2.09 g). The residue is chromatographed on silica gel with 10% MeOH/90% CH$_2$Cl$_2$ containing 0.7% NH$_4$OH to yield the free base. The free base in absolute alcohol is treated with saturated ethanolic/HCl with stirring. The alcoholic solution is concentrated under reduced pressure to leave an oily residue. The oily residue is flushed with 4×50 ml of CH$_2$Cl$_2$ to yield analytically pure (3β,5β,14β,17β)-14-Amino-3-[[[(2-hydroxy-1-methylpropyl)amino]carbonyl]oxy]androstane-17-carboxylic Acid, Final Product.

EXAMPLE 39

(3β,5β,14β,17β)-14-Amino-3-[[[3-(dipropylamino)-2-hydroxypropyl]carbonyl]oxy]androstane-17-carboxylic Acid, Methyl Ester Dihydrochloride A. 1-(Dipropylamino)-2,3-epoxypropane A stirred solution of epichlorohydrin (20.0 g, 0.22 mole) is treated dropwise with dipropylamine (23.14 g, 0.23 mole) over a 1 hour period followed by continuous stirring at room temperature overnight. The reaction mixture is washed with 20% K$_2$CO$_3$ (50 ml). The organic layer is then stirred with 40% NaOH for 1 hour. The organic layer is separated and the aqueous layer is extracted with 3×100 ml portions of ether. The etheral extracts are pooled with the organic layer and washed with H$_2$O (100 ml). The organic layer is dried over anhydrous Na$_2$SO$_4$ and filtered. The filtrate is concentrated under reduced pressure to yield the crude product (I) weighing 35.3 g. The crude product is distilled at 34°/0.1 mmHg to yield 7.23 g (21.0%) pure product to be used as an intermediate in Part B.

B. 3-Dipropylamino)-2-hydroxypropylamine

A solution of saturated methanolic amine containing I (3.46 g, 0.02 mole) is placed in a pressure bomb. The bomb is heated at 100° for 2 days. The reaction solution is removed and concentrated under reduced pressure to yield an oily residue. The residue is filtered and the filtrate concentrated under reduced pressure to yield the product II. Pure product is obtained by distillation at 63–68° at 0.2 mmHg (2.33 g, 22%). The product is used as an intermediate in Part C.

C. (3β,5β,14β,17β)-14-Amino-3-[[[3-(dipropylamino)-2-hydroxypropyl)carbonyl]oxy]androstane-17-carboxylic Acid, Methyl Ester Dihydrochloride A stirred solution of (3β,5β,14β,17β)-14-Amino-3-hydroxy-androstane-17-carboxylic Acid, Methyl Ester, prepared according to the procedure described in U.S. Pat. No. 4,885,280, incorporated by reference herein, (1.55 g, 4.42 mmole) in 37.5 ml of CH$_2$Cl$_2$ under a N$_2$ blanket is treated with 1,1'-carbonyidiimidazole (0.87 g, 5.37 mmole). The reaction is stirred at room temperature for 2 days to yield the imidazole intermediate. The reaction intermediate is not isolated but is treated directly with II (2.33 g, 15.4 mmole). The reaction is continued with stirring at room temperature under nitrogen for 2 days then heated at reflux for 8 hours. The reaction solution is concentrated under reduced pressure to leave an oil residue. The residue is taken up in fresh CH$_2$Cl$_2$ and washed with 16×110 ml of water. The organic layer is concentrated under reduced pressure to leave an oily residue (2.58 g). The oily residue in absolute alcohol is treated with saturated ethanolic/HCl with stirring. The alcoholic solution is concentrated under reduced pressure to leave an oily residue. The oily residue is flushed with 4×25 ml of CH$_2$Cl$_2$ to yield analytically pure (3β,5β,14β,17β)-14-Amino-3-[[[3-(dipropylamino)-2-hydroxypropyl]carbonyl]oxyaandrostane-17-carboxylic Acid, Methyl Ester Dihydrochloride Final Product.

EXAMPLE 40

(3β,5β,14β,17β)-14-Amino-3-[[(4-amino-1-piperidinyl]carbonyl]oxy]androstane-17-carboxylic Acid, Methyl Ester Dihydrochloride A. 4-Aminopiperidine A stirred solution of ethyl 4-amino-1-piperidine carboxylate (5.0 g, 0.003 mole) in 100 ml of 20% NaOH is heated at reflux for 8 hours. The reaction solution is extracted with 3×150 ml portions of CH$_2$Cl$_2$ followed by pooling of the extracts. The extracts are dried over anhydrous Na$_2$SO$_4$ and are then filtered. The filtrate is concentrated under reduced pressure to leave 4-aminopiperidine I (3.06 g). I is used without further purification as an intermediate in Part B.

B. (3β,5β,14β,17β)-14-Amino-3-[[(4-amino-1-piperidinyl]-carbonyl]oxy]androstane-17-carboxylic Acid, Methyl Ester Dihydrochloride A stirred solution of (3β,5β,14β,17β,)-14Amino-3-hydroxy-androstane-17-carboxylic Acid, Methyl Ester, prepared according to the procedure described in U.S. Pat. No. 4,885,280, incorporated by reference herein, (1.55 g, 4.42 mmole) in 37.5 ml of CH$_2$Cl$_2$ under a N$_2$ blanket is treated with 1,1'-carbonyldiimidazole (0.87 g, 5.37 mmole). The reaction is stirred at room temperature for 2 days to yield the imidazole intermediate. The reaction intermediate is not isolated but is treated directly with I (3.06 g, 30.6 mmole). The reaction is continued with stirring at room temperature under nitrogen for 2 days; the reaction mixture is then filtered and the filtrate is concentrated under reduced pressure to yield an oily residue. The residue is taken up in fresh CH₂Cl₂ and washed with 4×50 ml of water. The organic layer is concentrated under reduced pressure to leave a white solid residue (2.03 g). This residue, in absolute alcohol, is treated with saturated ethanolic/HCl with stirring. The alcoholic solution is concentrated under reduced pressure to leave an oily residue. The residue is flushed with 2×75 ml portions of CH₂Cl₂ to yield the crude product as a white solid 2.14 g. This solid is chromatographed on silica gel with 20% MeOH/80% CHCl₃ to yield pure (3β,5β,14β,17β)-14-Amino-3-[[(4-amino-1-piperidinyl]carbonyl]oxy]androstane-17-carboxylic Acid, Methyl Ester Dihydrochloride Final Product.

EXAMPLE 41

(3β,5β,14β,17β)-14-Amino-3-[[[(4-piperidinyl]amino]carbonyl]oxy]androstane-17-carboxylic Acid, Methyl Ester Dihydrochloride A stirred mixture of dried Pearlman's catalyst (2.27 g) in 54 ml of dry methanol under a N₂ blanket is treated with ammonium formate (1.71 g, 0.03 mole) at such a rate to maintain 40° reaction temperature. The reaction is further heated at 40° for 20 minutes followed by the addition of (3β,5β,14β,17β)-14-Amino-3-[[[1-phenylmethyl)-4-piperidinyl]amino]carbonyl]oxy]androstane-17-carboxylic Acid, Methyl Ester Dihydrochloride, (0.83g,1.30 mmole) in 50 ml of dry methanol. Carbon dioxide evolution is observed during the addition. The reaction mixture is stirred at 40° for 1.5 hours and then filtered and the solid washed with methanol. The filtrate and methanol washed were combined and concentrated under reduced pressure to leave an oil residue. The residue is treated with 2% NaOH and extracted with 4×100 ml of portions of CH₂Cl₂. The CH₂Cl₂ extracts are pooled and are washed with brine and dried over anhydrous Na₂SO₄. The desiccant is removed and the filtrate concentrated under reduced pressure to leave a white solid product as the free base (0.37 g). The free base in absolute alcohol is treated with saturated ethanolic/HCl with stirring. The alcoholic solution is concentrated under reduced pressure to leave an oily residue. The oily residue is flushed with 4×50 ml of CH₂Cl₂ to yield analytically pure (3β,5β,14β,17β)-14-Amino-3-[[[(4-piperidinyl]amino]carbonyl]oxy]androstane-17-carboxylic Acid, Methyl Ester Dihydrochloride Final Product.

EXAMPLE 42

(3β,5β,14β,17β)-14-Amino-3-[[[(3-hydroxy-1-methylpropyl)amino]carbonyl]oxy]androstane-17-carboxylic Acid, Methyl Ester Hydrochloride A. 3-Aminobutanol A stirred solution of lithium borohydride (4.10 g, 0.19 mole) in dry THF (100 ml) under a nitrogen blanket is treated dropwise with trimethylsilyl chloride (40.56 g, 0.37 mole). The reaction mixture is maintained at 25–30° with an ice bath. The reaction is treated portionwise with DL-3-aminobutyric acid (9.69 g, 0.09 mole). Caution-reaction exothermic with foaming. After stirring at room temperature overnight, the reaction is treated cautiously with dry MeOH (140 ml). The reaction solution is concentrated under reduced pressure to leave a thick oil residue. The residue is treated cautiously with 20% NaOH (250 ml) followed by extraction with 3×250 ml portions of CH₂Cl₂. The extracts were pooled and dried over anhydrous Na₂SO₄. The desiccant is removed and the filtrate concentrated under reduced pressure to yield the crude product I. The product is distilled at 50° 0.5 mmHg to yield 2.3 g (28.7%) of material to be used as an intermediate in Part B.

(3β,5β,14β,17β)-14-Amino-3-[[[(3-hydroxy-1-methylpropyl)amino]carbonyl]oxy]androstane-17-carboxylic Acid, Methyl Ester Hydrochloride A stirred solution of (3β,5β,14β,17β)-14-Amino-3-hydroxy-androstane-17-carboxylic Acid, Methyl Ester, prepared according to the procedure described in U.S. Pat. No. 4,885,280, incorporated by reference herein, (1 g, 2.86 mmole) in 24.35 ml of CH₂Cl₂ under a N₂ blanket is treated with carbonyldiimidazole (0.52 g, 3.48 mmole). The reaction is stirred at room temperature for 2 days to yield the imidazole intermediate. The reaction intermediate is not isolated but is treated with I (1.53 g, 17.23 mmole). The reaction mixture is heated at reflux under nitrogen for 6 days. The reaction solution is concentrated under reduced pressure to leave an oily residue. The reaction residue is taken up in fresh CH₂Cl₂ and washed with 6×100 ml of water. The organic layer is concentrated under reduced pressure to leave a white solid residue (1.2 g). The reaction residue is chromatographed on silica gel with 10% MeOH/90% CH₂Cl₂ containing 0.7% NH₄OH to yield the free base. The free base in absolute alcohol is treated with saturated ethanolic/HCl with stirring. The alcoholic solution is concentrated under reduced pressure to leave an oily residue. The oily residue is flushed with 4×50 ml of CH₂Cl₂ to yield analytically pure (3β,5β,14β,17β)-14-Amino-3-[[[(3-hydroxy-1-methylpropyl)amino]carbonyl]oxy]androstane-17-carboxylic Acid, Methyl Ester Hydrochloride Final Product.

EXAMPLE 43

(3β,5β,14β,17β)-3-[[[2-Acetyloxy-3-(1-piperidinyl)propyl]amino]carbonyl]oxy]-14-aminoandrostane-17-carboxylic Acid, Methyl Ester Dihydrochloride (3β,5β,14β,17β)-14-Amino-3-[[[2-hydroxy-3-(1-piperidinyl)propyl]amino]carbonyl]oxy]androstane-17-carboxylic Acid, Methyl Ester Dihydrochloride, (0.12 g, 0.2 mmol) is dissolved in anhydrous acetic anhydride (5 ml). Anhydrous pyridine (47 ml) is added and the reaction is allowed to stir at ambient temperature for 20 hrs. The reaction mixture is concentrated under reduced pressure to an oil which is chromatographed on silica gel (230–400 mesh) using 9:1 methylene chloride : methanol as the eluent. Fractions containing the pure product are combined and concentrated under reduced pressure to a solid. The solid is dissolved in methanol (1 ml) and ethanolic hydrochloric acid is added dropwise to acidify to a pH of 1. The solution is concentrated under reduced pressure to an oil. Trituration of the oil with anhydrous ethyl ether formed the hydrochloride salt as a solid which is collected by filtration and drying in vacuo at 77° C., yielding (3β,5β,14β,17β)-3-[[[2-Acetyloxy-3-(1-piperidinyl)propyl]amino]carbonyl]oxy]-14-aminoandrostane-17-carboxylic Acid, Methyl Ester Dihydrochloride Final Product.

EXAMPLE 44

(3β,5β,14β,17β)-14-Amino-3-[[[4-(phenylmethyl)-1-piperazinyl]carbonyl]oxy]androstane-17-carboxylic Acid, Methyl Ester Dihydrochloride A stirred solution of (3β,5β,14β,17β)-14-Amino-3-hydroxy-androstane-17-carboxylic Acid, Methyl Ester, prepared according to the procedure described in U.S. Pat. No.

4,885,280, incorporated by reference herein, (1.55 g, 4.42 mmole) in 37.5 ml of $CH_2Cl_2$ under a $N_2$ blanket is treated with 1,1'-carbonyldiimidazole (0.87 g, 5.37 mmole). The reaction is stirred at room temperature for 2 days to yield the imidazole intermediate. The reaction intermediate is not isolated but is treated with 1-benzylpiperazine (3.90 g, 22.1 mmole). After stirring at room temperature under nitrogen for 2 days, the reaction solution is concentrated under reduced pressure to leave an oily residue. The reaction residue is taken up in fresh $CH_2Cl_2$ and washed with 12×100 ml of water. The organic layer is concentrated under reduced pressure to leave a clear oil residue (3.91 g). The reaction residue is chromatographed on silica gel with 5% MeOH/ 95% $CH_2Cl_2$ containing 2% $NH_4OH$ to yield the free base. The free base in absolute alcohol is treated with saturated ethanolic/HCl with stirring. The alcoholic solution is concentrated under reduced pressure to leave a solid residue. The residue is flushed with 4×100 ml of $CH_2Cl_2$ to yield analytically pure (3β,5β,14β,17β)-14-Amino-3-[[[4-(phenyl-methyl)-1-piperazinyl]carbonyl]oxy]androstane-17-carboxylic Acid, Methyl Ester Dihydrochloride Final Product.

EXAMPLE 45

(3β(S),5β,14β,17β)-3-[[[[2-(Acetyloxy)-1-phenylethyl]amino]carbonyl]oxy]-14-amino-N-methylandrostane-17-carboxamide Hydrochloride (3β(R),5β,14β,17β)-14-Amino-3-[[[(2-hydroxy-1-phenylethyl)-amino]carbonyl]oxy]-N-methylandrostane-17-carboxamide Hydrochloride, (0.45 g, 0.82 mmol) is suspended in anhydrous acetic anhydride (25 ml). Anhydrous pyridine (66 ul) is added and the reaction is allowed to stir at ambient temperature for 20 hrs. The reaction is diluted with anhydrous ethyl ether (200 ml) which precipitates a white solid. The solid is collected by filtration and dried at 77° C. for 24 hrs yielding (3β(S),5β,14β,17β)-3-[[[[2-(Acetyloxy)-1-phenylethyl]amino]carbonyl]oxy]-14-amino-N-methylandrostane-17-carboxamide Hydrochloride Final Product.

EXAMPLE 46

(3β(E),5β,14β,17β)-14-Amino-3-[[(3-hydroxy-1-piperidinyl)carbonyl]oxy]androstane-17-carboxylic Acid, Methyl Ester Hydrochloride A) 3-Hydroxy-1-Piperidinecarboxylic Acid, Phenylmethyl Ester To a 1-liter 3-necked round bottom flask, equipped with mechanical stirrer and two addition funnels, is added 30 g (0.2966 mole) of 3-hydroxypiperidine and 300 ml of water. The resulting solution is stirred and is cooled to ~0° C. with ice-salt bath. At this point the benzyl chloroformate (51 ml, 0.356 mole) is added dropwise from one funnel and the 2N NaOH (178 ml) from the other funnel (at a slightly faster rate) during which time the temp. is maintained at ~0° C. After addition is complete, the mixture is stirred in the cold for 2 hr, then overnight at ambient temp. After this time an oily residue separates from the reaction solution. Ethyl acetate is added (250 ml) to the reaction and is stirred for ½ hr. The phases are separated and the aqueous phase is extracted once more with EtOAc (250 ml). All organic phases are combined, washed with 1×150 ml saturated $NaHCO_3$, 1×150 ml $H_2O$, 1×150 ml 10% HCl, 1×150 ml $H_2O$ and dried over$MgSO_4$. The mixture is filtered and concentrated on a roto-evap under reduced pressure, to yield a viscous oil, which is stored under vacuum to remove any residual solvents as, 3-Hydroxy-1-piperidinecarboxylic Acid, Phenylmethyl Ester, a clear oil.

B) 3-[[(1-Phenylethyl)amino]carbonyloxy]piperidine-1-carboxylic Acid, PhenylMethyl Ester The S(-)-1-phenylethyl isocyanate (14.33 ml, 0.1 mole) is added to a green heterogenous mixture of the alcohol 3-Hydroxy-1-piperidinecarboxylic Acid, Phenylmethyl Ester(23.53 g, 0.1 mole), reagent grade CuCl (9.9 g, 0.1 mole) and dry DMF (500 ml), in a 1 liter single neck round bottom flask with magnetic stir bar and drying tube. The mixture is stirred at room temperature, until the reaction is complete by TLC (4–6 hr); and the reaction mixture is diluted with $Et_2O$ (250 ml) and $H_2O$ (250 ml); then the mixture is stirred for ½ hr. The phases are separated. To the aqueous/DMF phase is added another 250 ml $Et_2O$ and 250 ml $H_2O$ with stirring for ½hr. The $Et_2O$ phase is saved. Both $Et_2O$ phases are combined, washed with 1×230 ml brine, dried over $MgSO_4$ and filtered. The filtrate is concentrated on roto-evap, under reduced pressure, to a semi-solid residue, 3-[[(1-Phenylethyl)amino]carbonyloxy]piperidine-1-carboxylic Acid, PhenylMethyl Ester, as a mixture of the desired diastereoisomers. Trituration of 3-[[(1-Phenylethyl)amino]carbonyloxy]piperidine-1-carboxylic Acid, Phenyl-Methyl Ester with EtOAc induces crystallization of the 3S isomer which after one recrystallization from EtOAc yields analytically pure 3S isomer of 3-[[(1-Phenylethyl)amino]carbonyloxy]piperidine-1-carboxylic Acid, PhenylMethyl Ester, suitable for x-ray diffraction; 7.64 g [59%].

Purification of the mother liquor (from trituration) by preparative HPLC using the mobile phase of 35% EtOAc/ hexanes yields analytically pure 3R isomer of 3-[[(1-Phenylethyl)-amino]carbonyloxy]piperidine-1-carboxylic Acid, PhenylMethyl Ester, 9.9 g (43%).

C) R-(-)-3-Hydroxy-1-piperidinecarboxylic Acid, Phenylmethyl Ester

To a solution of carbamate (9.94 g, 0.026 mole) and triethylamine (7.25 ml, 0.052 mole) in 150 ml of dry toluene under $N_2$ is added dropwise (10 min) a solution of trichlorosilane (5.25 ml, 0.052 mole) in 50 ml of dry toluene. After silane addition, the stirred solution is heated to reflux for 16 hr. Alternatively, the reaction may be conducted at room temperature for longer periods (24–48 hr). Reactions are worked up by removing all salts by filtration, concentration on roto-evap to remove all solvents and redissolving the residue in ethyl acetate. The organic layer is washed with two 50-ml portions of saturated aqueous $NH_4Cl$ and is dried over anhydrous $MgSO_4$. Carbinols are isolated by liquid chromatography, using the mobile phase of 15% EtOAc/ $CH_2Cl_2$ at 100 ml/min.

Those fractions showing one spot ($R_f$=0.72) (10% MeOH/ CH2Cl2) are combined and concentrated on roto-evap, under reduced pressure, to yield 3.9 g of an amber oil R-(-)-3-Hydroxy-1-piperidinecarboxylic Acid, Phenylmethyl Ester.

D) (R)-(+)-3-Hydroxypiperidine

The protected amine R-(-)-3-Hydroxy-1-piperidinecarboxylic Acid, Phenylmethyl Ester (3.5 g, 0.0149 mole), MeOH (dry-50 ml) and 350 mg of 5% Pd/C (wet) in a 500 ml glass hydrogenation bottle is subjected to hydrogenation on Parr shaker for 24 hr.

The reaction mixture is filtered through a Celite pad to remove spent catalyst. The filtrate is checked for completion by TLC, then concentrated on a roto-evap, under reduced pressure, to a tan oily residue-1.6 g. Purification by flash chromatography using the mobile phase 35% MeOH/ $CH_2Cl_2$+10 ml $NH_4OH$/liter gave a tan solid, which sublimed (0.1 mmHg at 55° C.) to a white solid (R)-(+)-3-Hydroxypiperidine; 1.1 g [73%].

E) (3β(R),5β,14β,17β)-14-Amino-3-[[(3-hydroxy-1-piperidinyl)carbonyl)oxy ]-androstane-17-carboxylic Acid, Methyl Ester Hydrochloride To a solution of 1.04 g (0.003 m) of (3β,5β,14β,17β)-14-Amino-3-hydroxyandrostane-17-carboxylic Acid, Methyl Ester in 40 ml of CH2Cl2 under $N_2$ and stirring for ½ hr, is added 0.54 g (0.0033 m) of 1,1'-carbonyldiimidazole. After 48 hr of stirring at room temperature, 0.9 g (0.009 m) of R-(+)-3-hydroxy-piperidine is added. After 48 hr (NOTE 1) the slightly cloudy solution is filtered and the filtrate is washed with distilled water until the washing is neutral (5×30 ml). After drying over $MgSO_4$, $CH_2Cl_2$ is evaporated under reduced pressure to yield 1.47 g of a white solid, TLC ($CHCl_3$:MeOH=9/1 or 8/2) shows essentially 2 spots. The solid is purified by flash chromatography (5% MeOH/ $CH_2C_{12}$, $NH_4OH$) and is then dissolved in 40 ml EtOH, added 4 ml EtOH/HCl and stirred for 4 hr. The solid is concentrated on a roto-evap to a semi-solid which is azeotroped with 50 ml $CH_2Cl_2$ and recrystallized from acetonitrite to the analytically pure (3β(R),5β,14β,17β)-14-Amino-3-[[(3-hydroxy-1-piperidinyl)carbonyl]oxy] androstane-17-carboxylic Acid, Methyl Ester Hydrochloride Final Product.

NOTE 1: The length of the reaction time varies from 2 to 7 days and should be monitored by TLC.

EXAMPLE 47

(3β(R),5β,14β,17β)-14-Amino-3-[[(3-hydroxy-1-piperidinyl)carbonyl]oxy]androstane-17-carboxylic Acid, Methyl Ester Hydrochloride A) 3-Hydroxy-1-piperidinecarboxylic Acid, Phenylmethyl Ester To a 1-liter 3-necked round bottom flask, equipped with mechanical stirrer and two addition funnels, is added 30 g (0.2966 mole) of 3-hydroxypiperidine and 300 ml of water. The resulting solution is stirred and is cooled to ~0° C. with ice-salt bath. At this point benzyl chloroformate (51 ml, 0.356 mole) is added dropwise from one funnel and the 2N NaOH (178 ml) from the other funnel (at a slightly faster rate) during which time the temp. is maintained at ~0° C. After addition is complete, stir cold for 2 hr, then overnight at ambient temp. After this time an oily residue separates from the reaction solution, ethyl acetate is added (250 ml) to the reaction and is stirred for ½ hr. The phases are separated and the aqueous phase is extracted once more with EtOAc (250 ml). All organic phases are combined, washed with 1×150 ml saturated $NaHCO_3$, 1×150 ml H20, 1×150 ml 10% HCl, 1×150 ml H20 and dried over $MgSO_4$. The mixture is filtered and concentrated on roto-evap under reduced pressure to yield a viscous oil which is stored under vacuum to remove any residual solvents as 3-Hydroxy-1-piperidinecarboxylic Acid, Phenylmethyl Ester, a clear oil.

B) 3-[[(1-Phenylethyl)amino]carbonyloxy]piperidine-1-carboxylic Acid, Phenyl Methyl Ester The S(–)-1-phenylethyl isocyanate (14.33 ml, 0.1 mole) is added to a green heterogenous mixture of the alcohol 3-Hydroxy-1-piperidinecarboxylic Acid, Phenylmethyl Ester, a clear oil (23.53 g, 0.1 mole), reagent grade CuCl (9.9 g, 0.1 mole) and dry DMF (500 ml), in a 1 liter single neck round bottom flask with magnetic stir bar and drying tube. The mixture is stirred at room temperature until the reaction is complete by TLC (4–6 hr). The reaction mixture is diluted with $Et_2O$ (250 ml) and $H_2O$ (250 ml), and then stirred for ½ hr. The phases are separated and the $Et_2O$ layer is saved. To the aqueous/DMF phase is added another 250 ml $Et_2O$ and 250 ml $H_2O$ with stirring for ½ hr. The $Et_2O$ phase is saved. Both $Et_2O$ phases are combined, washed with 1×230 ml brine, dried over $MgSO_4$ and filtered. The filtrate is concentrated on roto-evap, under reduced pressure, to a semi-solid residue of 3-[[(1-Phenylethyl)-amino]carbonyloxy]piperidine-1-carboxylic Acid, Phenyl Methyl Ester as a mixture of the desired diastereoisomers. Trituration of 3-[[(1-Phenylethyl)amino]carbonyloxy]-piperidine-1-carboxylic Acid, Phenyl Methyl Ester with EtOAc induces crystallization of the 3S isomer which after one recrystallization from EtOAc yields analytically pure 3S isomer of 3-[[(1-Phenylethyl)amino]carbonyloxy]piperidine-1-carboxylic Acid, Phenyl Methyl Ester, suitable for x-ray diffraction; 7.64 g [59%].

Purification of the mother liquor (from trituration) by preparative HPLC using the mobile phase of 35% EtOAc/ hexanes yields analytically pure 3R isomer of 3-[[(1-Phenylethyl)-amino]carbonyloxy]piperidine-1-carboxylic Acid, Phenyl Methyl Ester, 9.9 g (43%); TLC: Rf0.23 (35% EtOAc/hexanes).

C) S-(+)-3-Hydroxy-1-piperidinecarboxylic Acid, Phenylmethyl Ester

To a solution of carbamate (7.64 g, 0.02 mole) and triethylamine (5.58 ml, 0.04 mole) in 150 ml of dry toluene under $N_2$ is added dropwise (10 min) a solution of trichlorosilane (4.04 ml, 0.04 mole) in 50 ml of dry toluene. After silane addition, the stirred solution is heated to reflux for 16 hr. Alternatively, the reaction may be conducted at room temperature for longer periods (24–48 hr). Reactions are worked up by removing all salts by filtration, concentration on roto-evap to remove all solvents and redissolving in ethyl acetate. Wash the organic layer with two 50-ml portions of saturated aqueous $NH_4Cl$ and dry it over anhydrous $MgSO_4$. Carbinols are isolated by liquid chromatography, using the mobile phase of 20% EtOAc/$CH_2C_{12}$ at 100 ml/min.

These functions showing one spot ($R_f$=0.72) (10% MeOH/$CH_2C_{12}$) are combined and concentrated on roto-evap, under reduced pressure, to yield 3.0 g of a white solid for S-(+)-3-Hydroxy-1-piperidinecarboxylic Acid, Phenylmethyl Ester [64%].

D) (S)-(–)-3-Hydroxypiperidine

The protected amine S-(+)-3-Hydroxy-1-piperidinecarboxylic Acid, Phenylmethyl Ester (3.0 g, 0.0128 mole), MeOH (dry-50 ml) and 350 mg of 5% Pd/C (wet) in a 500 ml glass hydrogenation bottle is subjected to hydrogenation on a Parr shaker for 24 hr.

The reaction mixture is filtered through a Celite pad to remove spent catalyst. The filtrate is checked for completion by TLC, then concentrated on roto-evap under reduced pressure, to a tan oily residue-1.6 g. Purification by flash chromatography using the mobile phase 35% MeOH/ $CH_2Cl_2$+10 ml $NH_4OH$/liter gave a thick oil for S)-(–)-3-Hydroxypiperidine; 1.1 g [83%].

E) (3β(S),5β,14β,17β)-14-Amino-3-[[(3-hydroxy-1-piperidinyl) carbonyl)oxy]-androstane-17-carboxylic Acid, Methyl Ester Hydrochloride.

To a solution of 1.04 g (0.003 m) of (3β,5β,14β,17β)-14-Amino-3-hydroxyandrostane-17-carboxylic Acid, Methyl Ester, prepared according to the procedure described in U.S. Pat, No. 4,885,280, incorporated by reference herein, in 40 ml of $CH_2Cl_2$ under $N_2$ and stirring for ½ hr, is added 0.54 g (0.0033 m) of 1,1'-carbonyldiimidazole. After 48 hr of stirring at room temperature, 0.9 g (0.009 m) of S-(–)-3-hydroxy-piperidine is added. After 48 hr (NOTE 1) the slightly cloudy solution is filtered and the filtrate is washed with distilled water until the washing is neutral (5×30 ml). After drying over $MgSO_4$, $CH_2Cl_2$ is evaporated under reduced pressure to yield 1.27 g of a white solid, TLC ($CHCl_3$:MeOH=9/1 or 8/2) shows 2 spots. The solid is purified by flash chromatography (5% MeOH/CH$_2$Cl$_2$, NH$_4$OH); then it is dissolved in 40 ml EtOH and 4 ml EtOH/HCl are added and stirred for 4 hr. The solution is concentrated on a roto-evap to a semi-solid and is azeotroped with 50 ml CH$_2$Cl$_2$ and recrystalled from acetonitrite to yield analyticaly pure (3β(S),5β,14β,17β)-14-Amino-3-[[(3-hydroxy-1-piperidinyl)carbonyl]oxy]androstane-17-carboxylic Acid, Methyl Ester Hydrochloride Final Product.
NOTE 1: The length of the reaction time varies from 2 to 7 days and should be monitored by TLC.

EXAMPLE 48

(3β,5β,14β,17β)-3-(Acetyloxy)-1-piperidinyl] carbonyl]oxy]-14-amino-N-methylandrostane-17-carboxamide Hydrochloride A stirred mixture of (3β,5β,14β,17β)-14-Amino-3-[[(3-hydroxy-1-piperidinyl)carbonyl]oxy]-N-methylandrostane-17-carboxamide Hydrochloride, (0.59 g, 1.14 mmole) in 100 ml of acetic anhydride under N$_2$ is treated with pyridine (0.2 ml, 2.47 mmole). The reaction mixture is heated at 70° for 2 hours and then filtered. The filtrate is concentrated under reduced pressure to leave a white solid residue (0.50 g). The reaction residue is chromatographed on silica gel with 10% MeOH/90% CH$_2$Cl$_2$ containing 1% NH$_4$OH to give an oil residue as the free base. The free base in absolute alcohol is treated with saturated ethanolic/HCl with stirring. The alcoholic solution is concentrated under reduced pressure to leave an oily residue. The oily residue is flushed with 4×25 ml of CH$_2$Cl$_2$ to yield analytically pure (3β,5β,14β,17β)-3-(Acetyloxy)-1-piperidinyl]carbonyl]oxy]-14-amino-N-methylandrostane-17-carboxamide Hydrochloride Final Product.

EXAMPLE 49

(3β,5β,14β,17β)-14-Amino-3-[[[[2-(Acetyloxy)-1-methylpropyl]amino]carbonyl]oxy]-14-amino-androstane-17-carboxylic Acid, Methyl Ester Hydrochloride A stirred solution of (3β,5β,14β,17β)-14-Amino-3-[[[(2-hydroxy-1-methylpropyl)amino]carbonyl]oxy]androstane-17-carboxylic Acid, Methyl Ester Hydrochloride, (190 mg, 0.38 mmole) in 50 ml of acetic anhydride is treated with three drops of glacial acetic acid followed by heating at 50° for 4 hours. The reaction mixture is further heated at 70° for 11 hours. The reaction mixture is chilled and concentrated under reduced pressure to leave an oily residue weighing 230 mg. The reaction residue is chromatographed on silica gel with 5% MeOH/95% CH$_2$Cl$_2$ containing 0.6% NH$_4$OH to give the free base. The free base in absolute alcohol is treated with saturated ethanolic/HCl with stirring. The alcoholic solution is concentrated under reduced pressure to leave an oily residue. The oily residue is flushed with CH$_2$Cl$_2$ to yield analytically pure (3β,5β,14β,17β)-14-Amino-3-[[[[2-(Acetyloxy)-1-methylpropyl]amino] carbonyl]oxy]-14-amino-androstane-17-carboxylic Acid, Methyl Ester Hydrochloride Final Product.

EXAMPLE 50

14β-hydroxy-3β-((4'-amino-1'-piperindinyl))-carbonyloxy]-carden-20(22)-olide 3 g of digitoxigenine are dissolved in 25 ml of pyridine and the solution is kept at 60° on an oil bath. 2.42 g of 4-nitro-phenyl chloroformate are added and the reaction mixture is heated for 90 minutes. 0.5 g of 4-nitro-phenyl chloroformate again are added and the reaction is continued for 1 hour with heating.

The reaction mixture is allowed to cool at room temperature, extracted with toluene and washed with a diluted solution of sodium carbonate. The precipitate of carbonate is filtered and the filtrate is evaporated until dry (1.3 g).

After purification by chromatography on silica column and eluting with a methylene chloride-methyl alcohol mixture (99:1), 1.2 g of 14β-hydroxy-3β-[(4'-nitro-phenyloxy)-carbonyl-oxy]-carden-20(22)-olide are obtained.

The above product is caused to react with a 4-benzylimino-piperidine prepared as follows.

1.4 g of 4-aminobenzylpiperidine are added to a suspension of palladium black in a mixture of formic acid (4.4%) and methyl alcohol (95.6%). The mixture is stirred overnight at room temperature, then the catalyst if filtered and the solution is evaporated.

The residue is dissolved in 20 ml of ethyl alcohol, 0.8 ml of benzaldehyde are added to the solution, and the mixture is stirred at room temperature for 24 hours. The solution is evaporated until dry and the residue of 4-benzylimino-piperidine is used as such in the next step.

The 4-benzylimino-piperidine prepared as above is dissolved in 5.5 ml of dimethylformamide, and 0.6 g of the 14β-hydroxy-3β-[(4'-nitro-phenyloxy)-carbonyloxy]-carden-20(22)-olide are added to the solution, and the reaction mixture is stirred overnight at room temperature.

After extracting with ethyl acetate, washing with a diluted solution of sodium carbonate, evaporating and dissolving the residue in 20 ml of ethyl alcohol in the presence of 5.5 ml of 2N hydrochloric acid and stirring for 1 hour, distilled water is added and the bases are extracted with a 10% aqueous solution of hydrochloric acid. The solution is neutralized with ammonia and washed with ethyl acetate. The product obtained is purified by HPLC chromatography, eluting with a methylene chloride-methyl alcohol-ammoniac mixture (90:10:1), and 14β-hydroxy-3β-((4'-amino-1'-piperidinyl))-carbonyloxy]-carden-20(22)-olide Final Product is obtained.

EXAMPLE 51

14β-hydroxy-3β-(1'-piperidinyl)-carbonyloxy]-carden-20(22)-olide

A suspension of 400 mg of 14β-hydroxy-3β-[(4'-nitrophenyloxy)-carbonyloxy]-carden-20(22)-olide, obtained as described in Example 50, in 4 ml of dimethylformamide is prepared and 70 mg of piperidine is added thereto. The reaction mixture is stirred for 1 hour, extracted with ethyl acetate, washed with an aqueous solution of sodium carbonate, and then with distilled water. After evaporation until dry, the residue is purified by chromatography on silica column, eluting with a methylene chloride-methyl alcohol mixture (97:3), and pure 14β-hydroxy-3β-[1'-piperidinyl)-carbonyloxy]-carden-20(22)-olide is obtained. After a crystallisation in a mixture of ethyl acetate and ethyl alcohol, the Final Product, 14β-hydroxy-3β-(1'-piperidinyl)-carbonyloxy]-carden-20(22)-olide, is obtained as an amorphous powder.

EXAMPLE 52

14β-amino-3β-[(1'-piperidinyl)-carbonyloxy)]-5β-androstane-17β-carboxylic acid, methyl ester 620 mg of 14β-azido-3β-hydroxy-5β-androstane-17β-carboxylic acid methyl ester, are dissolved in 3.1 ml of anhydrous pyridine, while heating at 60° on an oil bath. 333 mg of 4-nitro-phenyl chloroformate are added and the reaction mixture is heated for 60 minutes under stirring. 166 mg of 4-nitro-phenyl chloroformate again are added and the reaction is continued for 1 hour.

After cooling, extracting with toluene, washing with a diluted aqueous solution of sodium carbonate, and then with distilled water, the toluene is evaporated, and the residue is purified by chromatography, eluting with a methylene chloride—heptane mixture (80:20) to yield 14β-azido-3β-[(4'-nitro-phenyloxy)carbonyloxy]-5β-androstane-17β-carboxylic acid methyl ester, which crystallises in a mixture of ethyl acetate and heptane (1:3). A suspension of the above derivative in 2 ml of dimethylformamide is prepared.

0.05 ml of piperidine are added at room temperature under stirring until all the 14-azido-carbonate is dissolved.

After extraction with ethyl acetate, washing with a diluted aqueous solution of sodium carbonate, and then with distilled water, drying and evaporation until dry, 180 mg of residue are obtained, corresponding to the 14β-azido-3β-(piperidino-carbonyloxy)-5β-androstane-17β-carboxylic acid methyl ester. The above compound (180 mg) is dissolved in 20 of hot ethyl alcohol, and this solution is added into a solution of 26 ml of ethyl alcohol containing 123 mg of tellurium powder and 91 mg of sodium borohydride under argon atmosphere. The reaction is continued for 5 hours at room temperature under stirring.

The reaction mixture is neutralized with a 10% solution of acetic acid in ethyl alcohol (pH 7), filtered on Celite, and the Celite is rinsed with a methylene chloride-ethyl alcohol mixture (1:1) and the filtrate is evaporated. The residue is dissolved in toluene, washed with a 10% aqueous solution of hydrochloric acid, and the aqueous acid phases are alkalinized with ammonia. After extraction and chromatography on a silica column, eluting with a methylene chloride-methyl alcohol-ammonia mixture (95.6:4:0.4), crystallization in ethyl acetate, colorless crystals of 14β-amino-3β-[(1'-piperidinyl)-carbonyl-oxy)]-5β-androstane-17-β-carboxylic acid methyl ester Final Product are obtained.

EXAMPLE 53

14β-amino-N-methyl-3β-[(R)-1'-hydroxymethyl-propylaminoformyloxy)]-5β-androstane-17β-carboxylic acid, methyl ester, hydrochloride 0.4 g of a mixture (1:1) of 2-methylamino-1-n-butyl alcohol and 2-dimethylamino-1-n-butyl alcohol are added to a solution of 0.68 g of 14β-azido-3β-[(4'-nitro-phenyloxy)carbonyloxy]-5β-androstane-17β-carboxylic acid methyl ester, prepared as described in Example 52, in 7.5 ml of dimethylformamide. The reaction mixture is stirred at room temperature for 3 hours, and then it is diluted with 60 ml of water.

After extraction with ethyl acetate, washing with a saturated solution of sodium bicarbonate, then with water, and then with a saturated NaCl solution, the organic phases are dried and evaporated until dry. 0.7 g of 14β-azido-N-methyl-3β-[(R)-1'-hydroxymethyl-propylaminoformyloxy)]-5β-androstane-17β-carboxylic acid, methyl ester, are obtained. 0.7 g of palladium hydroxide are added to a solution of 0.7 g of the above 14-azido derivative in 72 ml of a methyl alcohol solution of hydrazine under argon atmosphere, and the reaction mixture is refluxed for 7 hours, and overnight at room temperature.

After filtration on Celite, the filtrate is evaporated until dry and 0.9 g of crude product are obtained, which is purified by chromatography on silica, eluting with a methylene chloride-methyl alcohol-ammonia mixture (97:3:0.3), followed with dissolution in water, addition of 1.2N hydrochloric acid until pH 1, extraction with ethyl acetate and washing with water and a saturated NaCl solution. Some starting product remains in the organic phases, and the aqueous phases are alkalinized with sodium bicarbonate and extracted with a methylene chloride-methyl alcohol mixture (80:20) to obtain the 0.32 g of 14β-amino-N-methyl-3β-[(R)-1'-hydroxymethyl-propylaminoformyloxy)]-5β-androstane-17β-carboxylic acid, methyl ester Final Product are obtained. The hydrochloride salt of the Final Product is prepared by adding 0.2N hydrochloric acid in a methyl alcohol solution.

EXAMPLE 54

14β-amino-3β-[(4'-amino-1'-piperidinyl)]-carbonyloxy]-4-etienic acid, methyl ester 68 mg of tellurium powder and 44 mg of sodium borohydride are added into a methyl alcohol solution which has been degased with argon. The mixture is refluxed for 2 hours under stirring, then it is left to cool and 80 mg of 14β-azido-3β-hydroxy-4-etienic acid methyl ester are added and the reaction mixture is stirred at room temperature for 3 hours.

After filtration, washing with ethyl alcohol, extraction with methylene chloride and washing successively with water, sodium bicarbonate, and a saturated NaCl solution, the residue is purified by chromatography on silica, eluting with a methylene chloride-methyl alcohol-ammonia mixture (95:5:0.5), and 60 mg of 14β-amino-3β-hydroxy-4-etienic acid methyl ester.

The above 14-amino derivative is dissolved in methylene chloride under argon atmosphere, while stirring the solution, in the presence of dibutylurea and a molecular sieve (4 A). Two parts of p-nitrophenyl chloroformate are added at two hours interval, and a third part is added 5 hours later. The reaction is continued overnight at room temperature.

Thus, a 14β-amino-3β-[(4'-nitrophenyl)-carbonyloxy]-4-etienic acid, methyl ester is obtained, which is caused to react with 4-amino-piperidine in dimethylformamide. The reaction is carried for 20 hours out at 0° under stirring.

After extraction with ethyl acetate and washing according to the usual technique, the residue is filtered and purified by chromatography on silica column, eluting with a methylene chloride-methyl alcohol-ammonia mixture (95:5:0.5), and the 14β-amino-3β-[(4'-amino-1'-piperidinyl)]-carbonyloxy]-4-etienic acid methyl ester Final Product is obtained.

EXAMPLE 55

14β-amino-12β-hydroxy-3β-[(4'-amino-1'-piperidinyl)-carbonyloxy]-5β-androstane-17β-carboxylic acid, methyl ester, dihydrochloride This product is prepared by the same method as described in Example 52, but starting from 14β-azido-3β, 12β-dihydroxy-5β-androstane-17β-carboxylic acid methyl ester. The dihydrochloride is prepared from the corresponding base by addition of hydrochloric acid in a methyl alcohol solution.

EXAMPLE 56

14β-amino-3β-(1'-acetoxymethyl-(S)-propylamino-carbonyloxy)-5β-androstane-17β-carboxylic acid, methyl ester 1 g of 14β-amino-3β-hydroxy-5β-androstane-17β-carboxylic acid methyl ester, is dissolved in 30 ml of methylene chloride under argon atmosphere. 0.9 g of carbonyldiimidazole is added thereto and the reaction mixture is stirred for six hours at room temperature.

1.35 ml of (S) 2-amino-1-butyl alcohol are added, and the solution is stirred at room temperature for about two days. The reaction is followed by thin layer chromatography.

The solvent is concentrated until 10 ml and the mixture is kept under stirring for two days, and diluted with water, and then it is extracted with methylene chloride. The organic phases are washed with water and a saturated NaCl solution, dried on sodium sulfate, and evaporated until dry.

The residue thus obtained is purified by chromatography on a silica column, eluting with a methylene chloride-methyl alcohol-ammonia mixture (96:4:0.4), and 0.7 g of pure 14β-azido-3β-[(1'-hydroxymethyl-(S)-propylamino-carbonyl)oxy]-5β-androstane-17β-carboxylic acid methyl ester are obtained.

0.5 g of the above derivative is dissolved in 5 ml of methylene chloride, 130 mg of dimethylaminopyridine and 0.16 ml of acetic anhydride are added at 0° C.

The reaction mixture is stirred at 0° C. for 10 minutes and alkalinised with ammoniac (28% solution), and kept under stirring for one additional hour.

After extraction with methylene chloride, the organic phases are washed with water and a saturated NaCl solution, dried on sodium sulfate, and evaporated until dry, to produce 14β-amino-3β-(1'-acetoxymethyl-(S)-propylamino-carbonyloxy)-5β-androstane-17β-carboxylic acid, methyl ester final product.

EXAMPLE 57

14β-hydroxy-17β-aminomethyl-3β-(1'-hydroxymethyl-(R)-propylamino-carbonyloxy)-5β-androstane A solution of 6 ml of methylene chloride containing 100 mg of 3β,14β-dihydroxy-20-N-dibenzylamino-21-norpregnan is added under argon into 60 mg of carbonyldiimidazole, and the reaction mixture is stirred for two days at room temperature.

95 ml of (R) 2-amino-1-butyl alcohol are added, and the mixture is stirred at room temperature for about five days.

After evaporation until dry, the residue is taken up with methylene chloride. The organic phases are washed with water (3 times), dried on sodium sulfate, and evaporated until dry.

The crude residue thus obtained is purified by chromatography on silica column, eluting with a methylene chloride-methyl alcohol (98:2), and 0.12 g of pure 14β-hydroxy-3β-[(1'-hydroxymethyl-(R)-propylamino-carbonyl)oxy]-5β-21-norpregnane is obtained.

0.54 g of Pd(OH)$_3$ are added under argon into a solution of 54 ml of hydrazine containing 0.7 g of the above nor-pregnane derivative, and the reaction mixture is refluxed for one hour, and then filtered on Celite and rinsed with methyl alcohol. The filtrate is evaporated until dry and the crude product thus obtained is purified by chromatography on silica column, eluting with a methylene chloride-methyl alcohol-ammonia mixture (90:10:1) to yield the 14β-hydroxy-17β-aminomethyl-3β-(1'hydroxymethyl-(R)-propylamino-carbonyloxy)-5β-androstane final product.

EXAMPLE 58

3β-O-(piperidinoformyl)-ouabaigenine 3.5 g of di-O-acetyl-ouabaigenine are dissolved in 210 ml of methanol, and 8 ml of a 1N aqueous solution of sodium carbonate are added thereto. After stirring at room temperature for one hour, 3.7 ml of the same sodium carbonate aqueous solution are added, the mixture is stirred for two hours, and then 0.6 ml of sodium carbonate aqueous solution are added and the mixture is kept under stirring for one additional hour.

The crude residue is extracted with methylene chloride and purified by chromatography, eluting with a methylene chloride-methyl alcohol mixture (95:5), 0.5 g of isodigitoxigeninic acid methyl ester and 2 g of 11-O-acetyl-1,19-O-isopropylidene ouabaigenine are obtained.

The 11-O-acetyl-1,19-O-isopropylidene ouabaigenine obtained as indicated above (1.2 g) is dissolved in 11 ml of anhydrous pyridine at room temperature. 0.8 g of p-nitrophenyl chloro-formate are added slowly and progressively for six hours, and the reaction mixture is extracted with ethyl acetate, washed with a diluted sodium carbonate aqueous solution, then with distilled water, and then with a saturated NaCl solution.

After evaporation, the residue is taken up with toluene to remove the remaining pyridine, and after purification by chromatography on silica column, eluting with a methylene chloride-methyl alcohol mixture (95:5), 1 g of 3-O-(4-nitrophenyloxy)-acetyl-1,19-O-isopropylidene ouabaigenine are obtained.

The above carbonate (350 mg) is dissolved in 3.5 ml of dimethylformamide, and 56 ul of piperidine are added. After stirring for one hour, extraction with ethyl acetate, washing with a diluted bicarbonate aqueous solution, then with water, and drying, 325 mg of a crude crystal residue are obtained which is identified as 3β-O-(piperidinoformyl)-11-O-acetyl-1,19-O-isopropylidene ouabaigenine.

A suspension of 325 mg of the above acetonide in 1.8 ml of acetic acid (60% aqueous solution) is prepared and stirred for 24 hours at room temperature so as to obtain an homogeneous suspension.

Toluene is added thereto and the mixture is evaporated (two times). The residue is purified by chromatography on a Lichroprep silica column, eluting with a methylene chloride-methyl alcohol mixture (93:7), and 224 mg of 3β-O-(piperidinoformyl)-11-O-acetyl-ouabaigenine are obtained.

The above acetylated derivative (110 mg) is dissolved in 1 ml of methyl alcohol. 0.8 ml of triethylamine and 76 ul of water are added to the solution, and the reaction mixture is stirred for two days at room temperature.

After evaporation until dry, and purification by chromatography on a Dynamex silica column, eluting with a methylene chloride-methyl alcohol mixture (93:7), and crystallisation in ethyl acetate, pure 3β-O-(piperidinoformyl)-ouabaigenine final product are obtained.

Assessment of Pharmacological Activity

It is postulated that the positive inotropic effect of a cardiotonic steroid compound is due to its effect on the Na$^+$, K$^+$ pump in the sarcolemma of the cardiac muscle cells. Specifically, the cardiotonic steroids inhibit the Na$^+$, K$^+$-activated adenosine triphosphatase which in turn leads to an increase in intracellular calcium. Thus, more calcium is available to activate the contractile mechanism. See generally, Goodman and Gilman, *The Pharmacological Basis of Therapeutics*, Chapter 34 (8th Ed., 1990).

The positive inotropic activity of a new chemical entity is assessed both in isolated cardiac tissues and in whole animal models. The isolated tissue provides a direct measurement of the inotropic potential of a compound as the system is virtually free from metabolic, neurohormonal and absorption interferences which may influence the tissue response. The in vivo assays provide an assessment which takes into account those physiological parameters lacking in the isolated tissue assay.

In the assay for inotropic activity, papillary muscle strips from guinea pig hearts are utilized. Although the papillary muscle is involved more with valve function, the basic contractile response exhibited by this muscle is similar to that of ventricular muscle. For the assay, a segment of papillary muscle dissected from a guinea pig heart is suspended in an organ bath which provides the tissue with a temperature controlled, aqueous environment containing the substrates necessary for cellular function. By attaching a force transducer to the free end of the muscle strip such that the muscle is suspended between a fixed base and the transducer and applying an electrical stimulus, it is possible to measure shortening or contraction in response to various concentrations of test compounds. Under typical conditions, positive inotropy is defined as the increase in contractile force elicited by an unknown agent and the data is usually reported as the concentration of drug necessary to elicit a 50% increase in contractile force from baseline ($EC_{50}$).

The assessment of positive inotropy in vivo is made in two ways. The first is very similar to the measurement described for the in vivo method in that a strain gauge is sutured to the exterior of the heart to determine contractile force. In the second protocol, a force transducer is inserted into the left ventricle to detect pressure changes. The myocardial contractile force is correlated to the rate of pressure development within the left ventricle and is expressed as +dP/dt. In either case, the data is reported as the amount of drug necessary to achieve a level of activity such as 30% increase in contractility or +dP/dt (i.e., $ED_{30}$) and is expressed as mg drug/kg weight of the animal.

Pharmaceutical Compositions

The novel urethane-containing aminosteroid compounds of the present invention may be administered to humans or other mammals by a variety of routes, including, but not limited to, oral dosage forms and injections (intravenous, intramuscular, intraperitoneal and subcutaneous). Numerous other dosage forms containing the novel urethane-containing aminosteroid compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the urethane-containing aminosteroid compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the urethane-containing aminosteroid compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;
(b) the pharmaceutically-acceptable excipients; so long as the variants do not interfere in the activity of the particular active ingredient selected;
(c) the type of the excipient, and the concomitant desirable thickness and permeability (swelling properties) of said excipients;
(d) the time-dependent conditions of the excipient itself and/or within the excipients;
(e) the particle size of the granulated active ingredient; and
(f) the pH-dependent conditions of the excipients.

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols.

The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Compounds of the present invention may comprise from 0.1% to 99.9% by weight of the pharmaceutical compositions of the present invention. Preferably the compounds of the present invention comprise from 20% to 80% by weight of the pharmaceutical compositions of the present invention.

Accordingly, the pharmaceutical compositions of the present invention include from 15–95% of a urethane-containing aminosteroid compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described herein. It is well within the capabilities of one skilled in the art to vary the non-limiting examples described herein to achieve a broad range of pharmaceutical compositions.

The choice of a pharmaceutically-acceptable excipient to be used in conjunction with the urethane-containing aminosteroid compounds of the present invention is basically determined by the way the compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The preferred mode of administering these urethane-containing aminosteroid compounds is orally. The preferred unit dosage form is therefore tablets, capsules and the like, comprising a safe and effective amount of the urethane-containing aminosteroid compound of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

Various oral dosage forms can be used, including such solid forms as tablets, capsules, granules and bulk powders. These oral dosage forms comprise a safe and effective amount, preferably from 0.25 mg to 5.0 mg, of the urethane-containing aminosteroid. More preferably these oral dosage forms comprise 0.5–1.0 mg of the urethane-containing aminosteroid. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions comprise a safe and effective amount, preferably from 0.5 mg to 2.0 mg, of the urethane-containing aminosteroid. More preferably these topical compositions comprise 1.0 mg of the urethane-containing aminosteroid. Suitable carriers for topical administration preferably remain in place on the skin as a continuous film, and resist being removed by perspiration or immersion in water.

Generally, the carrier is organic in nature and capable of having dispersed or dissolved therein the urethane-containing aminosteroid. The carrier may include pharmaceutically-acceptable emollients, emulsifiers, thickening agents, and solvents.

The compositions of this invention can also be administered via the inhalation route. Such compositions are prepared in a matrix comprising a solvent such as water or a glycol, preservatives such as methyl or propyl paraben and propellants such as nitrogen or carbon dioxide.

Additionally, the compositions of this invention can be administered via a subcutaneous implant formed from silicone elastomers, ethylene vinyl acetate co-polymers or lactic-glycolic co-polymers.

In order to illustrate how to prepare pharmaceutical compositions containing the novel urethane-containing 14-amino-steroid compounds of the present invention, the following non-limiting pharmaceutical composition examples are presented.

Pharmaceutical Composition Examples

EXAMPLE 1

An immediate release oral dosage form (tablet) containing the (3β,5β,14β,17β)-3-[[[[2-(Acetyloxy)-1-methylpropyl]amino]carbonyl]oxy]-14-aminoandrostane-17-carboxylic Acid, Methyl Ester Hydrochloride has the following composition:

| Active Ingredient | Amount |
| --- | --- |
| (3β,5β,14β,17β)-3-[[[[2-(Acetyloxy)-1-methylpropyl]mino]carbonyl]oxy]-14-aminoandrostane-17-carboxylic Acid, Methyl Ester Hydrochloride | 1.0 mg |
| Excipients | |
| Microcrystalline cellulose | 28.5 mg |
| Lactose, hydrous | 67.2 mg |
| Crospovidone | 3.0 mg |
| Magnesium stearate | 0.3 mg |

Manufacturing directions: (for 10,000 tablets)

1) 10.0 g of the drug, 285.0 g of microcrystalline cellulose, 672.0 g of lactose and 30.0 g of crospovidone are mixed in a Patterson-Kelley (PK) or other suitable blender,
2) the above mixture is blended with 3.0 g of magnesium stearate in a PK or suitable blender,
3) the above final blend is compacted into 100.0 mg tablets on a suitable tableting machine.

EXAMPLE 2

A parenteral dosage form containing the (3β,5β,14β,17β)-3-[[[3-(Acetyloxy)-1-piperidinyl]carbonyl]oxy]-14-amino-N-methyl-androstane-17-carboxamide Hydrochloride and suitable for use as an intravenous (I.V.) injection has the following composition:

| Active Ingredient | Amount |
| --- | --- |
| (3β,5β,14β,17β)-3-[[[3-(Acetyloxy)-1-piperidinyl]carbonyl]oxy]-14-amino-N-methylandrostane-17-carboxamide Hydrochloride | 1.0 mg |
| Excipients | |
| Mannitol | 200.0 mg |
| Citric acid/sodium citrate | quantity sufficient to adjust the pH between 5.5–6.5 |

Manufacturing directions: (for 1000 vials)

1) 1.0 g of the drug, 200.0 g of mannitol and sufficient sodium citrate and citric acid are dissolved in 2200.0 ml of sterile, deionized water for injection,
2) the above solution is filtered through a 0.22 micron sterile membrane filter,
3) 2.2 ml of the above sterile solution is filled into Type I glass vials and then lyophilized in a suitable lyophilizer,
4) the vials, after lyophilization, are stoppered with bromobutyl or other suitable stoppers and sealed. The lyophilized product is reconstituted with 2.0 ml of sterile water for injection immediately prior to use.

EXAMPLE 3

A sustained release oral dosage form (tablet) containing the (3β(S),5β,14β,17β)-14-Amino-3-[[(3-hydroxy-1-piperidinyl)carbonyl]oxy]androstane-17-carboxylic Acid, Methyl Ester Hydrochloride has the following composition:

| Active Ingredient | Amount |
| --- | --- |
| (3β(S),5β,14β,17β)-14-Amino-3-[[(3-hydroxy-1-piperidinyl)carbonyl]oxy]androstane-17-carboxylic Acid, Methyl Ester Hydrochloride | 5.0 mg |
| Excipients | |
| Hydroxypropylmethylcellulose | 120.0 mg |
| Lactose, hydrous | 120.0 mg |
| Magnesium stearate | 12.0 mg |
| Colloidal silicon dioxide | 4.0 mg |

Manufacturing directions: (for 10,000 tablets)

1) 50.0 gm of the drug, 1.2 kg of hydroxypropylmethylcellulose and 1.2 kg of lactose are mixed intimately in a twin shell Patterson-Kelley or suitable mixer,
2) to the above mix are added 120 gm of magnesium stearate and 40 gm of colloidal silicon dioxide and this is lightly blended in a suitable mixer,
3) the above blend is compacted into tablets weighing 261.0 mg on a suitable tablet press.

In addition to the preceding three examples, the drug active ingredient is formulated into a number of different dosage forms:

1) a pharmaceutical aerosol containing solvent (e.g. water, glycols), preservatives (methyl or propyl parabens) and propellants (nitrogen, carbon dioxide) or other suitable excipients,
2) a rectal suppository containing theobroma oil or polyethylene glycols,
3) a subcutaneous implant containing silicone elastomers, ethylene-vinyl acetate copolymers, lactic-glycolic copolymers and hydrogels or other suitable polymers, 4) commercially available implantable devices,
5) a transdermal system containing silicone fluid in an ethylene-vinyl acetate copolymer membrane or other suitable ingredients for delivery with or without the aid of iontophoresis,
6) a buccal mucoadhesive patch containing hydrocolloid polymers (hydroxyethyl cellulose, hydroxy-propyl cellulose, povidone) and other suitable polymers.

Methods of Treatment

The term Congestive Heart Failure ("CHF") as used herein, denotes a progressive disease wherein the hemodynamic capacity as well as the structural integrity of the heart itself is increasingly and irreversibly compromised. The progression of CHF according to the patient's symptoms has been classified into four functional classifications by the New York Heart Association (NYHA).

New York Heart Association Functional Classification

Class

I. Patients with cardiac disease but without resulting limitations of physical activity. Ordinary physical activity does not cause undue fatigue, palpitation, dyspnea, or anginal pain.

II. Patients with cardiac disease resulting in slight limitation of physical activity. They are comfortable at rest. Ordinary physical activity results in fatigue, palpitation, dyspnea, or anginal pain.

III. Patients with cardiac disease resulting in marked limitation of physical activity. They are comfortable at rest. Less than ordinary physical activity causes fatigue, palpitation, dyspnea, or anginal pain.

IV. Patient with cardiac disease resulting in inability to carry on any physical activity without discomfort. Symptoms of cardiac insufficiency or of the anginal syndrome may be present even at rest. If any physical activity is undertaken, discomfort is increased.

NYHA Classes III and IV, also referred to as overt congestive heart failure, are often treated by administering compounds that increase cardiac contractility by exerting a positive inotropic effect. The reference compound for increasing cardiac contractility is oral digoxin. Treating the symptoms of the overt CHF by administering inotropes to increase CO to meet the metabolic needs of the body can improve the quality of life for a CHF patient because the heart can better supply the metabolic need of the body. Conventional wisdom, however, indicates that an inotrope, such as digitalis, might increase mortality rates because the inotropic action creates an extra work load for the heart. Furthermore, digitalis has a narrow therapeutic:toxic dose ratio and administration of digitalis at an earlier than Class III NYHA functional classification may not be prudent.

Additionally, the bipyridine inotrope, Milrinone, has been shown to aggravate ventricular arrhythmias and possibly increase mortality. See DiBianco, R., et al. "A Comparison of Oral Milrinone, Digoxin, and Their Combination in the Treatment of Patients with Chronic Heart Failure", *N. Engl. J. Med.* 320:677 (1989).

The term "hemodynamic" as used herein, refers to the mechanical capability of the heart. The initial hemodynamic consequence of heart failure is a decrease in stroke volume which is a measurement of the amount of blood ejected with each heart beat. The heart then compensates to increase the CO to maintain flow to the vital organs. As the heart failure worsens, intracardiac filling pressures are elevated as well as pulmonary and venous pressures. The heart is increasingly unable to supply the required CO.

The term "structural damage" as used herein, refers to the microscopic and macroscopic changes in the heart of a person suffering from CHF. Structurally, on a microscopic level the following changes occur: The early stage of cardiac hypertrophy is characterized morphologically by increases in the size of myofibrils and mitochondria as well as enlargement of mitochondria and nuclei. Muscle cells are larger than normal, but cellular organization is largely preserved. At a more advanced stage of hypertrophy, preferential increases in the size or number of specific organelles, such as mitochondria, as well as irregular addition of new contractile elements in localized areas of the cell, result in subtle abnormalities of cellular organization and contour. Adjacent cells may vary in their degree of enlargement.

Cells subjected to long-standing hypertrophy show more obvious disruptions in cellular organization, such as markedly enlarged nuclei with highly lobulated membranes, which displace adjacent myofibrils and cause breakdown of normal Z-band registration. The early preferential increase in mitochondria is supplanted by a predominance by volume of myofibrils. The late stage of hypertrophy is characterized by cell death and a loss of contractile elements with marked disruption of Z bands, severe disruption of the normal parallel arrangement of the sarcomeres, dilation and increased tortuosity of T tubules, and replacement of the contractile elements with fibrosis tissue. See Braunwald, *Heart Disease: A Textbook of Cardiovascular Medicine*, Vol. 1 (3rd ed. 1988). These microscopic changes are revealed on a macroscopic level by cardiac hypertrophy or enlargement of the heart. The hypertrophying heart becomes less efficient due to microscopic changes causing loss of contractile elements and fibrotic deposition and the patient's clinical symptoms worsen as he progresses through each NYHA functional classification.

The compounds of the present invention increase cardiac contractility. The dosage range can be between 0.25 mg and 5 mg per day as determined by the attending physician according to the mode of administration, the severity of the CHF and the duration of treatment.

In order to illustrate the particular utility of these novel urethane-containing aminosteroid compounds, for the treatment of CHF, the following non-limiting examples are presented.

Clinical Examples

EXAMPLE 1

An obese 65 year old white female with a 20 year history of non-insulin dependent diabetes mellitus and hypertension, and a myocardial infarction 2 years prior, is admitted to the coronary care unit after 12 hours of symptoms with an acute inferior myocardial infarction. Her hospital course is complicated by acute pulmonary edema which manifests itself by severe dyspnea at rest, orthopnea, jugular venous distention, bilateral rales to mid-scapula; a dilated heart and bilateral infiltrates on CXR. Her pulmonary capillary wedge pressure is 35 mmHg. She is treated with morphine, oxygen, intravenous nitroglycerin, a loop diuretic and 0.25 mg of (3β,5β,14β,17β)-3-[[[3-(Acetyloxy)-1-piperidinyl]carbonyl]oxy]-14-amino-N-methylandrostane-17-carboxamide Hydrochloride intravenously every 4 hours for three days, followed by 0.25 mg of (3β,5β,14β,17β)-3-[[[3-(Acetyloxy)-1-piperidinyl]carbonyl]oxy]-14-amino-N-methylandrostane-17-carboxamide Hydrochloride orally once a day. She improves on this regimen and is discharged in 10 days with dyspnea on mild exertion (mild congestive heart failure, NYHA Class II) to be followed as an outpatient on a diuretic, ACE inhibitor, nitroglycerin and 0.25 mg orally of (3β,5β,14β,17β)-3-[[[3-(Acetyloxy)-1-piperidinyl] carbonyl]oxy]-14-amino-N-methylandrostane-17-carboxamide Hydrochloride per day.

EXAMPLE 2

A 44-year old black male with a history of long-standing uncontrolled hypertension and a one year history of moderate (NYHA Class III) congestive heart failure presents with several episodes of presyncope over the preceding 2 weeks. He also complains of fatigue and dyspnea when getting dressed. Medications include digoxin (0.25 mg/day), lasix and ACE inhibitor. He has an S3 gallop, pitting ankle edema, left ventricular hypertrophy and occasional PVCs on ECG. Additional evaluation discloses frequent multifocal ventricular ectopy and a run of non-sustained ventricular tachycardia on Holter monitoring, an ejection fraction of 30% by radionuclide ventriculography and a serum digoxin level of 2.2 ng/ml. The arrhythmias and pre-syncope are suspected to be a result of digitalis toxicity, and the drug is discontinued. (3β(S),5β,14β,17β)-14-Amino-3-[[(3-hydroxy-1-piperidinyl)carbonyl]oxy]androstane-17-carboxylic Acid, Methyl Ester Hydrochloride is instituted at an oral dose of 0.25 mg per day. Because of persistence of fatigue and dyspnea, the dose is increased over the next six weeks to 1 mg daily with no additional episodes of pre-syncope, a reduction of PVCs and absence of nonsustained ventricular tachycardia on repeat Holter and an increase in the ejection fraction to 38%. His dyspnea with self-care activities such as dressing is resolved and he is able to work in his garden with mild occasional dyspnea (NYHA Class II). At one year follow-up his condition is unchanged.

EXAMPLE 3

A 24 year-old previously healthy Chinese female presents with a two month history of dyspnea with strenuous exertion. There is no family history of heart disease; she is a non-smoker, and does not drink alcohol. Physical exam is normal with the exception of tachycardia and a laterally displaced point of maximum impulse. A heart rate of 105 and non-specific T wave flattening are seen on ECG, and CXR reveals an enlarged heart. Echocardiogram shows biventricular enlargement with global hypokinesia, and an ejection fraction of 40%. The valves appear normal. A symptom limited treadmill exercise test shows no evidence of ischemia. A diagnosis of idiopathic dilated cardiomyopathy, NYHA Class I, is made. Initial treatment with an ACE inhibitor produces an intolerable cough, and is therefore discontinued. (3β(R),5β,14β, 17β)-14-Amino-3-[[(3-hydroxy-1-piperidinyl)carbonyl]oxy]androstane-17-carboxylic Acid, Methyl Ester Hydrochloride is administered orally at a dosage of 1 mg twice a day, and over the next month her ability to exercise improves. There is also an increase in the ejection fraction (by echocardiogram) to 55%, and an increase in exercise time of 200 seconds on the treadmill exercise test.

EXAMPLE 4

A 55 year old white male with a history of two previous myocardial infarctions and whose father died suddenly at age 50, is being maintained on isosorbide dinitrate and a beta blocker with stable effort angina for two years. Over the preceding month, however, he develops dyspnea on walking up one flight of stairs, swelling of the ankles at night and occasional paroxysmal nocturnal dyspnea.

He has a resting heart rate of 90, 1+ pitting edema of the ankles, an S3 gallop, an enlarged heart and Kerly B lines on CXR. A diagnosis of mild (NYHA Class II) congestive heart failure due to ischemic heart disease is made. His beta blocker is discontinued by gradual tapering, and an ACE inhibitor and diuretic added, but on this new regimen his congestive heart failure worsens. (3β(S),5β,14β,17β)-3-[[[[2-(Acetyloxy)-1-phenylethyl]amino]carbonyl]oxy]-14-amino-N-methylandrostane-17-carboxamide Hydrochloride is orally administered at a dose of 4 mg once daily. His dyspnea and edema resolves (NYHA Class I), heart rate decreased to 75, S3 disappeared, heart size decreases and congestion on CXR resolves. There is an increase in exercise time of 170 seconds on his treadmill test performed 1 month later. No further worsening occurs over the next 2 years.

EXAMPLE 5

A 60 year old black female who has a history of three myocardial infarctions and resultant severe (NYHA Class IV) congestive heart failure has been hospitalized with four times in the preceding six weeks for acute decompensation despite therapy with maximally tolerated doses of lasix, isosorbide dinitrate, digoxin, and an ACE inhibitor. Her symptoms include edema, dyspnea at rest, 3 pillow orthopnea, marked fatigue and mental confusion. A decision is made to discontinue the digoxin and institute treatment with (3β,5β,14β,17β)-14-Amino-3-[[[(2-hydroxy-1-methylpropyl)amino]carbonyl]oxy]androstane-17-carboxylic Acid, Methyl Ester Hydrochloride. The initial dose of (3β,5β,14β,17β)-14-Amino-3-[[[(2-hydroxy-1-methylpropyl)amino]carbonyl]oxy]androstane-17-carboxylic Acid, Methyl Ester Hydrochloride is 0.5 mg orally administered once a day, but titration to 2 mg three times a day is required over a 2 month period to adequately control her symptoms. At the end of the two month period, her orthopnea, confusion and edema resolve; and she has an improved ability to perform activities of daily living such as dressing herself without dyspnea (NYHA Class III, moderate congestive heart failure). Her ejection fraction also improves from 20 to 35%. She remains stable over the following three months.

EXAMPLE 6

A recently (2 months) sober 60 year old white male alcoholic, with a 30 year history of cigarette smoking is admitted to the hospital with a three month history of progressively worsening dyspnea on exertion, fatigue, orthopnea, edema and paroxysmal nocturnal dyspnea. He has dyspnea while brushing his teeth. Physical examination reveals a cachectic male in moderate distress with a respiratory rate of 30 per minute, a heart rate or 110 bpm, blood pressure 90/50, an S3 gallop, 2+ pitting edema to the knees, jugular venous distention, hepatomegaly, ascites, bibasilar rales and an enlarged heart. Extensive evaluation provides diagnoses of chronic alcoholic hepatitis, chronic obstructive pulmonary disease, and moderate (NYHA Class III) congestive heart failure due to toxic (alcoholic) cardiomyopathy. Treatment is begun with hydrochlorthiazide, an ACE inhibitor and (3β(S),5β,14β,17β)-14-Amino-3-[[[(1-hydroxymethyl-2-methylpropyl)amino]thioxomethyl]oxy] androstane-17-carboxylic Acid, Methyl Ester Hydrochloride at a daily oral dose of 0.25 mg per day. He improves rapidly and is discharged in a week. After a 20 pound weight loss he is able to walk to the mailbox with mild dyspnea (NYHA Class II). His respiratory rate is 20, heart rate 90, the S3 is no longer audible, and the edema and rales resolve. The hepatomegaly persists unchanged, but the ascites is slightly diminished. The ejection fraction increases from 32 to 45% and the heart size decreases.

EXAMPLE 7

A 70 year old sedentary white female is noted to have an enlarged heart on CXR done prior to elective surgery for a cataract. She denies any history of chest pain, dyspnea or any history of hypertension, diabetes or cardiac disease. Her ECG shows non-specific ST-T wave changes; and standard clinical laboratory evaluations are normal. A treadmill exercise test is terminated due to fatigue without evidence of coronary artery disease. An echocardiogram shows biventricular enlargement, normal valves and an ejection fraction of 30%. She is given a preventative course of (3β(S),5β,14β,17β)-14-Amino-3-[[[(2-hydroxy-1-phenylethyl)-amino]carbonyl]oxy]androstane-17-carboxylic Acid, Methyl Ester Hydrochloride at 0.25 mg orally per day. Her ejection fraction increases to 40% and she is asymptomatic at the time of hospitalization for surgery for a second cataract 5 years later.

What is claimed is:

1. Urethane-containing aminosteroid compounds and the pharmaceutically-acceptable acid salts or esters thereof of the general formula wherein:

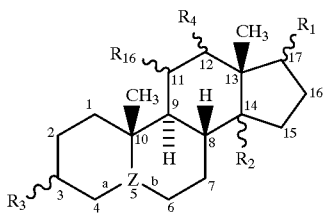

a) $R_1$ is
   (i) $COOR_5$, where
       $R_5$ is hydrogen; a 1–6 carbon lower alkyl group; a 1–6 carbon lower alkyl group containing 2 to 6 carbon atoms substituted by an amino group; an arylalkyl group or a carbocyclic ring or
   (ii) $CHR_6OH$, where $R_6$ is a hydrogen atom or 1–6 carbon group lower alkyl; or
   (iii) $COR'''$, where $R'''$ is hydrogen; 1–6 carbon lower alkyl; amino; 1–6 carbon lower alkyl substituted amino; or dialkylamino; or
   (iv) $CHR_6NHY$, where Y is hydrogen or a 1–6 carbon lower alkyl; and
b) $R_2$ is
   (i) $-NR_7R_8$, where
       $R_7$ and $R_8$, which may be the same or different; are hydrogen atoms or a 1–6 carbon lower alkyl group; and
c) $R_3$ is a urethane-containing moiety, where

wherein X can be O or S; R'R" are independently selected from hydrogen; substituted or unsubstituted linear; branched or cyclic 1–6 carbon lower alkyl; alkylaminoalkyl; arylalkyl; aryl; wherein further said substituents are selected from hydroxy; amino; alkoxy; 1–6 carbon alkyl; amino; aryl; hydroxyalkyl; alkylaminoalkyl; arylalkyl or and d) $R_4$ is
   (i) OH, or
   (ii) H, or
   (iii) $OR_{13}$, where $R_{13}$ is acetoxy; benzoxy; or arylalkyl and
e) $R_{14}$ is
   (i) OH, or
   (ii) H, or
   (iii) $OR_{13}$, where $R_{13}$ is acetoxy; benzoxy; or arylalkyl and
f) Z is
   (i) —CH—, where a and b are single bonds, or
   (ii) =C, where either a or b is a double bond.

2. A compound according to claim 1, wherein $R_1$ is $COOR_5$ and $R_5$ is a 1–6 carbon lower alkyl; $R_2$ is $NH_2$; $R_3$ is a urethane-containing moiety;

wherein X can be O or S; R'R" are independently selected from hydrogen; substituted or unsubstituted linear, branched or cyclic 1–6 carbon lower alkyl; alkylaminoalkyl; wherein further said substituents are selected from hydroxy; amino; alkoxy; 1–6 carbon lower alkyl; amino; aryl; hydroxyalkyl; amino; alkylaminoalkyl; or arylalkyl.

3. A compound according to claim 2, wherein X is 0; R" is hydrogen; R' is a substituted, branched 1–6 carbon lower alkyl.

4. A compound according to claim 2, wherein R" is hydrogen and R' is substituted with hydroxy; alkoxyl arylalkyl; or a 1–6 carbon lower alkyl.

5. A compound according to claim 1, selected from the group consisting of: (3β,5β,14β,17β)-3-[[[2-(Acetyloxy)-1-methylproypl]amino]carbonyl]oxy]14-aminoandrostane- (3β(S),5β,14β,17β)-3-[[[2-Acetyloxy)-1-phenylethyl] amino]carbonyl]oxy]-14-amino-N-methylandrostane-17-carboxamide Hydrochloride; (3β,5β,14β,17β)-14-Amino-3-[[[2-hydroxy-1-methylpropyl)amino]carbonyl]oxy] androstane-17-carboxylic Acid, Methyl Ester Hydrochloride; (3β(S),5β,14β,17β)-14-Amino-3[[[(1-hydroxymethyl-2-methylpropyl)amino]thioxomethyl]oxy] androstane-17-carboxylic Acid, Methyl Ester Hydrochloride; (3β(S),5β,14β,17β)-14-Amino-3-[[[(2-hydroxy-1-phenylethyl)amino]carbonyl]oxy]androstane-17-carboxylic Acid, Methyl Ester Hydrochloride; (3β,5β,14β,17β)-14-Amino-3-[[[(4-aminophenyl)amino]carbonyl]oxy] androstane-17-carboxylic Acid, Methyl Ester Dihydrochloride; (3β,5β,14β,17β)-14-Amino-3-[[[(2-hydroxyethyl) methylamino]carbonyl]oxy]androstane-17-carboxylic Acid, Methyl Ester Hydrochloride; (3β,5β,14β,17β)-14-Amino-3- [[[[1-(hydroxymethyl)-2-methylpropyl]amino]carbonyl] oxy]androstane-17-carboxylic Acid, Methyl Ester Hydrochloride; (3β, 5β,14β,17β)-14-Amino-3-[[[[1-(hydroxymethyl)propyl]amino]carbonyl]]oxy]androstane-17-carboxylic Acid, Methyl Ester Hydrochloride.

6. A pharmaceutical composition comprised of a safe and effective amount of from 15 to 95% of a compound of claim 1, or mixtures thereof, and from 5 to 85% pharmaceutically-acceptable excipients.

7. A pharmaceutical composition according to claim 6, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

8. A pharmaceutical composition according to claim 7 comprised of from 15–95% of the compound of claim 1 (or mixtures thereof); 0–2% flavoring agents; 0–50% co-solvents, 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

9. A pharmaceutical composition comprised of a safe and effective amount of from 15 to 95% of a compound of claim 2, or mixtures thereof, and from 5 to 85% pharmaceutically-acceptable excipients.

10. A pharmaceutical composition according to claim 9, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

11. A pharmaceutical composition according to claim 10 comprised of from 15–95% of the compound of claim 3 (or mixtures thereof); 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

12. A method of treatment for humans or other mammals afflicted with congestive heart failure comprising administering to said human or other mammal a safe and effective amount of the pharmaceutical composition of claim 6.

13. A method of treatment for humans or other mammals afflicted with congestive heart failure comprising administering to said human or other mammal a safe and effective amount of the pharmaceutical composition of claim 9.

* * * * *